(12) United States Patent
Raleigh et al.

(10) Patent No.: US 8,948,842 B2
(45) Date of Patent: Feb. 3, 2015

(54) RADIATION TREATMENT WITH MULTIPLE IMAGING ELEMENTS

(75) Inventors: Gregory Raleigh, Woodside, CA (US); Jose Tellado, Mountain View, CA (US); Alireza Raissinia, Monte Sereno, CA (US)

(73) Assignee: Headwater Partners II LLC, Redwood City, CA (US)

( * ) Notice: Subject to any disclaimer, the term of this patent is extended or adjusted under 35 U.S.C. 154(b) by 46 days.

(21) Appl. No.: 13/550,541

(22) Filed: Jul. 16, 2012

(65) Prior Publication Data
US 2013/0006093 A1 Jan. 3, 2013

Related U.S. Application Data

(63) Continuation-in-part of application No. 13/356,601, filed on Jan. 23, 2012.

(60) Provisional application No. 61/435,195, filed on Jan. 21, 2011.

(51) Int. Cl.
*A61B 5/05* (2006.01)
*A61N 5/10* (2006.01)
(Continued)

(52) U.S. Cl.
CPC .............. *A61N 5/1049* (2013.01); *A61B 6/032* (2013.01); *A61B 6/12* (2013.01); *A61B 6/466* (2013.01); *A61B 5/0037* (2013.01); *A61B 5/0035* (2013.01); *A61B 6/037* (2013.01);
(Continued)

(58) Field of Classification Search
CPC .................... A61N 5/1049; A61N 2005/1061; A61B 6/032; A61B 6/12; A61B 6/466; A61B 5/0037; A61B 5/0035; A61B 6/037; A61B 6/4085; A61B 8/085; A61B 6/4417; A61B 6/5247

USPC ........................... 600/407–480; 382/128–132
See application file for complete search history.

(56) References Cited

U.S. PATENT DOCUMENTS 5,207,223 A 5/1993 Adler
6,144,875 A 11/2000 Schweikard et al.
(Continued)

OTHER PUBLICATIONS

"Prediction of respiratory tumour motion for real-time image-guided radiotherapy", G. C. Sharp et al., Phys. Med. Biol. 49 (2004), 425-440.
(Continued)

*Primary Examiner* — Sanjay Cattungal
(74) *Attorney, Agent, or Firm* — Brian R. Short

(57) ABSTRACT

Methods, and apparatuses are provided that include a first imaging element configured to generate a first observation of a first object, the first observation of the first object being generated at a first time, wherein the first object is associated with a volume of interest (VOI). The system further includes a second imaging element configured to generate a first observation of a second object, wherein the first observation of the second object is generated at a second time, and the second object is associated with the VOI. A first positioning of the VOI is determined based on the first observation of the first object and the first observation of the second object, a third time for the first imaging element is determined based on a positioning parameter associated with the first positioning of the VOI, and a second observation of the first object is generated at the third time.

50 Claims, 25 Drawing Sheets

(51) Int. Cl.
*A61B 6/03* (2006.01)
*A61B 6/12* (2006.01)
*A61B 6/00* (2006.01)
*A61B 5/00* (2006.01)
*A61B 8/08* (2006.01)

(52) U.S. Cl.
CPC .............. *A61B 6/4085* (2013.01); *A61B 8/085* (2013.01); *A61N 2005/1061* (2013.01); *A61B 6/4417* (2013.01); *A61B 6/5247* (2013.01)
USPC ............ 600/411; 600/407; 382/131; 382/132

(56) References Cited

U.S. PATENT DOCUMENTS

| | | | |
|---|---|---|---|
| 7,352,370 B2 * | 4/2008 | Wang et al. | 345/424 |
| 7,453,983 B2 | 11/2008 | Schildkraut et al. | |
| 7,469,035 B2 | 12/2008 | Keall et al. | |
| 7,515,681 B2 | 4/2009 | Ebstein | |
| 7,567,697 B2 | 7/2009 | Mostafavi | |
| 7,590,219 B2 | 9/2009 | Maurer, Jr. et al. | |
| 7,623,623 B2 | 11/2009 | Raanes et al. | |
| 7,657,301 B2 | 2/2010 | Mate et al. | |
| 7,789,561 B2 * | 9/2010 | Wu et al. | 378/206 |
| 7,792,249 B2 | 9/2010 | Gertner et al. | |
| 7,842,929 B2 | 11/2010 | Krautim et al. | |
| 7,873,403 B2 | 1/2011 | Lachner et al. | |
| 8,121,368 B2 * | 2/2012 | Wiersma et al. | 382/128 |
| 8,130,907 B2 | 3/2012 | Maurer, Jr. et al. | |
| 2006/0274061 A1 | 12/2006 | Wang et al. | |
| 2007/0076846 A1 | 4/2007 | Ruchala et al. | |
| 2007/0232897 A1 | 10/2007 | Horndler et al. | |
| 2008/0039713 A1 * | 2/2008 | Thomson et al. | 600/411 |
| 2008/0109013 A1 * | 5/2008 | Fu et al. | 606/130 |
| 2008/0212737 A1 | 9/2008 | D'Souza et al. | |
| 2009/0180666 A1 | 7/2009 | Sheng et al. | |
| 2009/0257557 A1 | 10/2009 | Sumanaweera et al. | |
| 2010/0282983 A1 | 11/2010 | Wright et al. | |
| 2011/0180731 A1 | 7/2011 | Welsh | |
| 2011/0200170 A1 | 8/2011 | Nord et al. | |
| 2011/0211665 A1 * | 9/2011 | Maurer et al. | 378/9 |
| 2011/0235860 A1 | 9/2011 | Keall et al. | |

OTHER PUBLICATIONS

"Performance and characteristics of an IR localizing system for radiation therapy", Y. Lyatskaya et al., Journal of Applied Clinical Medical physics, vol. 7, No. 2, 2006.

"Methods and tools for navigated radiotherapy", Otto A. Sauer et al., GMS CURAC 2006; 1:Doc15.

"Development of a geometry-based respiratory motion-simulating patient model for radiation treatment dosimetry", J. Zhang et al, Journal of Applied clinical medical physics, vol. 9, Num 1, winter 2008.

"Delivery of four-dimensional radiotherapy with TrackBeam for moving target using a dual-layer MLC: dynamic phantoms study", Yaxi Liu, Journal of Applied Clinical Medical Physics, vol. 10, No. 2 (2009).

"Geometric accuracy of a novel gimbals based radiation therapy tumor", Tom Depuydt et al., Radiation and Oncology 98 (2011) 365-372.

"The comparative performance of four respiratory motion predictors for real-time tumour tracking", A. Krauss et al., Physics in Medicine and Biology, 2011, pp. 5303-5317, vol. 56.

"Robotic Tumor Tracking Techniques in Radiation Therapy", Ivan Buzurovic, Advances in Robotics & Automation, vol. 1, Issue 1, 2012.

Raun, D. et al., "Real-time prediction of respiratory motion based on local regression methods", Phys. Med. Biol. 2007, 16 pages, vol. 52.

\* cited by examiner

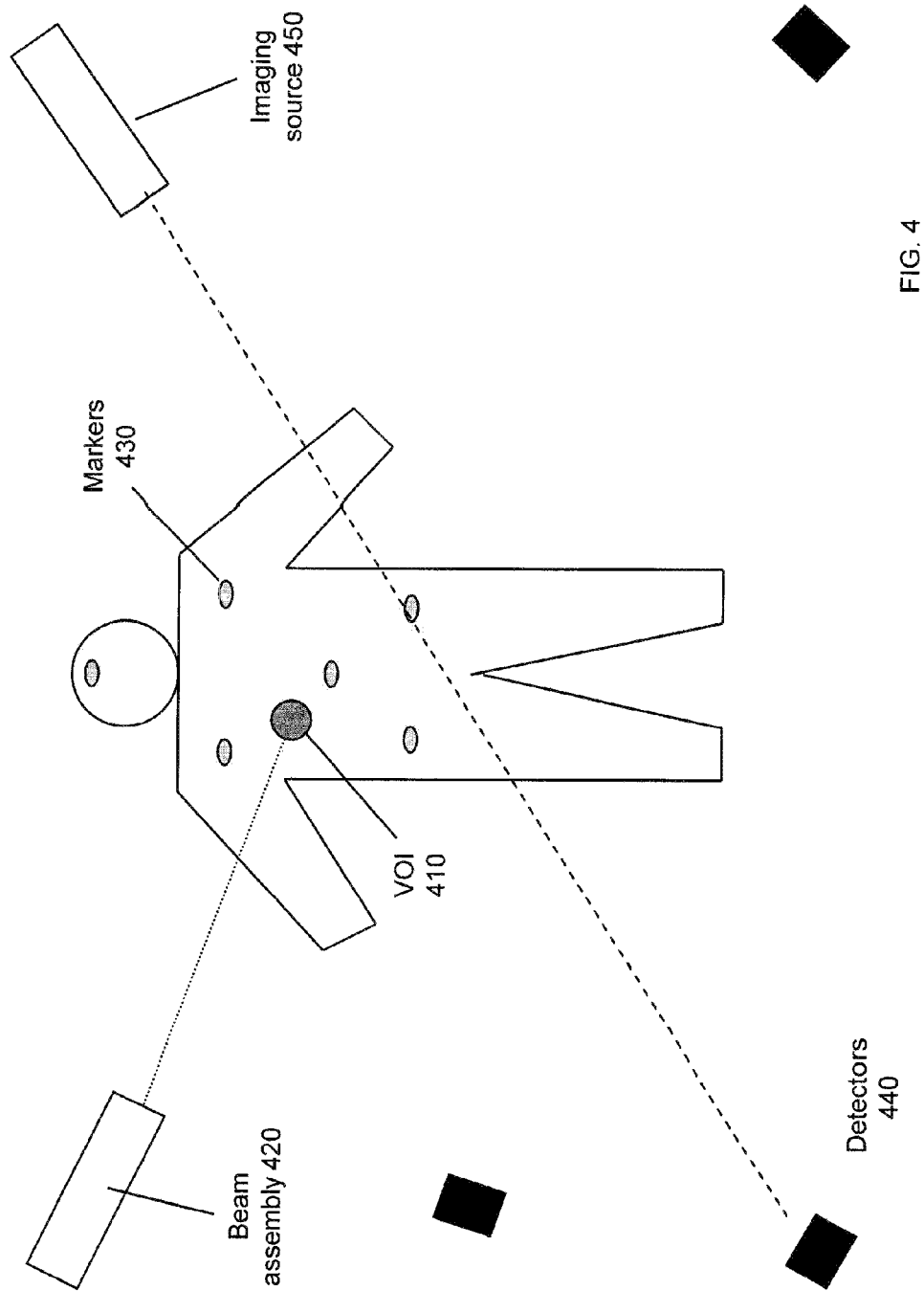

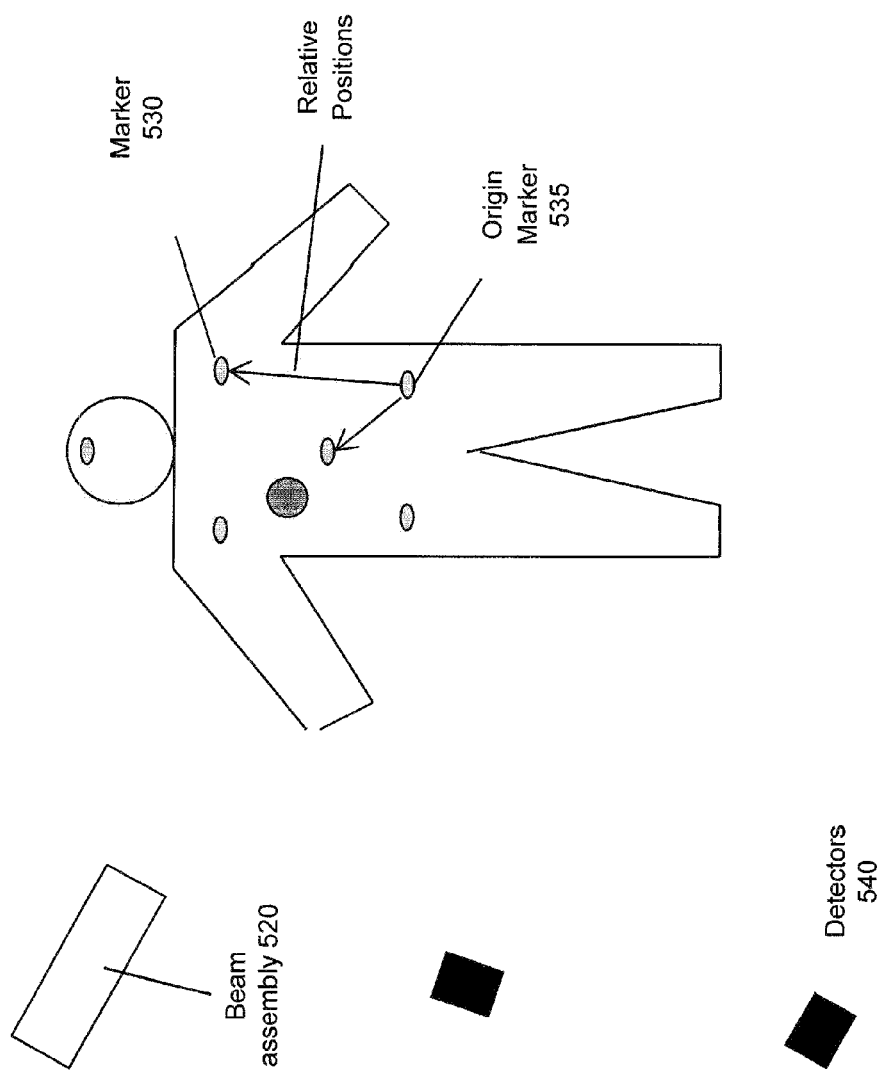

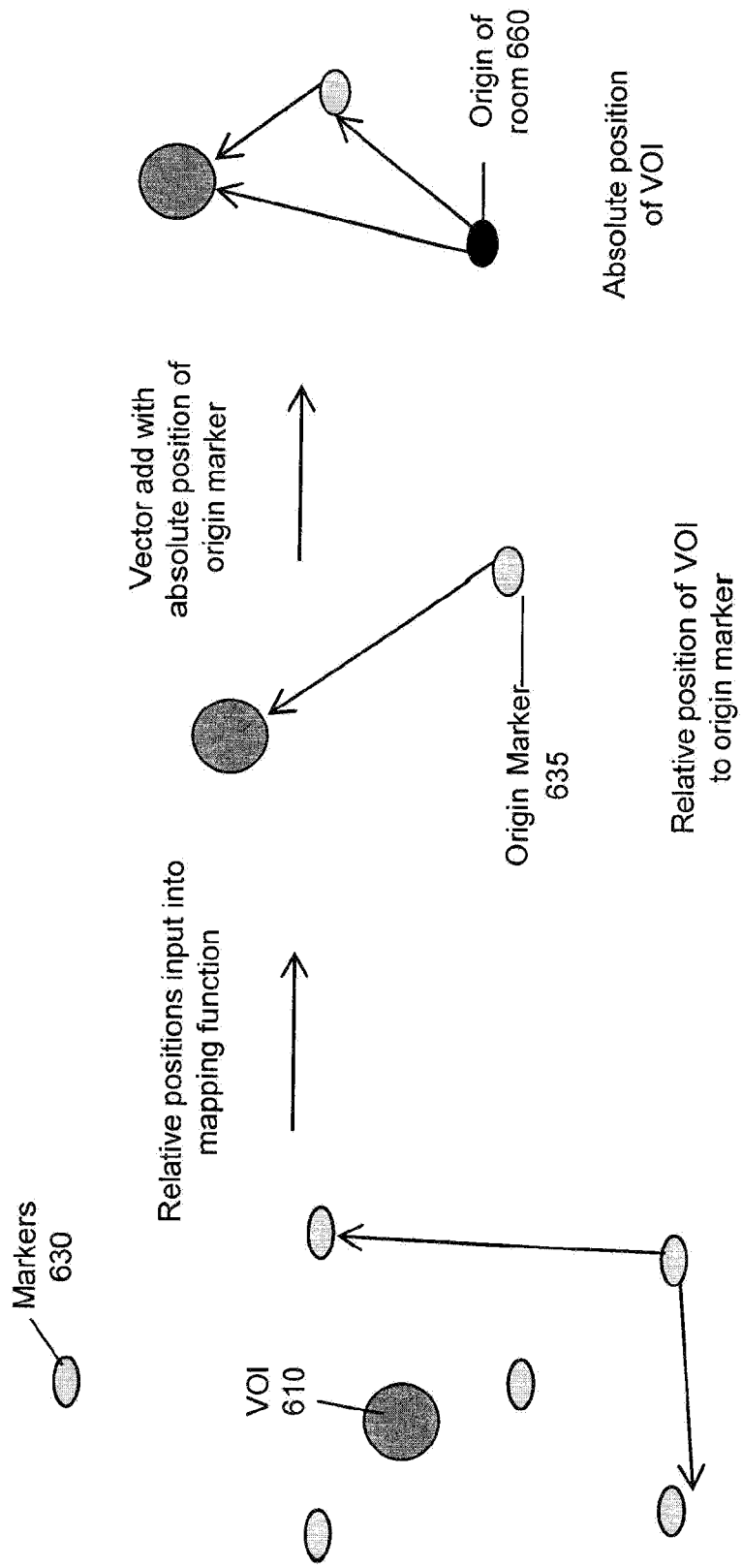

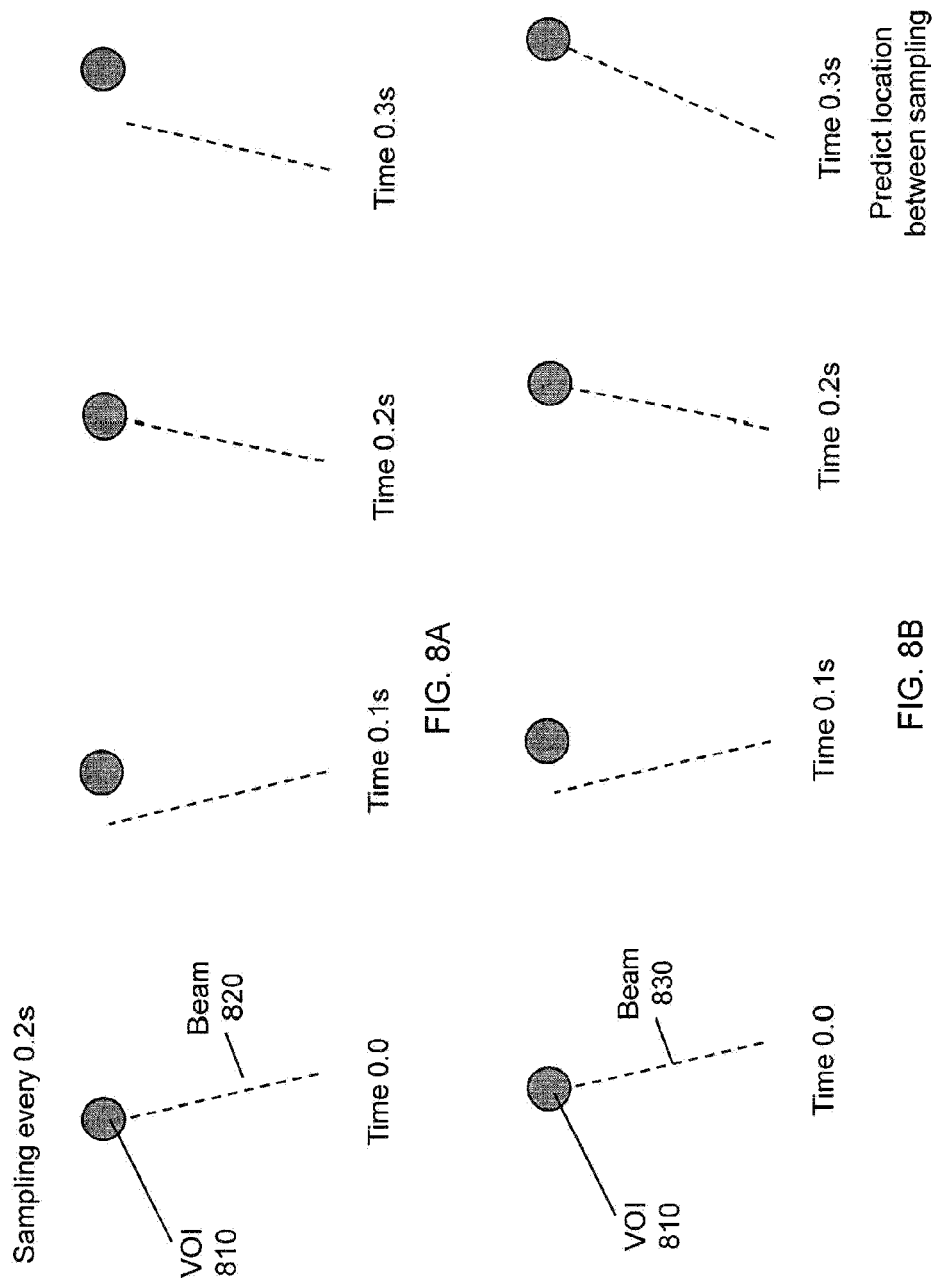

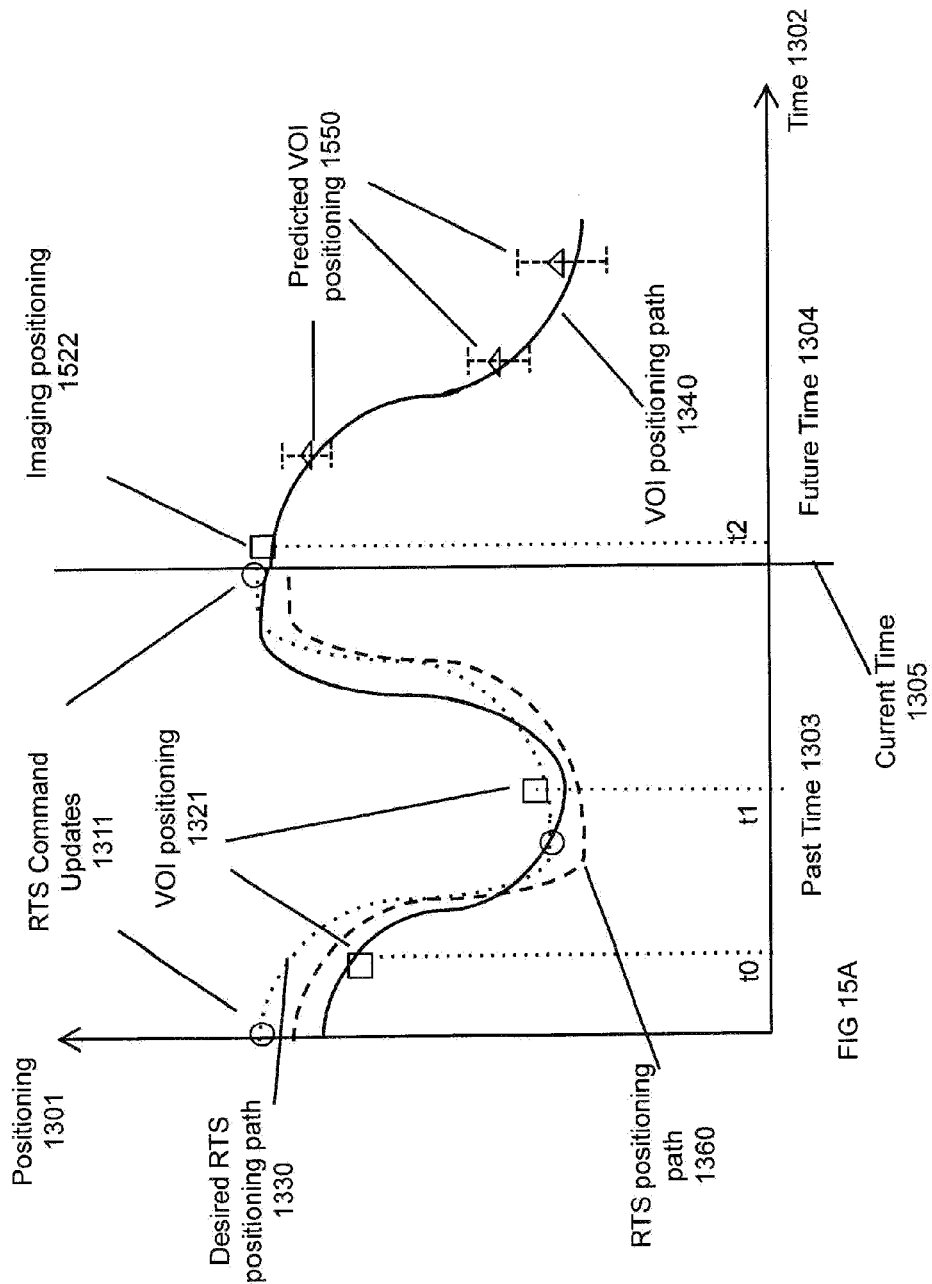

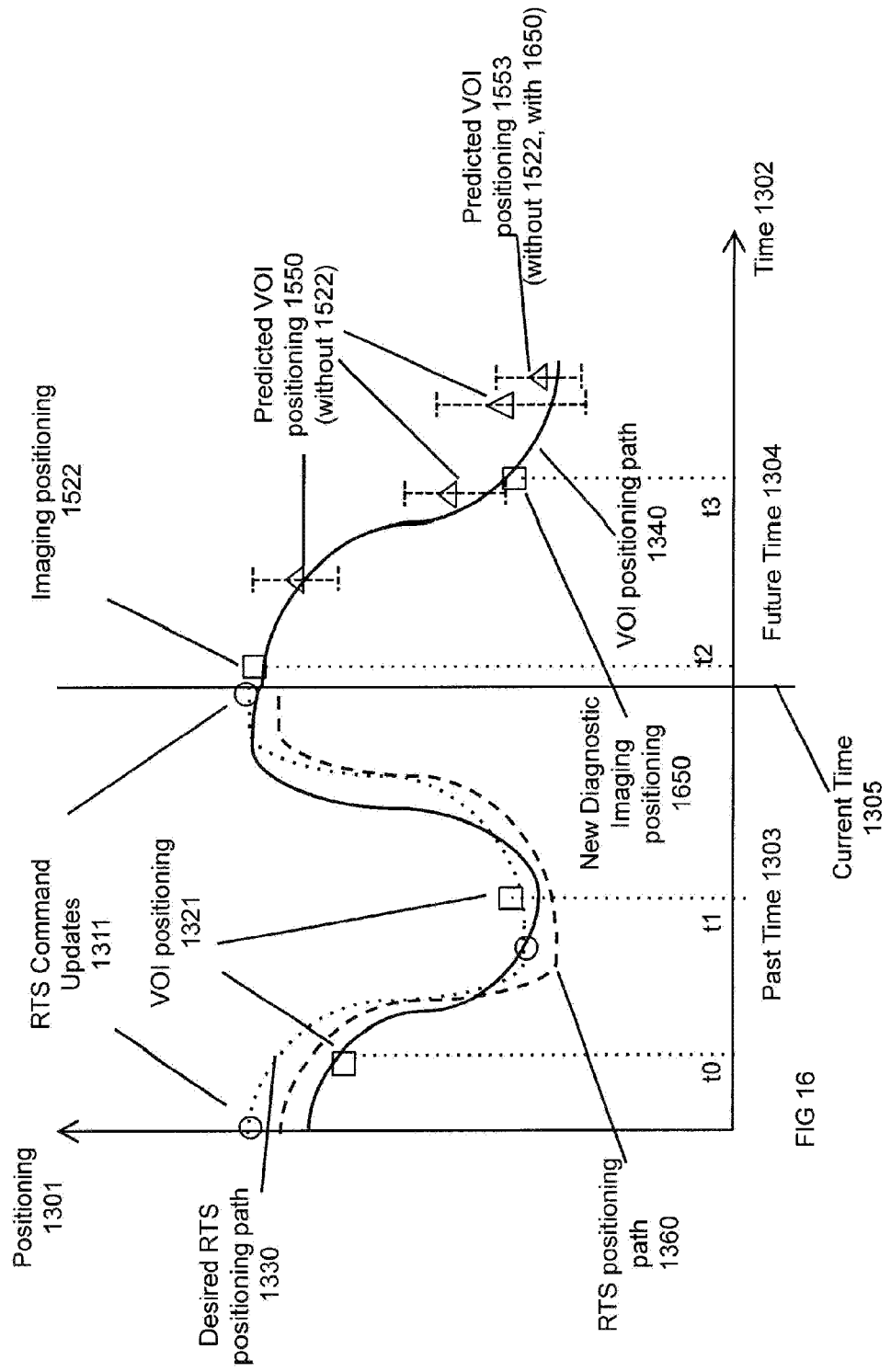

RADIATION TREATMENT WITH MULTIPLE IMAGING ELEMENTS

CROSS-REFERENCES TO RELATED APPLICATIONS

The present application is a continuation-in-part of U.S. patent application Ser. No. 13/356,601, titled "Tracking of Tumor Location for Targeted Radiation Treatment", filed on Jan. 23, 2012, which claims priority from and is a non-provisional application of U.S. Provisional Application No. 61/435,195, entitled "Non-Invasive Tracking of Tumor Location for Targeted Radiation Treatment" filed Jan. 21, 2011, the entire contents of which are herein incorporated by reference for all purposes.

FIELD OF THE INVENTION

The described embodiments relate to radiation treatment. More specifically, the described embodiments relate to radiation treatment with multiple imaging elements.

BACKGROUND

Radiation beams have been used to treat (for example necrotize) diseased tissue (e.g. a tumor). However, the radiation beam can also damage healthy tissue. Thus, methods have been used to determine a location of a VOI so that the radiation beam can be focused on a VOI or other diseased tissue. For example, the radiation beam can move over time to minimize exposure of healthy tissue while staying focused on the VOI. An x-ray can be taken at the beginning of the treatment for positioning markers (for example sensors, fiducials or other marking objects) that have been surgically placed on the VOI, thereby providing the location of the VOI. This invasive method is costly and can be dangerous to the patient.

Some methods restrict a patient to a specified position for the duration of a treatment so that the position of the VOI stays known. Such restriction can be quite uncomfortable for the patient, and errors can occur due to imperfect restriction. Methods can take repeated x-rays of internal markers to update the position of the VOI while breathing, but such methods expose the patient to a large amount of radiation via the numerous x-rays or require the motion to be periodic. Methods can omit the implantation of markers (for example fiducials) by correlating a location of certain bones, which tend not to move during treatment, to the VOI location. But, the patient is still restricted to a particular position, or at least a particular orientation (e.g. tying flat on one's back). These methods also still suffer from numerous x-rays if the location of the VOI is to be updated.

U.S. patent publication 2008/0212737 omits the numerous x-rays during treatment and the implantation of markers (for example fiducials) while still accounting for the movement due to breathing; however, the patient is still restricted to certain positions. For example, the patient is restricted to lying on his/her back on a special table while being held in place. A scan is performed at different times during the breathing cycle, with each time in the breathing cycle corresponding to a distance in positions of a marker on the patient's chest compared to a marker in the special table. The scans can then be used to determine a location of the VOI during radiation beam treatment, but the location is accurate only when the person is in the same exact location as when the scans were taken. Thus, although procedure is non-invasive and limits excessive radiation scans during treatment, the person is still confined and uncomfortable during treatment. Furthermore, this application only handles small periodic motion such as breathing. Different positions of the patient are not allowed.

Additionally, the equipment for creating the radiation beam must be precisely calibrated so that a control input corresponds to the exact location where the VOI is determined to be. The equipment must be made with very high tolerance so that the control inputs correspond the proper beam placement. Thus, the beam equipment can be very expensive. Additionally, current techniques do not properly handle beam positioning error.

Therefore it is desirable to have improved systems and methods for providing targeted radiation treatment that can variously allow a patient freedom of movement without excessive radiation, are easy to use, do not require difficult calibration, are non-invasive, allow movement beyond simply breathing, and compensate for beam positing error and other systematic errors in the system.

SUMMARY

An embodiment includes a system. The system includes first imaging element configured to generate a first observation of a first object, the first observation of the first object being generated at a first time, wherein the first object is associated with a volume of interest (VOI), wherein the VOI is a volume within a body of a patient. The system further includes a second imaging element configured to generate a first observation of a second object, wherein the first observation of the second object is generated at a second time, and the second object is associated with the VOI. The system further includes one or more processors configured to determine first positioning of the VOI based at least in part on the first observation of the first object and the first observation of the second object, determine a third time for the first imaging element based at least in part on a positioning parameter associated with the first positioning of the VOI, and generate a second observation of the first object at the third time.

Other embodiments are directed to systems, apparatuses, and computer readable media associated with methods described herein.

Reference to the remaining portions of the specification, including the drawings and claims, will realize other features and advantages of the described embodiments. Further features and advantages of the described embodiments, as well as the structure and operation of various embodiments of the described embodiments, are described in detail below with respect to the accompanying drawings. In the drawings, like reference numbers can indicate identical or functionally similar elements.

BRIEF DESCRIPTION OF THE DRAWINGS

FIG. 4 shows a diagram of a patient undergoing treatment according to at least one embodiment.

FIG. 5 shows an origin marker 535 from which the relative positions of the markers are determined according to at least one embodiment.

FIGS. 6A-6C shows the relative coordinates of the markers being used to determine the location of the VOI location according to at least one embodiment.

FIG. 8A shows an intermittent error in beam positioning due to movement of a VOI 810 according to at least one embodiment.

FIG. 8B shows an example of a prediction of a location of a VOI between sampling times according to at least one embodiment.

FIGS. 15A, 15B illustrate a method for and adaptive (for example reducing) imaging of an image guided radiation treatment system according to an embodiment.

FIG. 16 is an illustration of another image guided radiation treatment system according to an embodiment.

DETAILED DESCRIPTION

I. Introduction

The described embodiments relate to targeted radiation treatment (for example radiosurgery or radiotherapy), and more specifically to techniques of determining a location of a volume of interest (VOI) (which may include one or more of a target, a tumor, a tissue, a target tissue, a diseased tissue and a healthy tissue) of a patient for determining a radiation treatment system configuration (for example a radiation beam configuration or a patient couch configuration).

Figure 1A:
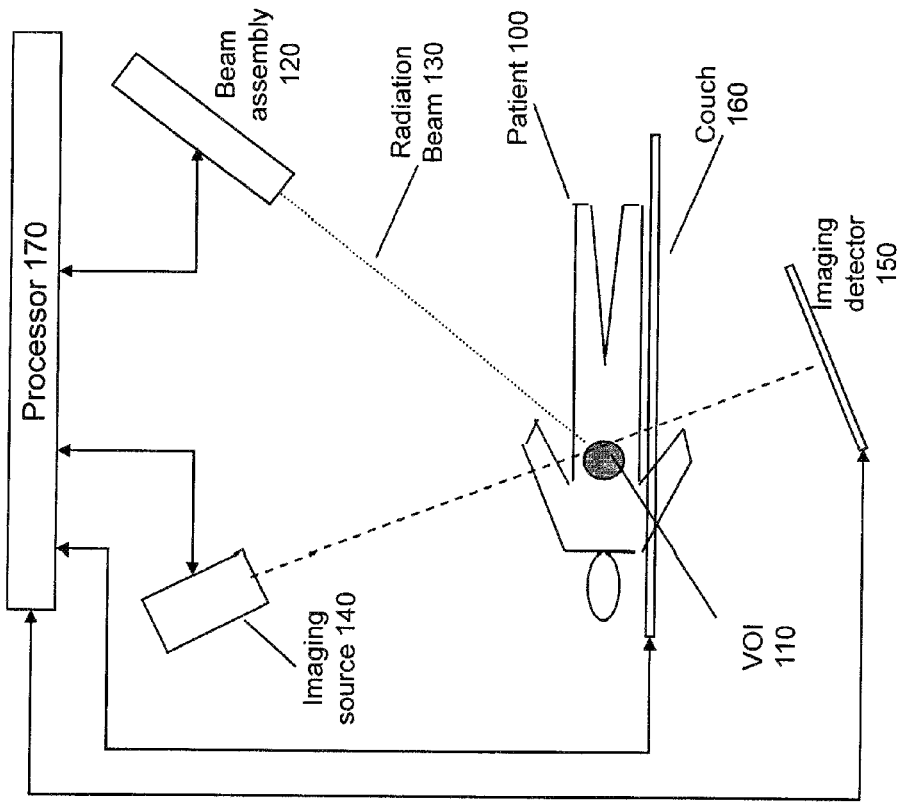
FIG. 1A shows a diagram of a patient 100 undergoing radiation beam treatment according to at least one embodiment.

FIG. 1A shows a diagram of a radiation treatment system, according to at least some embodiments. Radiation treatment system comprises one or more radiation treatment system elements, such as of a patient 100, VOI 110, beam assembly 120, radiation beam 130, patient table or couch 160, imaging element (or imaging element) which may include one or more of imaging sources 140, one or more imaging detectors 150, one or more markers (sources, reflectors, absorbers, attenuators, emitters, transmitters, receivers, etc.), a processor 170 (or alternatively a computer, server, etc.). In some embodiments a mechanical couch 160 is provided as part of the radiation treatment system such that under the control of the processor 170 the relative positioning of the mechanical couch and a radiation treatment system element (for example the radiation assembly or radiation beam) may be varied. In some embodiments the positioning the patient 100 relative to one or more radiation treatment system elements may be varied. In some embodiments delivery of radiation beam is modified relative to a radiation treatment system element (for example the couch 160 or patient 100 or VOI 110). In some embodiments radiation beam modification options include one or more of administering the dose, refraining from administering the dose, re-positioning the patient, redirecting the radiation beam, and modifying the radiation beam size or shape or intensity.

In some embodiments radiation beam modification options include one or more of beam intensity, beam width, beam shape, beam orientation, beam trajectory, beam multi-leaf collimator (MLC) settings of the beam assembly 120, beam properties relative to a VOI 110 or a patient 100, positioning of a patient couch 160 relative to the beam 130, positioning of the patient 100 or VOI 110 relative to the beam properties, etc.

The patient 100 is shown as laying down on his/her back on couch 160, but other body positions and/or orientations are allowed. A beam assembly 120 is shown in a particular orientation to provide a radiation beam 130 that is focused on a VOI 110 inside patient 100. Beam assembly 120 can be connected to a movement mechanism that allows beam assembly 20 to be moved. For example, beam assembly 120 can be part of a robotic mechanism that sits on a floor of a room, is attached to a wall, or hangs from a ceiling. For example beam assembly 120 may be part of a circular gantry (C-arm or ring), that allows the radiation beam 130 to be positioned at an angle within the ring or rotating G-arm.

In one embodiment, beam assembly 120 may be moved during treatment so that healthy tissue is not irradiated for too long. For example, if the beam always had the same trajectory, the tissue above the VOI 110 would continuously be exposed to radiation. If the beam assembly moved while staying focused, the same healthy tissue would not be continuously exposed.

In order to stay focused on the VOI 110, the location of VOI 110 needs to be known. This is true regardless of whether beam assembly 120 moves during treatment or not. Embodiments can provide non-invasive techniques for determining a location of VOI 110 while allowing a patient to be in different physical positions. For example, some embodiments perform an imaging scan prior to treatment. The term 'imaging scan' may be exchanged by the alternative terms 'imaging' or 'scan' or 'imaging observation' throughout.

Figure 1B:
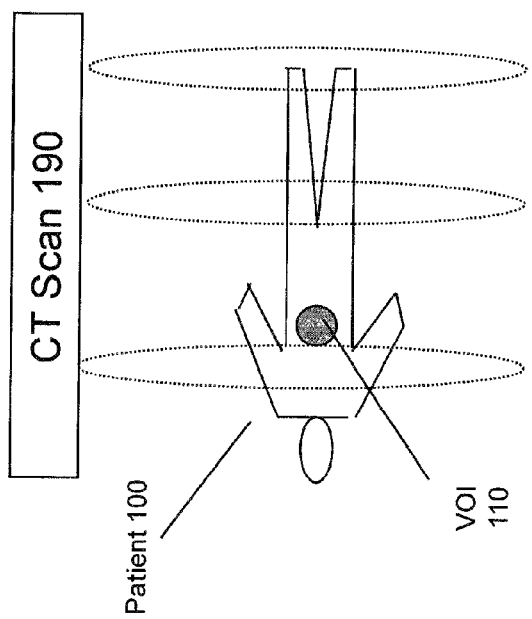
FIG. 1B shows a diagram of a patient 100 undergoing an imaging scan according to at least one embodiment.

FIG. 1B shows a diagram of the patient 100 undergoing an imaging scan according to at least one embodiment. FIG. 1B is shown on the left of the page to illustrate that this imaging is performed before the treatment. The scan can be in a different room and be done on a different patient visit than the treatment. In another embodiment, the room for scanning can also be used for treatment. In some embodiments, the patient pre-treatment visit can be on the same day. In the embodiment shown, a computed tomography (CT) scan is used, but other suitable imaging may be used, such as magnetic resonance imaging (MRI), ultrasound, cone beam computed tomography (CBCT), positron emission tomography (PET), etc. These accurate scan(s) of the patient and WA can provide coordinates of the VOI relative to markers attached to the patient's body. Such a method is now described.

II. Using Mapping Model

Figure 2A:
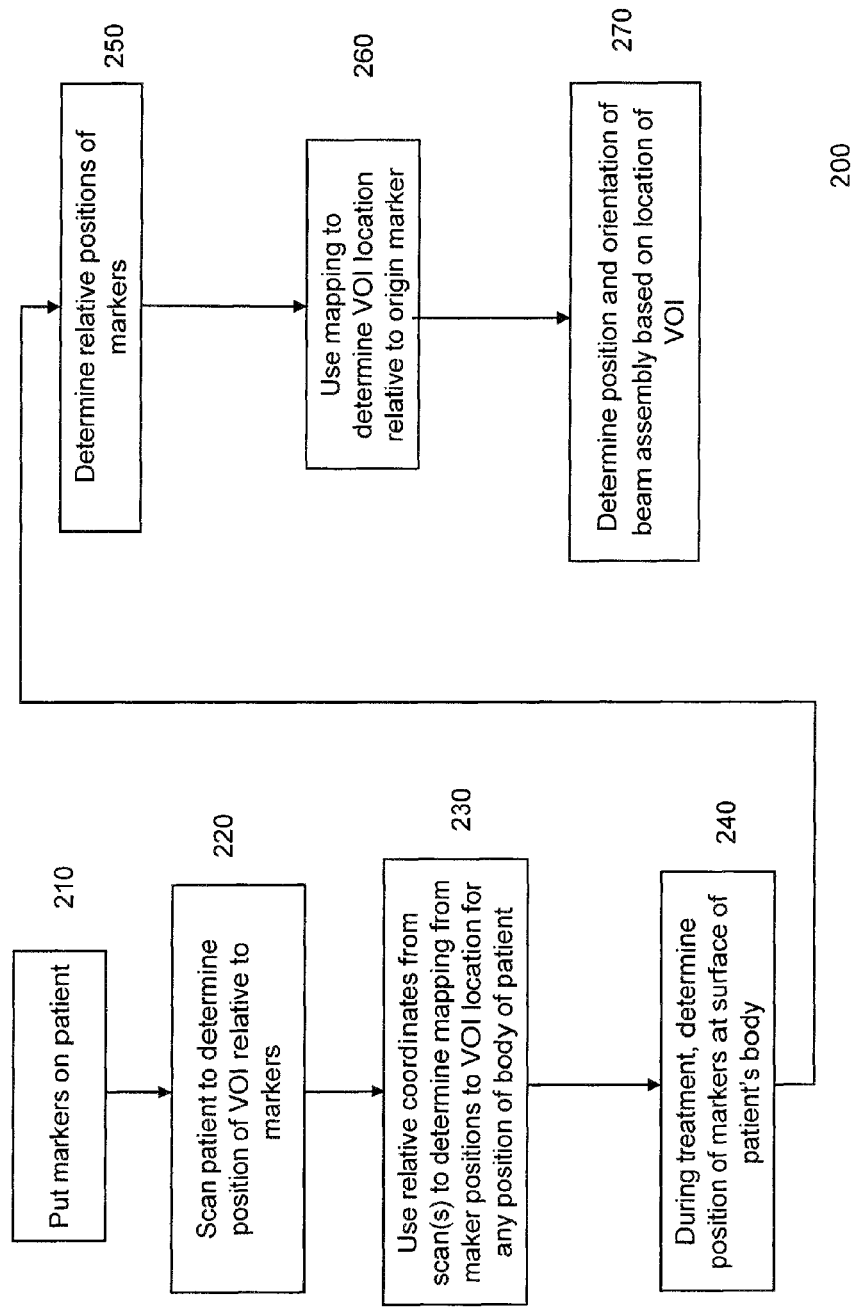
FIG. 2A is a flowchart of a method 200 for determining a location of a VOI (e.g. a tumor) according to at least one embodiment.

FIG. 2A is a flowchart of a method 200 for determining a location of VOI (e.g. a tumor) according to at least one embodiment. In one aspect, method 200 uses one or more imaging scans (such as MRI or CT) to develop a 3D model of the location of the VOI for different physical positions of the patient. The physical positions of the patient can be defined using markers at a surface of the patient's body. Sensors at these marker positions (or at a defined position relative to the marker positions) can be used to determine the physical position of the patient's body during treatment.

In step 210, a plurality of markers is placed at a surface of the patient's body. The markers may be any object (e.g. ink, sensor, pellet, tag, etc) whose position can be detected during a scan of the patient. In one embodiment, the mechanism for detecting the marker position can be the same mechanism for the scan of the VOI (e.g. MRI), and thus the coordinates of the markers are in the same reference frame as the coordinates of the various tissue that is obtained in the scan. For example, the markers can show up in the imaging scan. In another embodiment, some other mechanism (e.g. an RF signal or an optical signal) can be used to determine the coordinates of the markers, and the two coordinate systems of the scanned VOI and the markers can be merged such that relative positions between the markers and the various tissues can be determined.

Figure 3B:
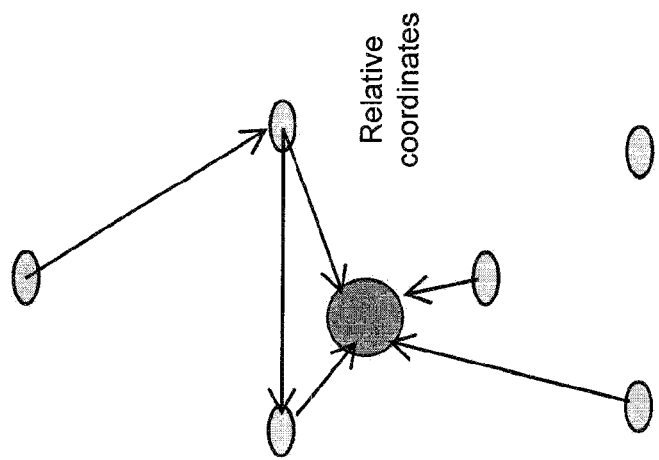
FIG. 3B shows the relative coordinates of markers 320 compared to VOI 310 according to at least one embodiment.
Figure 3A:
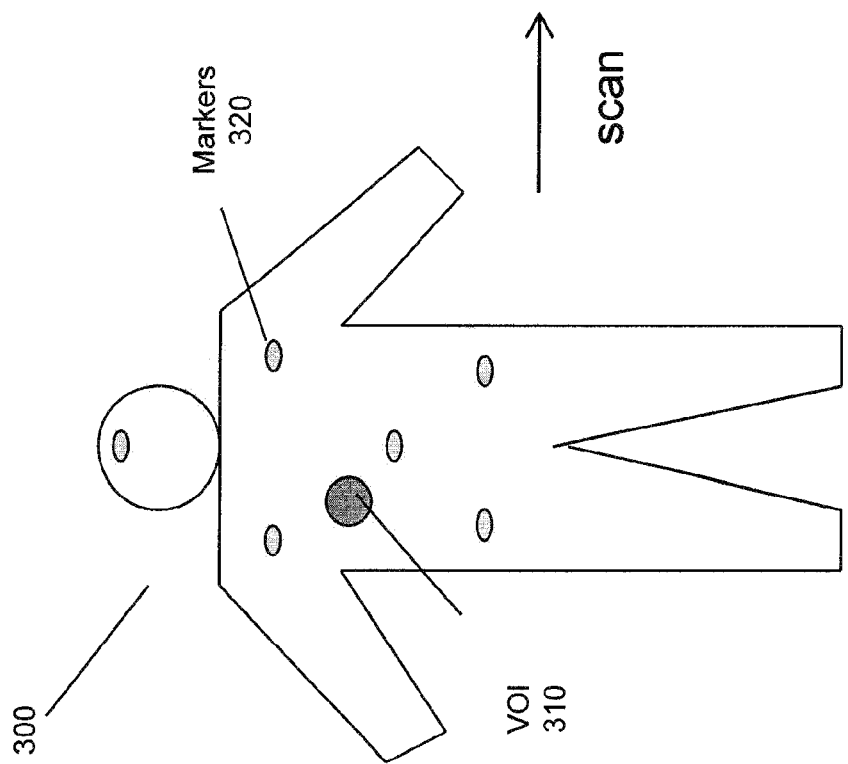
FIG. 3A shows a patient 300 with markers 320 according to at least one embodiment.

FIG. 3A shows a patient 300 with markers 320 at a surface of the patient's body. The markers 320 can be on the front or back of the patient, head, appendages, or at any other surface of the patient's body. In some embodiments, only one or two markers may be sufficient. In other embodiments, a larger number of markers may be used. The markers can be attached or otherwise put on the patient via any suitable manner, such as adhesives, mechanical attachment to or at a surface of the skin, or just as a layer that binds to the skin. The different makers 320 can be distinguished based on the known locations where the markers were placed, by a unique signature that identifies the marker in a scan, or in any other suitable manner.

The markers can also be identifiable features of a person's body, such as an elbow, a nose (even just the tip), a nipple, belly button, shoulder, etc. The markers can be identified using cameras, such as a typical camera operating with visible light, or other ranges may be used in addition or instead, e.g., infra-red and/or ultraviolet. Thus, artificial markers do not have to be placed on the body, since natural body markers can be used. Natural and artificial markers can be used in combination.

In addition to the identifiable markers on a surface of a body, internal markers could be used, as long as the locations of the markers could be accurately and efficiently identified during treatment. For example, x-rays or ultrasound could detect a position of a particular location on, for example, the spine or femur for the leg, or even soft tissue (which could include the VOI). However, such methods could present difficulties in resolving precise locations of a bone. Such internal markers may provide supplementary information to the positions of the external markers, e.g., in order to refine the mapping model during treatment. For imaging soft tissue during treatment, the accuracy may be low, but some rough values (e.g. located by with larger margins of accuracy than a marker location) can be obtained. A distance or distance range of the VOI from the markers (which can be internal markers) can then be compared to the mapping model to ensure that the mapping model is accurate, and to possibly update the mapping model (e.g. using a best-fit algorithm). The best-fit can determine the maximum likelihood of the VOI location based on the additional scan (i.e. the scan during treatment), which can provide a location of clear internal markers (such as bones), external markers, and a fuzzy location of any one or more soft tissue (which can include the tumor or healthy tissue), along with information from the more accurate pre-treatment scan. In one aspect, the mapping model update may be performed when the mapping model is shown to be inaccurate from the best-fit model.

In step 220, the patient is scanned to determine the positions of VOI (e.g. diseased or healthy tissue) relative to the markers. For example, the absolute positions of the VOI and the markers can be determined in a particular reference frame. Scans can choose any coordinate system (e.g. Euclidean, spherical, etc.) with an arbitrary origin. The absolute coordinates of the VOI and the markers can then be determined in this coordinate system. For example, the coordinates of VOI 310 and of markers 320 can be determined.

In some embodiments, multiple scans can be performed at different body positions, as is described in more detail below. Each scan can provide a different set of relative coordinates. A set of relative coordinates for a particular scan can provide a multi-dimensional point defining a location of VOI 310 for a particular physical position of the patient during a scan. The various physical positions can include sitting upright, laying down, standing, and sitting in a reclined position.

In step 230, the relative coordinates from the one or more scans are used to determine a functional model that maps marker locations to a VOI location for a physical position of the patient. In one embodiment, the functional model receives information for the relative coordinates of the markers as input and provides an output of the location of the VOI. The input locations are not restricted to the relative locations in the one or more scans that were performed, but can be other relative locations that correspond to other physical positions of the patient. For example, intermediate positions may be between laying on a side and laying on aback. The functional model can be created in various ways. In one embodiment, the functional model can have constraints, e.g., some physical positions (relative coordinates) may be rejected if they appear to deviate drastically from normal physical positions (e.g., a rejection of a contortionist body position).

FIG. 3B shows the relative coordinates of markers 320 compared to VOI 310. In various embodiments, the relative coordinates can be to a center of mass of the VOI, center of volume of the VOI, or each to a particular point on a surface of the VOI (e.g. the closest point on the surface relative to a particular marker). The relative coordinates of the markers to each other can be determined from the relative to the VOI, or from the absolute coordinates of the markers themselves.

Figure 3D:
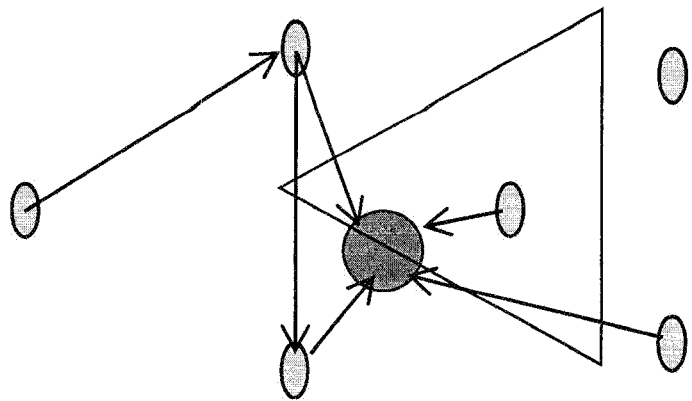
FIGS. 3C and 3D show a reference object 370 that may be used during a scan of a patient according to at least one embodiment.
Figure 3C:
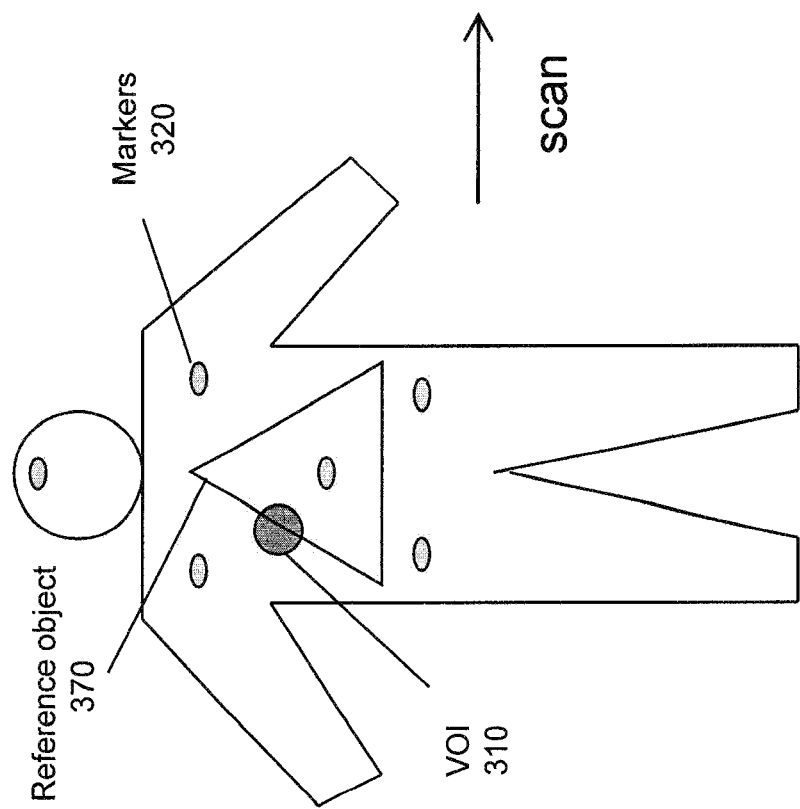

Other objects besides the markers may also be placed at the surface of the patient's body. FIGS. 3C and 3D show a reference object 370 that may be used during a scan of a patient according to at least one embodiment. The reference object 370 is shown as a triangle but any shape may be used. The reference object is of a known dimension and its position can be determined in the same manner as the markers. With the known dimension, the distances between the markers can be verified, calibrated, and/or corrected. For example, a length on the image can be obtained from the reference object, and this length can then be used to obtain the proper scale in the image, which would provide the accurate length between two markers. In one aspect, the relative coordinates would be scaled based on the reference scale provided by the reference object to provide more accurate relative coordinates and relative vectors between the markers.

In other embodiments, a distance of the markers can be measured by hand or some separate mechanism to provide the reference distance. Thus, the reference object could include the markers, e.g., a specific set of markers whose pair-wise distances can be measured. The reference object could also include other marks whose relative distance to the VOI is not used, but whose positions are measured to provide a reference scale for the image. The reference object can be made up of any number of pairs of such marks to provide a reference scale in numerous directions, which can account for variable distortion along different directions.

In some embodiments, more than one reference object may be used. The different reference objects can be used to provide a reference scale in multiple directions. For example, a reference object could be placed on the patient's side, thereby providing a reference scale for depth, which can provide corrections that are different than the corrections obtained from a reference object on the patient's torso (which may just provide a reference scale for width and height).

In step 240, markers are attached to the patient's body and positions of markers are determined. For example, the markers can be placed at a surface of the patient's body, or possibly surgically implanted within the patient's body for some embodiments. The positions of the markers can be determined with respect to a reference point having a known spatial relationship to a beam assembly (e.g. beam assembly 120), which is configured to provide a radiation beam. The markers may be wireless (e.g. optical, infrared, etc.), or be wired. In other embodiments, natural markers (such as facial features, or even bone features, as is described herein) may be used as the markers, and thus new artificial markers do not need to be attached.

The position of the markers can be determined (e.g. sampled) at periodic intervals to track movement of the patient from one position to another position. In one embodiment, the sensors can be at a same location as markers, or simply be the markers. In another embodiment, a sensor can be at a location that is at a predetermined offset from the location of a marker.

In one embodiment, the markers are placed on a surface of the patient. In another embodiment, the markers are placed slightly below a surface of the patient's body. Both locations correspond to being at a surface. Similarly, the markers can be placed at a surface of the patient. The sensors can be placed at a same location as the markers. In one implementation, this can be accomplished with a semi-permanent mark (which can be the marker) so that the location of the sensor can be known. The semi-permanent marker can be made to last for the duration of the treatment, which can be anywhere from a day to one week or a month, or longer.

FIG. 4 shows a diagram of a patient undergoing treatment according to at least one embodiment. Wireless elements 430 are at a surface of the patient's body. The positions of the wireless elements 430 can be determined from detectors 440, which may be connected to a computer system. The wireless elements can implement any suitable technology, such as Zigby, Bluetooth, optical/laser technology etc. For optical markers, their position can be determined from a reflection of radiation (e.g. visible light) off of the wireless elements 430. An optical marker can even be a particular body feature, e.g., as identified by a recognition algorithm that analyzes a picture of the patient, which may be performed using two or more digital cameras. The pixel positions of the optical marker on the images from the cameras can be correlated to a particular 3-dimensional spatial coordinate, e.g., using triangulation. The correlation (mapping) may be performed using a best-fit algorithm. The mapping can be calibrated with known reference objects (which may be of known shape) at known distances, e.g., within a treatment enclosure. Such known objects could be flashing or include an active marker (for example a sensor), which may be used to independently confirm or calculate the location of the known reference object. Thus, the sensor can be the marker used in step 210, including internal markers.

The detectors 440 can be used to triangulate the positions of the markers relative to an origin of the room. For example, the detectors 440 can each be at a known position, and thus at known positions relative to each other. The signals from each detector can then be compared to determine the position of a marker. Again, any coordinate system can be chosen, and the origin is arbitrary. In one implementation, the detectors 440 can be calibrated by measuring the relative distances of markers that have a known spatial relationship.

Embodiments can use various methods to determine the positions of the markers, such as GPS positioning technology, optical imaging of the marker locations, and passive or active wireless communication devices. In one embodiment, the markers could receive signals and then transmit location. In another embodiment, the markers could transmit signals (for example an LED or a wireless transmitter) and detectors 440 can determine the location. In another embodiment, the markers could reflect signals and detectors 440 can determine the location. In another embodiment, the markers could reflect or attenuate (for example an x-ray opaque marker) an imaging source signal and detectors 440 can determine the location. In one implementation, the markers each have a unique signal so that the markers can be distinguished.

In step 250, positions of the markers relative to each other are determined from the determined positions of the markers in the treatment room. In one embodiment, the relative coordinates can be defined with respect to one of the markers, which can be taken as the origin in the relative coordinate system. Thus, in one embodiment with N markers in a 3-dimensional environment, N−1 relative positions (each with 3 coordinates) can be determined, where the positions are relative to the origin marker. In this case, $3*(N-1)$ relative coordinates would be determined. For example, since there are N−1 markers besides the origin marker, there will be N−1 relative positions, and $3*(N-1)$ relative coordinates.

FIG. 5 shows an origin marker 535 from which the relative positions of the markers are determined according to at least one embodiment. Note that the relative marker positions can also be measured from an origin marker, and thus the sets of relative positions of markers can be used as input to the functional model. Beam assembly 520 and detectors 540 can function as described herein.

In step 260, the relative coordinates are input into the mapping model to determine the VOI positioning. In one embodiment, the VOI location can be defined relative to an origin marker. A position relative to the origin marker can then be translated to an absolute position in the treatment enclosure (e.g., the room or smaller containment unit that is meant to house the body), given the location of the origin marker. For example, the position of the origin marker can be with respect to a reference point (e.g., an origin of the treatment enclosure). Thus, absolute position can be obtained, where the absolute position is with respect to the reference point.

FIGS. 6A-6C shows the relative coordinates of the markers being used to determine the location of the VOI according to at least one embodiment. FIG. 6A shows the relative coordinates of the markers 630 at a particular instant in time. The arrows show a vector defining the relative coordinates. Only two relative coordinates are shown, purely for illustration purposes.

The relative coordinates are fed into the mapping model to provide the location of the VOI 610 as defined from the origin marker. FIG. 6B shows the resulting relative coordinate vector providing the VOI location relative to the origin marker 635. FIG. 6C shows the position the VOI location relative to an origin 660 of the treatment enclosure (e.g. a room). As shown, the VOI location is obtained as a combination of position of the origin marker and the relative coordinate of the VOI. Thus, in some embodiments, the VOI location can be determined just from the markers, and without prior knowledge of the location of the VOI in the room or relative to a stationary object in the room.

In step 270, the location and/or orientation of the beam assembly is determined based on the location of VOI. The coordinate location and/or orientation (e.g. angular orientation) of the beam assembly can define the trajectory of a radiation beam being emitted from the beam assembly. Since the position of the beam assembly with respect to the reference point is known, and the position of the VOI with respect to the reference point is known, one can determine the positioning of the beam assembly (or any other beam parameter such as shape, trite, intensity) or positioning of the patient or positioning of the patient couch (or other patient furniture) that directs the radiation beam to be focused on the VOI. Other factors, such as the location of healthy tissue, can be used to select an optimal location and/or orientation, such that the beam follows an optimal path. In one embodiment, one or more markers (which may be one or more of sensors, transmitters, receivers, optical markers) can be used to determine the location and/or orientation of beam assembly so that the beam stays focused on the VOI, even while the beam assembly is moving so as not to damage healthy tissue.

In one embodiment, locations of healthy tissue are also determined. For example, it may be desired to provide none or minimal radiation to certain organs, e.g., the heart. The locations of these particular organs that can receive none or minimal radiation may be used to determine the proper beam trajectory.

The radiation treatment may be provided in any suitable treatment enclosure, such as a room or a self-contained module. For instance, a capsule (e.g., cylindrical or rectangular can include the beam assembly and a mechanism to move the beam assembly. For example, the treatment enclosure can have a vertical or horizontal orientation, with the beam assembly being on a support (e.g. a bar) along the long axis. The bar can then rotate around the patient, for example, to provide a cylindrical coverage of the patient. The beam assembly can also have angular degrees of freedom, e.g., the beam can be tilted up and down and side to side. Multiple beam assemblies could be provided on a same support, and there can be multiple supports with different beam assemblies. A small treatment enclosure (particularly if it is self-contained with the beam assembly and detectors, such as cameras or an x-ray device) can facilitate calibration and provide greater accuracy. In one embodiment, the treatment enclosure can also be used in pre-treatment scanning to create the mapping model, or to supplement a previously obtained mapping model.

Figure 2B:
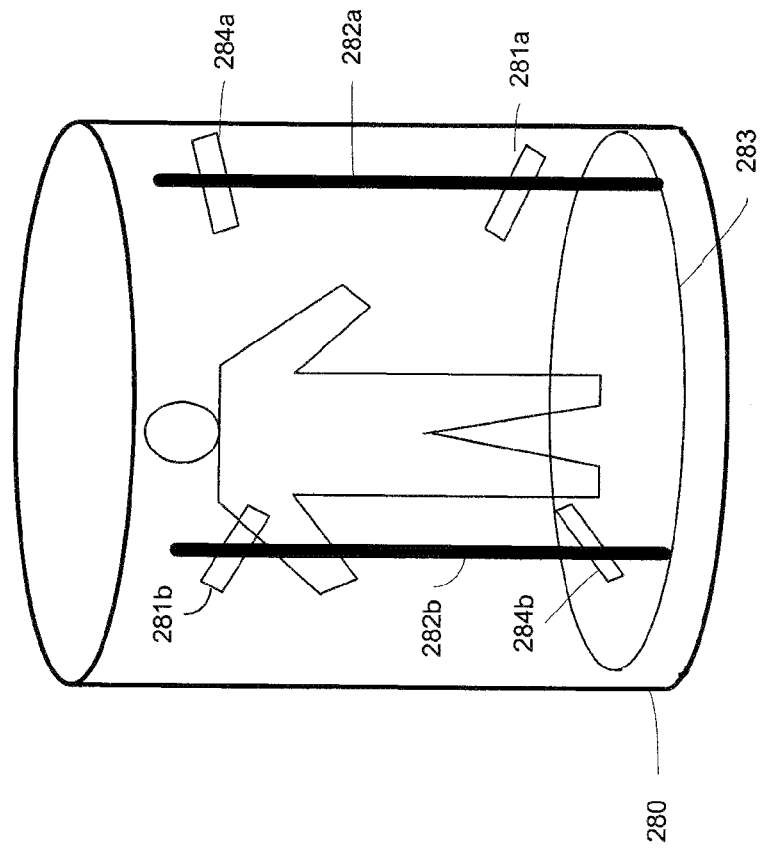
FIG. 2B shows a treatment enclosure 280 according to at least one embodiment.

FIG. 2B shows a treatment enclosure 280 according to at least one embodiment. The enclosure 280 can be of any shape, and may surround only part of the patient, e.g., just a torso. As shown, the patient is standing, but the patient may be in any position (e.g. leaning against a central object, sitting, or lying down). When lying down, enclosure 280 can have the long axis horizontal. Enclosure 280 can be made with a door for a patient to walk through, or in a horizontal mode a bed can slide in and out from one end of the enclosure. Beam assemblies 281a and 281b can be mounted to supports 282a and 282b. As shown, there are two supports, but other embodiments can have one support or more than two supports. The supports 282 can move on a track 283, which can be near either or both ends of enclosure 280. As shown, track 283 is circular, thereby allowing the supports to rotate. In some embodiments the beam assemblies 281a and 281b can rotate, and are shown rotated from horizontal (up and down and rotated from vertical (left and right). In addition to the beam assemblies, imaging devices 284a and 284b may be attached to supports 282 or to other support structures, such as an inner wall of enclosure 280. These imaging devices can include, for example, x-ray machines, optical cameras (e.g., in the visible and/or infrared spectrum), radio frequency receivers to receive signals from active markers, or any other suitable imaging device.

III. Using-Multiple Scans of Same Patient

As mentioned above, the patient can be scanned prior to treatment, in order to determine a function that maps marker positions to the location of VOI (for example diseased and/or healthy tissue). In some embodiments, multiple scans of the same patient can be used to determine the mapping model.

In one embodiment, each scan corresponds to a different physical position of the body. Each scan can provide the positions of the markers and of the particular VOI (e.g. a tumor). Thus, for N markers, each scan can provide $3*(N-1)$ values, which can be considered as a multi-dimensional data point. An analogy to a simple two dimensional data point $(X,Y)$ as determined by a function $Y=f(x)$ is that the coordinates of the markers are the input values X, and the location of the VOI is the output Y.

In some embodiments, coordinates of the markers can be measured from any origin, e.g. a marker can be considered the origin. Thus, $3*N$ values may define the multi-dimensional data point in the relative coordinate system, with $3*(N-1)$ values for the non-origin markers and 3 for the VOI location relative to the origin marker. In one embodiment, certain markers may be discarded if the dependence of the VOI location on the marker position is flat. For example, a change in the marker position would not affect the VOI location. In this manner, the best or most informative markers can be used.

In one embodiment, the data points can be interpolated, curve fit, etc. to determine a surface that maps the relative coordinates of the markers (e.g. relative to the origin marker) to the relative coordinate of the VOI. In various embodiments, the relative coordinate of the VOI can be defined as a center of mass, center of volume, or other average value related to the VOI.

In another embodiment, the shape of the VOI, as determined from scan(s), can be superimposed onto the VOI coordinate. In one implementation, changes in the shape and/or orientation of the VOI can also be determined as outputs to a functional model. For example, the orientation can be computed as a separate mapping, as defined by one or more parameters, such as the three Euler angles.

IV. Using One Scan of Current Patient

In some embodiments, only one scan (or just a few) of the patient may be required. The (problem becomes how to obtain changes in the VOI location with changes in physical position when only one physical position is obtained. In one embodiment, specific scans or scan information from other patients are used. The functional model can then be obtained using a combination of the one scan for the specific patient and the scan information from one or more other patients, e.g., having similar body shape, gender, age, height, width and/or body mass. In this manner, the number of scans for a particular patient can be reduced, and the one or more scans from other patients can be re-used, thereby reducing a total number of scans needed, or providing greater accuracy.

In one embodiment, markers are placed at the same locations for control patient(s). In one embodiment, the locations are defined with respect to one or more natural markers, for example certain body parts, belly button, between eyes, top of spinal cord, etc. As an alternative, natural markers that have a fixed relationship to each other can have substituted for placement of one or more artificial markers. The markers can then be placed at a same location on the current patient.

In one embodiment, the control patients are the same body type as a current patient. For example, control patients of various types may be used, with information from patients with a similar body type being used in combination with the scan of the current patient.

In one implementation, a mapping model can be determined for each control patient. The mappings for different control patients can then be averaged together. In another implementation, the various scans can define data points across patients, and a single mapping can be determined. In one aspect, the data points can be grouped by the patient and then scaled prior to combining to form the single mapping. Accordingly, in one embodiment, a general mapping model is determined from the control patients. If body type (e.g., male, female, overweight, athletic, pear-shaped, muscular, etc.) is accounted for, embodiments can have different mapping model for each body type, Control groups can also be organized by the location of VOI e.g., which organ has the VOI.

The single (or simplified) scan for the current patient can be used as a scalar on the mapping from the control patient group. For example, the size of the mapped surface (i.e. a surface that defines the VOI location in the multi-dimensional space for the data points of the scans) can be increased or decreased a certain percentage based on the scalar. Thus, if a person has a same body type but is smaller or larger, a scalar can be used. Different dimensions can have different scalars, e.g., a different scalar for X, Y, and Z, or a different one for R, theta, and phi for spherical coordinates. Thus, a shape of the surface can also be modified. Other transformations besides a simple scalar can also be used.

In one embodiment, a reference object (e.g., reference object 370) can be used in determining how the mapping model from the control patient group is to be scaled. For example, the reference object can be used to scale the relative coordinates from the one scan, thereby altering the scalar for the control patient group mapping determined from the scan. As another example, the reference object's position relative to features of the patient's body (e.g., eyes, shoulder, etc.) can be used, at least partly, to determine the scaling function to be applies to the control patient group mapping.

In another embodiment, multiple scans can be used to determine how a general mapping model (e.g. as determined from one or more control patients) should be modified for the particular patient. In another embodiment, the few scans can be used to determine a first model, which then is modified based on the more general mapping model, e.g., higher frequency changes of the multi-dimensional surface can be obtained from the general mapping model as more scans may have been used to determine it.

V. Positioning of Beam Assembly

Embodiments can also be used to position the radiation beam. In various aspects, the positioning can be accurate and the beam assembly can be relatively inexpensive compared to current beam assemblies. In one embodiment, such positioning can be achieved using markers on the beam assembly.

Figure 7:
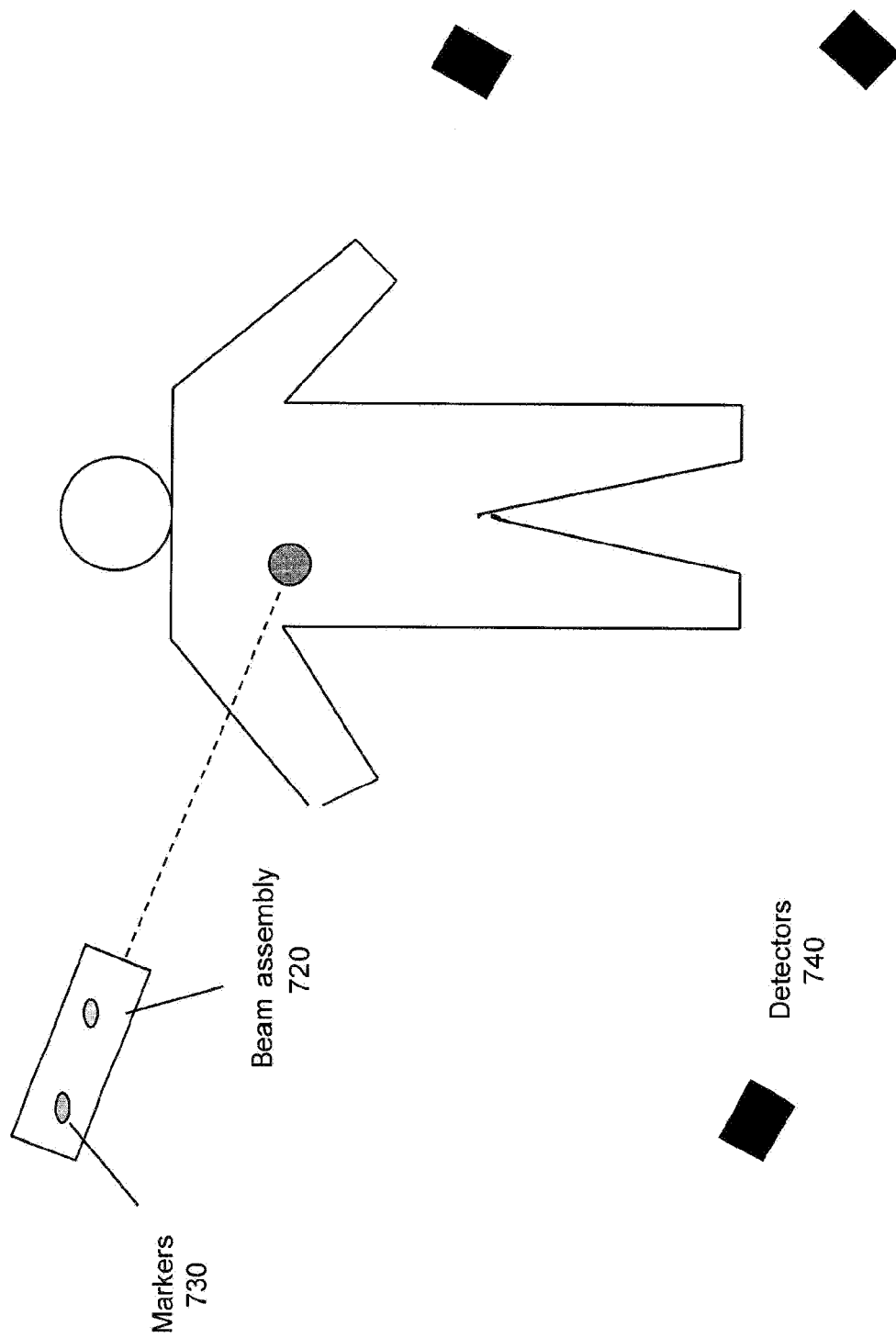
FIG. 7 shows a system for positioning a trajectory of a radiation beam from a beam assembly 720 according to at least one embodiment.

FIG. 7 shows a system for positioning a trajectory of a radiation beam from a beam assembly 720 according to at least one embodiment. Markers 730 are placed on the beam assembly 720. The positions of the markers can provide a location and/or orientation (for example angular orientation) of the beam assembly, thereby providing a trajectory of the radiation beam. The detectors 440 can be connected with a computer system that determines the trajectory.

In one embodiment, the markers are wireless (e.g. optical) and detectors 740 can be used to determine the positions, e.g., by receiving radiation transmitted from or reflected off of the markers. The markers can function in a similar manner to any of the embodiments described for the markers on the patient.

In one embodiment, the system can be calibrated by knowing the placement of the markers on the beam assembly. With such knowledge, the position of the markers can have a static relationship to the trajectory of the beam. For example, the beam assembly can be built with a certain tolerance that the trajectory of the beam will essentially be the same relative to the location and/or orientation of the beam assembly (which is known from the markers). The location of the markers in the room can be calibrated in a separate step, which may be the same step as the calibration for the markers on the patient.

In another embodiment, the system can be calibrated by detecting the positions of the markers and then determining a trajectory of the radiation beam. In one aspect, the beam can be detected at two points to determine the trajectory. The beam can be measured at a particular point in a variety of ways, such as with detectors that are situated on the other side of the patient from the beam assembly. The detectors can have an array of elements having a known position, where the radiation beam activates an element. Some radiation may be absorbed by an element, but some radiation will pass through to activate an element of another detector.

The beam assembly can then be moved to a variety of positions, and the measurement performed again. Each set of marker positions can define a trajectory, with these values defining a data point for the position of the beam assembly. Therefore, a functional relationship between marker position and trajectory can be obtained. Not every possible marker position need to be explored as a functional fit (for example one or more of interpolation, extrapolation, approximation) can provide intermediate values. Also, changes in the trajectory for rotations (e.g. around a single axis) for a particular location can be assumed to provide similar changes in trajectory for the same rotations at a different location of the markers.

In yet another embodiment, detectors could be used to track the radiation beam during treatment to provide another layer of feedback information. In one aspect, such tracking can happen at a coarser level of refinement, such that the trajectory of the beam is determined by the markers on the beam assembly more often, but the function of the marker position to trajectory is updated based on the detection of the beam at larger intervals.

A beam assembly 720 that uses any one or more of the feedback mechanisms can be made cheaper (e.g. expensive stepper motor may not be required) and/or lighter. With these advancements, or even otherwise, two beam assemblies can be used to provide treatment within a shorter period of time. In one aspect, using two or more beams can help to provide a quicker reduction of the diseased tissue than even half the time required for one beam. For example, the amount of heating of the VOI can be greater than double with two beams than just one beam. In another embodiment, each beam can be lower power when used in combination.

In one embodiment, when a location of the VOI is known, a computer can determine a particular trajectory of the radiation beam (e.g., as part of a particular path over time). The beam assembly can be moved and when the desired trajectory is achieved, the radiation beam can be turned on.

VI. Movement of Patient

As mentioned above, embodiments can sample the locations of the markers on the patient at various intervals during treatment. If the patient moves between samples, then the radiation beam may become unfocused from the VOI (for example VOI or other diseased tissue), or irradiate healthy tissue. The system can sample the marker locations quite often in order to minimize such an error. However, if the motion is fast (e.g. relative to the sampling frequency of marker location) and over a relatively large distance (e.g. as compared to the size of the VOI) so that the motion is not a simple vibration, then errors can persist.

Some embodiments can account for patient movement during treatment, including movement that is relatively fast. Various responses to the movement can depend on the type of movement and can depend on the equipment and functional response of the beam assembly (e.g., the speed at which a beam assembly is positioned). The embodiments described below can be used with embodiments described above (e.g. using relative coordinates) as well as other techniques, e.g., where markers are attached to the VOI itself.

A. Predicting Location Between Samples of Position

FIG. 5A shows an intermittent error in beam positioning due to movement of a VOI 810 according to at least one embodiment. At time 0 seconds, the beam 820 is focused on the VOI 810. The sampling period of the markers is 0.2 seconds. At time 0.1 s, the VOI 810 has moved (e.g., due to the patient moving), and the beam 820 is no longer focused on the VOI. If the movement was small, then the beam might simply be focused on an edge of the VOI. But, as shown, the movement was relatively large or fast, and thus the beam is no longer focused on the VOI. Such an example may be an extreme example, but is used to better illustrate embodiments.

At time 0.2 s, the beam 820 is again focused on the VOI 810. Given that the markers were sampled at 0.2 s, the location of the VOI was deduced, for example, from the relative coordinates of the markers using a model as described in any of the embodiments described herein. This example assumes that the beam was focused instantly when the marker locations were read; however, a delay can occur, which embodiments can also account for, as is described below. At time 0.3 s, the VOI 810 again has moved (e.g., with approximately a constant velocity or acceleration), and thus the beam 820 is again not focused on the VOI 810.

Some embodiments can identify that motion is occurring, and use information about the motion to focus the beam in between sampling of marker locations (and thus between times when the VOI location is known). Such embodiments can predict where the VOI will be, and thus predict a particular trajectory of the VOI between samples. For example, the position of the VOI at several times can be used to calculate an acceleration and/or velocity (for example vs. time). Thus, for linear motion, the equation: position(time) 0.5*acceteration*time$^2$+velocity*time+initial position, can be used to predict where the VOI location will be at any time between the sampling times, in one embodiment, the values of acceleration, velocity and initial position can be considered three dimensional vector parameters for the equation of motion. The variables of acceleration and velocity can be computed using simple algorithms e.g. using two data points for velocity or three for acceleration), or many data points, which can involve optimization of a cost function. Other functional forms for law of motion can include simple harmonic motion, which may be linear or circular.

Besides models that are based on laws of motion, time-dependent functions for predicting a next location of the VOI at a future time period can have other functional forms. For example, Fourier functions (such as sine and cosine), polynomials, Legendre polynomials, spherical harmonics, or any other basis functions can be used to approximate the data points obtained from measuring the location of the VOI over time. The variables (e.g. linear coefficients) can be determined via an optimization algorithm that minimizes a cost function, e.g., a difference in the time-dependent function and the measured locations of the VOI, a difference in the variables from one optimization (e.g. at a first time) to another optimization (e.g., at a later time). The other time-dependent functions can be implemented in a same way as the laws of motion to determine where the beam should be pointing between samples or at a point in time that is later than the time of a position measurement. As each new data point of the measured location of the VOI is obtained, the time-dependent functions can be updated through a new optimization of the cost function, which has changed due to the new data point.

FIG. 8B shows an example of a prediction of a location of a VOI between sampling times, according to at least one embodiment. In FIG. 8B, the location of the beam 830 is the same as beam 820 at times 0 seconds, 0.1 seconds and 0.2 seconds. Given that there is data for three sampling times, a velocity and acceleration of the VOI can be determined. This acceleration and velocity can be used to move the beam 830 to be focused on the VOI 810 at time 0.3 seconds, and potentially any time between 0.2 seconds and 0.3 seconds. Thus, the update of the beam position can be more often than the sampling frequency of the markers.

In one embodiment, a minimum number of sampling locations can be required before the movement of the VOI is predicted, and the predicted location used to position the beam between sampling times. Such a requirement can ensure that the equations of motion are accurate and that the motion of the patient is consistent enough to determine a predictive equation.

In other embodiments, other equations of motion can be used. For example, circular motion could be detected, or other curvilinear motion. In one embodiment, a computer system can have a predetermined number of equations for various types of motion. Each type of motion can be associated with a particular equation. Once the location information is matched to a type of motion (e.g. linear, curvilinear, rotational) then the corresponding equation can be chosen and parameters of the corresponding equation chosen. Other types of motion, such as periodic, can provide combinations to determine the equation. For example, a particular equations can exist for periodic linear motion and a different equation for regular linear motion. In some implementations, one type of motion can be initially identified, and subsequently, a new type of motion can be identified (e.g., linear first and then periodic linear subsequently). In one implementation, the parameters for each possible equation can be calculated at each sampling time, and a type of motion can be determined for that sampling time, with the corresponding equation being used to predict the VOI location until the next sampling time. In another implementation, the decision of which type of motion and which equations of motion to use can be performed at every Nth sampling time, where N is greater than one. The determination for which equation (model) is to be used can be determined by comparing a best-fit of the parameters of each model to the location information and selecting the model that provides the best-fit. The best-fit can be determined by calculating an error for each model, e.g., an error between the model and the determined locations of the VOI.

B. Predicting Location with Delay in Beam Positioning

A delay can exist between the time that the locations of the markers are determined and the time that a new VOI location is determined from coordinates of the markers (e.g. relative coordinates of the markers). There can also be a delay between the time that the new VOI location is provided to a beam positioning mechanism and the time that the beam is positioned at the input VOI location. After these delays, the VOI may have already moved to a new location.

For example, in FIG. 8A or 8B after a sampling at 0.2 s, the beam may not be re-positioned until 0.21 seconds, and thus the VOI would have moved to a new location based on a particular acceleration and velocity during the intervening 0.01 seconds. In addition, any healthy tissue, which is sought to be avoided, can also have moved thereby causing the beam to irradiate (for example vital) healthy tissue (e.g. the heart). Such a problem could be even worse if these delays are greater than the sampling period.

Some embodiments can reduce a beam positioning error due to a time lag between the time a set of position samples are electronically measured and the time required to (i) record the measurements, (ii) process the measurements, (iii) use the measurements to calculate where the beam should ideally point, and then (iv) cause the beam assembly to move to the new pointing position. By knowing how long the lag is for this sequence of measurement, processing and positioning steps, the beam can be positioned according to an estimate of where the beam should ideally be positioned at the end of the time tag, rather than using an estimate of where the beam would have been ideally positioned at the time the measurements were sampled (at the beginning of the time tag) under the assumption the VOI are stationary.

Figure 9A:
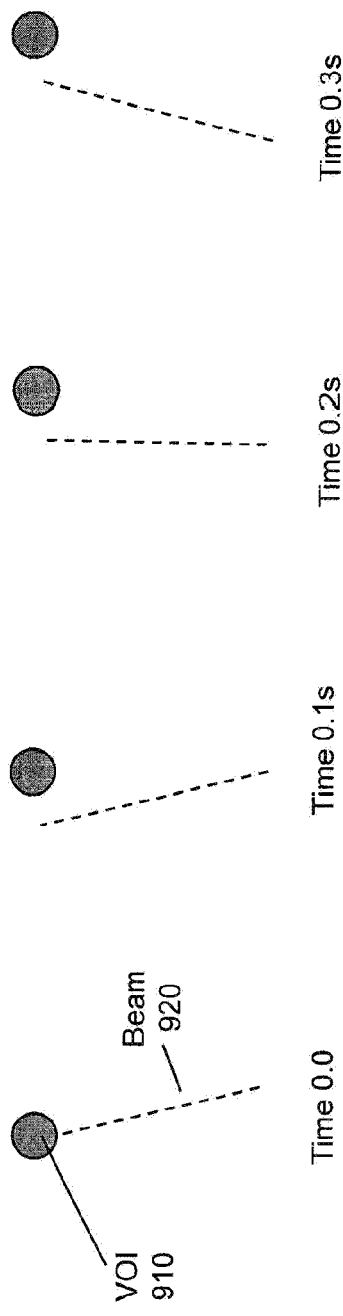
FIG. 9A shows a constant error in beam positioning due to movement of a VOI 910 according to at least one embodiment.

FIG. 9A shows a constant error in beam positioning due to movement of a VOI 910 according to at least one embodiment. In this example, the sampling period is 0.1 seconds, but there is a delay of 0.1 seconds from the time the marker location are detected and the re-positioning of the beam. At time 0.0, the beam 920 is focused on the VOI 910 (e.g. because the VOI 910 has been stationary). From time 0.0 to 0.1 seconds, the VOI 910 moves and the new marker locations are detected. However, the beam 920 has not been re-positioned yet, so there is an error.

At time 0.2 seconds, the beam is updated to have the position of where the VOI 910 was at time 0.1 s, but now the VOI 910 has moved to a new position. Thus, there is still an error. Accordingly, the positioning may always lag behind the actual VOI location if the VOI continues to move faster than the system can re-position.

Figure 9B:
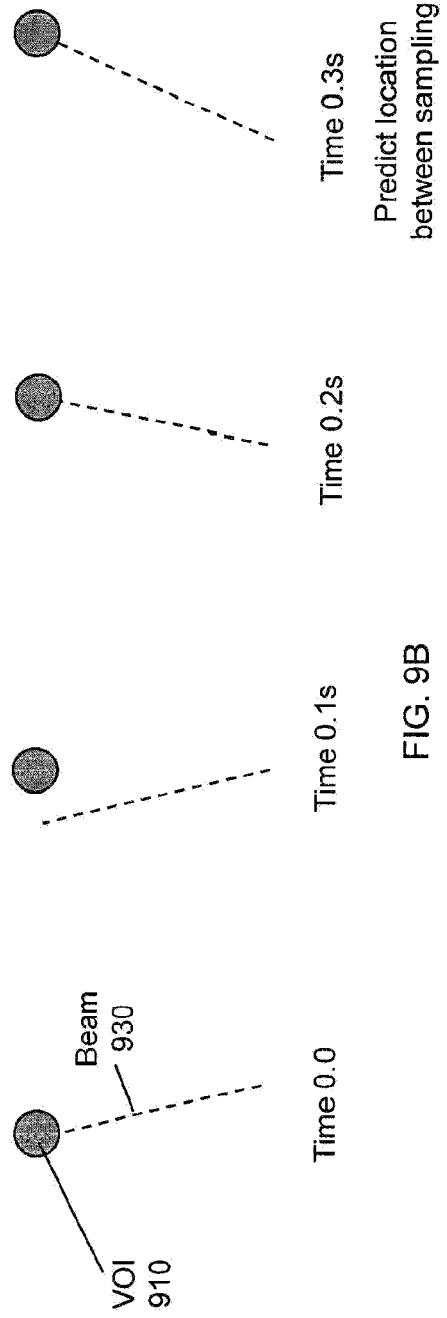
FIG. 9B shows an example of a prediction of a location of a VOI between sampling times where the prediction accounts for a delay between sampling and positioning of a beam according to at least one embodiment.

FIG. 9B shows an example of a prediction of a location of a VOI between sampling times wherein the prediction accounts for a delay between sampling and positioning of a beam, according to at least one embodiment. At time 0.1, the beam 920 is still not focused on the VOI 910 since the system is still processing the new position information. However, for time 0.2 seconds, the system can use the position information at time 0.1 seconds to predict where the VOI will be at 0.2 seconds since that is the time the system knows corresponds to the delay. For example, once the system receives the sampled location information about the markers at time 0.1 s, the system can calculate the predicted VOI location at 0.2 s (and just skip over any calculation of the VOI location at time 0.1 s since the beam cannot be positioned quick enough anyway). The delay for a particular system can be determined during a calibration process.

For time 0.3 s, the system can use the position information from times 0.1 s and 0.2 s, to calculate the VOI location at time 0.3 s. In one aspect, the VOI location of at time 0.3 s is fed into the beam positioning system prior to the time of 0.3 s. For example, assume that the delay to calculate the VOI location is 0.02 seconds and the delay to re-position the beam is 0.08 seconds, then the new VOI location is computed for 0.3 seconds (using the position information at times 0.1 s and 0.2 s) and is provided to the beam positioning system at 0.22 seconds, so that when the beam is re-positioned at time 0.3 seconds, the beam will approximately be at where the VOI is actually located at 0.3 seconds.

In some embodiments, a delta $\Delta$ (e.g. 0.1 s) can be added to the time of the prediction equation so that the position that is fed into the positioning system to position the beam is always 0.1 seconds greater than when the marker locations were last sampled. For example, a velocity can be determined from the position of the VOI 910 at time 0.1 s and the location at time 0.0. Then assuming linear motion, this velocity can then be used in equation: (position(time)=velocity*(time+$\Delta$)+initial position. Once further data points are Obtained, more complex equations can be used with the time offset. Thus, in one embodiment, the computing system does not use the current time in the equations of motion, but uses the current time plus a time offset by $\Delta$.

Embodiments for handling the various delays can be combined. Thus, the beam's position can be updated more often than the sampling points, based on equations of motion derived from recent location measurements (i.e. marker locations and subsequent calculation of VOI location). And, the equations of motion for the updates can use a time offset so that the position is the expected VOI location at the end of the re-positioning process. For example, if sampling of marker locations is done every 0.2 s, a prediction engine can receive a new VOI location every 0.2 s; but the VOI location can be old by 0.02 seconds under the above example, where the delay of calculating the VOI location from marker locations is 0.02. The prediction engine can predict the VOI location at a time of a current time 0.22 s (i.e. 0.02 seconds after the sampling time, in this example) plus a time offset of 0.08 s (the delay in the positioning mechanism) to obtain a predicted VOI location at 0.3 s. Assuming the prediction engine computes a predicted VOI location every 0.1 s (which can be more often than the sampled marker locations are received), the prediction engine would compute the next VOI location (e.g. using the same equations of motion used for the calculation at time 0.22 s) at time 0.32 s with an offset of 0.08 s to provide a predicted VOI location at 0.4 s.

Besides using a fixed offset Δ for computing the next position, the time-dependent functions to predict VOI position (and possibly undesired tissue position) can be used in combination with the response of the beam assembly positioning as a function of time. The response time to position the beam may change over time, e.g., the response time may be longer when the VOI is moving faster and the beam assembly must move faster to keep up, thereby resulting in more time lag. As another example, different delays can be encountered depending on the last position of the beam and what the new commands are. Such different delays can be due to different total distances that the beam assembly needs to be moved. The beam assembly can be made to move faster when the distance to be moved is more, but in general, the movement speed of the beam assembly should correlate to the time step for the new position (i.e. related to the average velocity of the VOI and/or beam over the time period so that the beam assembly would be focused on the VOI during the movement of the beam.

The response time can be measured for each new set of input commands for changing the position of the radiation beam, thus a function G of the response time that approximates these data points can be determined (e.g., by computing coefficients of basis functions that minimize a cost function). The cost function can include contributions from a difference in the time-response function G from the measured response time. The function G could also be determined from the values of the time-dependent function for the VOI. For example, the response time could be estimated from the acceleration of the VOI, or from higher order terms (such as the change in the acceleration). The time-response function G can be pre-computed during a calibration process, and may be updated during treatment.

C. Determining Beam Position from Position

Using the embodiments described above, one can calculate the position of VOI (for example comprising diseased and/or healthy tissue) at a given time. A number of positions can be obtained for each time. The plurality of positions can include multiple positions on a surface of a VOI, positions of multiple VOIs. All of these positions can be used to determine an optimal (or desirable) beam position, as well as any other beam properties, such as one or more of beam intensity, beam width, beam shape, beam orientation, beam trajectory, beam multileaf collimator (MLC) settings, beam properties relative to a VOI or a patient, positioning of a patient couch relative to the beam, positioning of the patient or VOI relative to the beam properties, etc.

The optimal beam can be computed by optimizing a cost function. For example, the optimal (or desirable) position (or other beam properties described above) can minimize the cost function, which can have contributions due to diseased and healthy tissue. The cost function can decrease when there is more overlap of the beam with the diseased tissue (e.g. the beam is irradiating a tumor), but increase if there is more overlap with healthy tissue (e.g. a penalty is paid for irradiating healthy tissue). The cost function can be tailored such that the penalty for irradiating healthy tissue is high (and also may vary depending on the healthy tissue that would be irradiated, such as the heart) relative to the benefit (i.e. reduction in the cost function) for more overlap for the diseased tissue.

D. Method Of Predicting Location Of VOI

Figure 10:
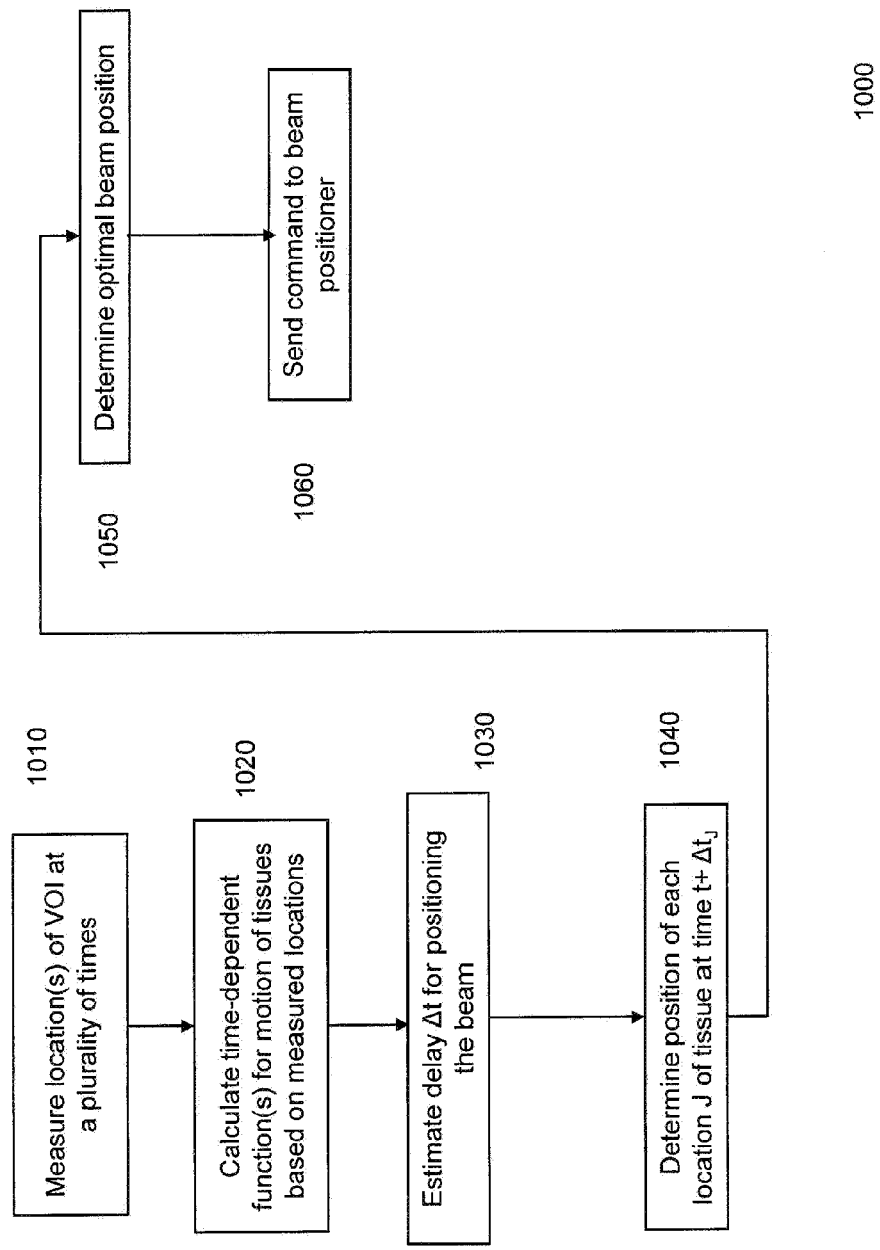
FIG. 10 is a flowchart illustrating a method 1000 for tracking motion of VOI and determining an optimal beam position based on the motion according to at least one embodiment.

FIG. 10 is a flowchart illustrating a method 1000 for tracking motion of VOI and determining an optimal (or desinthle) beam position (or other beam properties described above) based on the motion according to at least one embodiment. Method 1000 uses time-dependent functions (which may be time-varying or adaptive) to predict motion of VOI and an estimate of delay in the system to account for various system errors.

In step 1010, one or more locations of VOI (for example including diseased and/or healthy tissue) are measured at a plurality of times. The measurement may be made as described above, for example, combining a less precise method during treatment (e.g., using locations of fiducials) with a model for mapping the less precise measurements to more precise measurements. The less precise measurement could be internal measurement, e.g., using standard x-ray, or external measurement, e.g., using wireless elements (as described above) or imaging techniques. The times may be the N most recent measurements, or all of the measurements within a prescribed time.

In step 1020, time-dependent function(s) for motion of the tissues are calculated based on the measured locations. Each different tissue can have its own time-dependent function, and even multiple locations on each tissue can have a separate time-dependent function. Each location can be broken up into separate dimensions (e.g. Cartesian coordinates, spherical, cylindrical, and so on), and thus each location have three time-dependent functions, one for each dimension.

The time-dependent function can be determined in a variety of ways. For example, one may use a set of basis functions (e.g. polynomials in time t), and determine the coefficients that best approximate the motion defined by the measurements from step 1010. Thus, the time-dependent functions could be of the form $a+bt+ct^2$, with a being the initial offset, b being velocity, and c being an acceleration term (e.g. proportional to acceleration). Higher order polynomials can be used, as well as other basis functions. The coefficients of the basis functions can be determined by optimizing a cost function, e.g., mean square difference or worst square difference between the time-dependent function and the measured data points from step 1010. Non-linear variables can also exist within the basis functions, but such inclusion can make their calculation more difficult.

Accordingly, a time-dependent function can have the generic form of $X_{I,J}(t)=F(C,t)$, where X is a matrix with one dimension (e.g. 1) being three and the other dimension (e.g. J) being the number of locations whose motion is being modeled (for example for prediction), and where $C_{I,J,M}$ is a $3^{rd}$-rank tensor (or simply an array with three dimensions) of the coefficients that are determined via the optimization step. The index M can run over the number of variables defining the time-dependent function for the particular coordinate I of location 0.1 of a tissue. Then, C can be determined by optimizing a cost function $E(C,t,Y)$, where Y is the measured data points from step 1010.

In one embodiment, E can equal $\Sigma(Y-F)^2$, where the sum is over one or more of time points, number of coordinates, and number of locations of tissue being tracked. Note that each (target point or VOI) time-dependent function can be treated as a separate function. Alternatively, the motion for different coordinate locations can be dependent on each other, e.g., the locations on a surface of a VOI would have some correlation with each other. Additionally, the variables for the location(s) of different tissue can be calculated with different accuracy. This may be achieved using different weightings in the cost function E. For example, the sum of the least square errors for a particular location(s) of an object (tissue) can be multiplied by a larger factor in order to give more importance to obtaining accurate values of C for the object.

The function F can be re-calculated for each new data point, or every Nth data point, where N is greater than one. The calculation of F can be independent from how often a new command is given to the apparatus for positioning the beam. For example, F can be re-calculated every 0.5 seconds, but a new command can be sent to the beam positioner (also called a movement mechanism) every 0.1 seconds. Thus, the last F can be re-used to determine new positions for the beam.

In step 1030, the delay $\Delta t$ for positioning the beam is estimated. In one embodiment, $\Delta t$ could be chosen as a fixed value. For example, the system could assume that from the time of computing the locations (which could include or not include determining the time-dependent function F), including the time to compute the optimal beam position, until the beam is positioned at its new designated position (i.e. as designated by the commands given to the positioner) is a constant. In another embodiment, the value of $\Delta t$ can be different (for example the value could change over time, or positioning, or past and/or future positioning of VOI or past and/or current and/or future beam parameters, etc.). For example, if the VOI is moving faster, it will take longer for the beam assembly to move into the correct position. Thus, $\Delta t$ can be larger. Note that if $\Delta t$ was large enough, the beam may not reach its final designated location by the time a new command is given to the positioner.

For a variable delay $\Delta t$, the time may be estimated based on the values of C. For example, the maximum coefficient for the velocity or acceleration can be used to determine $\Delta t$, as that acceleration can dictate how long it will take to position the beam. In yet another embodiment, the value of $\Delta t$ can vary for each location being tracked.

In other embodiments, $\Delta t$ can be determined from any combination of distance traveled for last time step, error of predicted position from actual position of VOI, and a beam error of actual trajectory of the beam from an optimal trajectory of the beam. Using the feedback of the beam error can allow for machine learning, e.g., via optimization algorithms to determine better input commands into a beam assembly for moving the beam. The actual trajectory can be computed, e.g., as described in section V above.

In step 1040, the position of each location J of VOI is determined at time $t+\Delta t_J$, where t is the current time. The result is that the location of the VOI is computed for a future time. Since the beam is expected to take $\Delta t_J$ to move to the position at $t+\Delta t_J$, the beam is expected to move along a similar trajectory that that the VOI is moving. Thus, the error is reduced compared to using the position of the VOI at the current time.

In step 1050, the optimal beam position (or any other parameter or configuration the beam relative to the VOI or the radiation treatment system relative to the VOI) can be determined, e.g., as described above. For instance, a cost function that uses locations of diseased tissue and healthy tissue can be used to find a beam trajectory that reduces risk to vital organs while providing radiation to a tumor. In some cases, the radiation beam could be turned off if the certain criteria cannot be met (e.g., the cost function is above a certain value, which can indicate that healthy organs would be damaged). Once an optimal beam position is determined commands for a beam positioner can be determined. In one aspect, the optimal beam position can be a command.

In step 1060, the command for the new position is sent to the beam positioner. The commands may be analog or digital signals. The beam positioner may be a stepping motor. In one embodiment, the commands may be high level commands that specify a position of the beam assembly or a particular trajectory. The beam positioner can include a processor that receives the high level position commands and determines the specific signals to send to actuators for moving the radiation beam.

Regarding the calculation of the time-dependent functions, some embodiments can use certain information to determine what kind of motion is occurring. For example, which markers are moving can be used to predict how the patient's body is moving. If the markers on the patient's torso are moving rotationally, then the person's whole body is likely turning. If the VOI is located within the torso, the motion of the VOI is likely around an axis within the patient's body. Thus, rotating motion can be assumed, and the corresponding equations can be used. Certain criteria can be used to classify the type of motion, and then use equations corresponding to that type of motion. Other implementations can use a single more general equation for multiple types of motion.

As another example, the markers could identify that the patient is moving his/her arm or leg. If the VOI is within the arm or kg, then the motion can be constrained by knowledge of the patient's body, such as length of the arm or leg and knowledge that only certain types of motions are possible (e.g. hinge-like motion for the elbow or knee). Thus, the knowledge of the type of motion and the physical constraints of what motions are possible can be used to accurately where a VOI may be.

In one embodiment, the beam can be turned off if the movement of the patient is measured (via the markers on the patient) to be faster than a threshold value, and/or erratic enough that a prediction is deemed not to be accurate within a threshold. The threshold may be determined based on how fast the system can determine the VOI location and change the beam trajectory, e.g., a latency of the system. This threshold for the rate of acceptable movement can be determined during a calibration (or equivalently a quality assurance or verification) procedure, e.g., using a dummy or phantom instead of a real patient.

VII. Determining Trajectory of Optimal Beam Position

In the last section, the position of the VOI as a function of time was determined. Based on this predicted motion, an optimal beam position was determined for a particular time. In the embodiments of this section, the position of the Val as a function of time need not be determined. Instead, a beam trajectory can be determined as a time-dependent function of beam position (e.g., 3-dimensional location and 2-dimensional angle). The beam trajectory can be determined to minimize an error between an actual beam position (e.g., as measured) and an optimal beam position at a set of times. The optimal beam position at a particular instant in time can be determined based on a determination of a position of a VOI at the particular instant in time (e.g. via a measurement made at that instant in time).

A. Method Using Feedback Error

Figure 11:
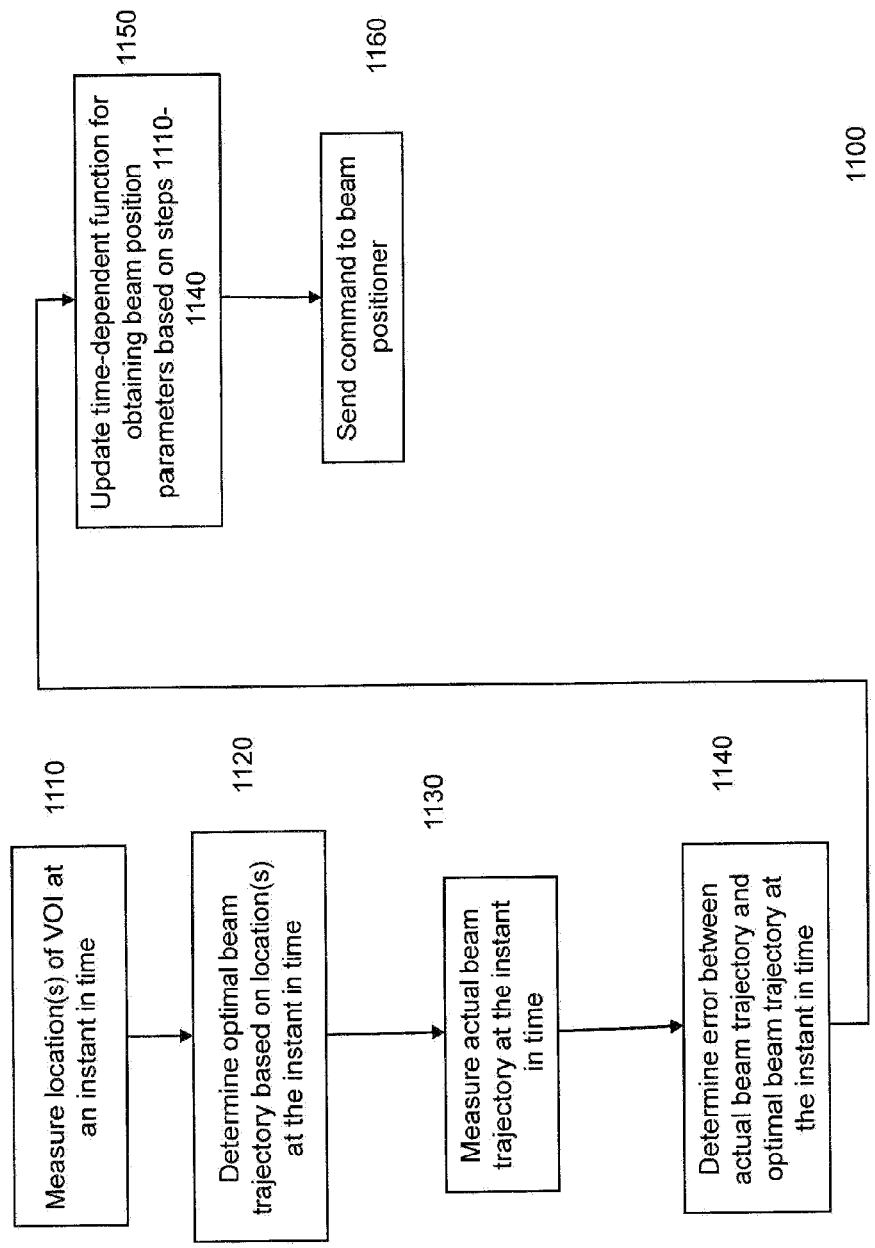
FIG. 11 is a flowchart illustrating a method 1100 for determining an optimal beam position based on feedback error according to at least one embodiment.

FIG. 11 is a flowchart illustrating a method 1100 for determining an optimal beam trajectory based on feedback error according to at least one embodiment. Method 1100 uses time-dependent functions that account for the motion of the VOI. The time-dependent functions could be used to predict the motion of the VOI, or used to predict the change over time of an optimal beam trajectory or inputs to a beam positioner.

In step 1110, location(s) of VOI is measured (or estimated or predicted) at an instant in time (for example current, past or future). The location can be performed using methods described herein, e.g., using a mapping model obtained from a pre-treatment scan. The locations of the VOI could also be obtained directly with markers (for example fiducials) attached to the VOI. Any suitable method for measuring the location may be used.

In step 1120, an optimal beam trajectory can be determined based on the location(s) of the tissue(s) at the instant in time. For a given location of VOI (for example comprising diseased and/or healthy tissue), an optimal trajectory can be chosen. The term optimal as used herein does not require the best trajectory possible, but a value that is determined optimal within a specific criteria (e.g., a cost function is below a certain value). Accordingly, the optimal beam trajectory could irradiate some healthy tissue, but the amount would be within specific parameters.

In step 1130, the actual beam trajectory is measured at the instant in time. The actual beam trajectory can be measured as described herein. For example, the radiation beam may irradiate detectors, which can identify a particular location of the disturbance of the detectors. As another example, beam assembly markers (e.g. as described in FIG. 7) can be used to determine the beam trajectory at the particular instant in time.

In step 1140, an error between the actual beam trajectory and the optimal beam trajectory at the instant in time can then be determined. The error can result from various factors as described herein. An error can be computed for each degree of freedom of the beam trajectory, e.g., three spatial coordinates and two angular coordinates. The measurements of the actual beam trajectory can be determined on a continuous basis, and stored with a time stamp. Once the VOI location is determined, the time $t_0$ can also be stored, so that the corresponding optimal beam trajectory at time $t_0$ can be compared to the actual beam trajectory at time $t_0$. In one embodiment, the error for different degrees of freedom can be weighted differently, e.g., the angular degrees of freedom can be weighted higher as they may have more of an impact on the change of the cost function for a beam trajectory.

In step 1150, a time-dependent function for obtaining beam trajectory parameters is updated based on any one or more of the values obtained in steps 1110-1140. In various embodiments, the time-dependent functions can specify the motion of the VOI, the change in the optimal beam trajectory over time, and the change in input commands to a beam positioner. The update can include changing a time offset for determining the next input command (e.g. providing a command for a future point in time to account for delays in the system) or parameters that affect the actual next input command (which could be any parameter for any of the time-dependent functions).

In step 1160, one or more commands are sent to a beam positioner. The input commands provided at a time $t_0$ could be for a different beam trajectory than the optimal beam trajectory at time $t_0$. For example, the input could be for a greater position than the optimal beam position at time $t_0$, but due to time lag $\Delta$, the actual beam position at time $t_0+\Delta$ will be or approximately be the optimal beam position for time $t_0+\Delta$. Thus, the input commands can be determined to reduce the error between the actual and optimal beam trajectory for a set of measurements at different times.

In some embodiments, the beam assembly can have a continuous motion as opposed to discrete movements to new positions. For example, commands can provide parameters for equations of motion of the beam assembly, as described herein. Such parameters can include velocity and acceleration, or other variables for any suitable time-dependent function. The positioning system can then move the beam assembly according to those equations, whose parameters are based on the positions of the markers. Such embodiments can take in account present or past beam assembly velocity and/or present or past beam assembly acceleration. For example, changes in velocity or acceleration to new values can have different delay based on what the current or previous values were. A time-response function G to predict delays in positioning the radiation beam can be computed as described above. This time-response function can be calibrated and recorded. The time-response function G can then be used to estimate the ideal beam position commands (e.g. by determining the proper time offset at a given instant in time or simply changing the variables to account for any delays.

B. Updating Time-Dependent Function Beam Position Parameters

The feedback of the errors in the actual beam position and the optimal beam position can be used to various ways to update the time-dependent functions of the beam position parameters. For example, a time-dependent function can be determined for the optimal beam trajectory, and the beam error from step 1140 can be used to determine a time offset (e.g. due to lag), in a similar manner as explained for method 1000. As another example, a time-dependent function can be determined for the beam position parameters. This time-dependent function would typically not be the same as for the optimal beam trajectory, and thus can incorporate any lag in the system into the function itself without using a time offset.

Update $\Delta t$

The time-dependent function for the optimal beam trajectory can be calculated from the optimal beam position determined at a plurality of times. Each position of the beam can have a separate time-dependent function. As the beam can have two angular degrees of freedom, along with the three-dimensional spatial coordinates, five time-dependent functions could be used. The functions can have an assumed functional form (basis functions), such as polynomial, which could be of the form $a+bt+ct^2$ or of higher order, as mentioned above. But, other basis functions suitable for periodic motion can be used. A cost function, such as least square error, can be used to determine the variables or alternatively parameters or coefficients) defining the functions.

Even if the time-dependent function was able to accurately predict the next optimal beam position, there can still be an error due to the imprecision of the positioning mechanism for the beam, or any time lags in the calculations and the positioning. Thus, a beam error determined in step 1140 can be non-zero. To account for such errors, a time-offset $\Delta t$ can be used in a similar manner as described above, A single time-offset $\Delta t$ can be used for all of the time-dependent functions, or the time-offset $\Delta t$ can vary between the different time-dependent functions. Thus, each degree of freedom can have its own value for $\Delta t$. The value of $\Delta t$ can be determined in a similar manner as mentioned above. For example, $\Delta t$ can be determined from the beam error, the variables of the time-dependent functions (e.g. a coefficient corresponding to velocity and/or acceleration), and the change in position of the VOI being tracked between sampling times.

In one embodiment, the beam error can be used as feedback to increase or decrease the value of $\Delta t$. For example, if the error is a result of an overshoot (i.e. the beam was moved past the optimal beam location), the value of $\Delta t$ can be reduced for the next determination of the beam position. The amount of reduction can be determined via an optimization algorithm that uses previous errors and the corresponding $\Delta t$ values. For an undershoot, the value of $\Delta t$ can be increased. If the error is zero or almost zero (e.g. within a threshold of zero), then the value of $\Delta t$ can remain unchanged. As a beam error can be computed for each degree of freedom of the beam position, a different value of $\Delta t$ and change to $\Delta t$ can be used for respective time-dependent functions corresponding to the different degrees of freedom. As the value of Δt is being updated, the time-dependent function of the optimal beam trajectory can be re-calculated for each new data point of the optimal beam position.

Update Coefficients for Time-Dependent Function of Beam Parameters

In another embodiment, a time-dependent function(s) of the optimal beam trajectory is not calculated, but instead a time-dependent function(s) of the input positions (commands) into the beam assembly for positioning the beam. In this manner, the time-dependent function is not necessarily related to any particular movement, but can be computed as the function that minimizes the beam error. However, input values for one or more previous positions of the VOI may be used.

The initial values for the variables of the time-dependent functions can be computed in a similar manner as for the optimal beam trajectory. For example, a function approximating the data points of the optimal beam trajectory can be computed. In another embodiment, the error at a particular instant in time can be paired with a particular input to the beam assembly, thereby providing an error in the initial values for the variables. Combining the error with the actual input values (e.g., input position), one can determine an estimated value for the optimal input values. The time-dependent functions for the input positions can then be computed in a similar manner as any of the functions mentioned above. One can also compute the time-dependent function as delta value for how the beam assembly should move based on a most recent value for the beam position. This delta value in the change of the function value can itself vary over time, e.g., as computed based on an optimization of a cost function using previous errors.

Once the variables of the time-dependent function(s) for the input positions are determined, the variables themselves can be updated based on the measured beam error. The variables can be updated in various ways. For example, the variables can be updated as each new error point is received. The direction of change can be computed in a similar manner as for Δt. As another example, the variables can be updated by combining the error with the actual input values, as is described above.

In practice, the combining the error with the actual input values can involve optimization algorithms, such as conjugate gradient (with the error being the gradient) or quasi-Newton methods, non-linear methods (such as Neural Networks) or other types of machine learning. The basis functions for the time-dependent functions can include neural networks and delta functions (e.g., simply vector values at different instances in time), as well as others mentioned above. The new values for the variables defining the time-dependent function(s) would then be chosen so as to minimize (or at least reduce) the measured beam error. The cost function for the optimization would involve the beam error(s) (e.g., one for each degree of freedom), and could simply be a sum of the beam errors at the times being used, or some other function. The various beam errors could be given different weightings, e.g., if reducing the error for angle is more important than a spatial placement of the beam assembly itself, or vice versa. The use of a value of Δt can also be combined with this method.

VIII. Transforming Pre-Treatment Image

As mentioned above, a digital pre-treatment body image of a patient (or pre-treatment imaging of a patient) can be created using various techniques (such as CT, MRI, and ultrasound). In some embodiments the digital pre-treatment body image comprises at least a portion of the body of the patient. In some embodiments the digital pre-treatment body image comprises at least a portion of the VOI or a marker associated with the VOI. The pre-treatment body image can include a characterization of the spatial characteristics of one or more first components (e.g. diseased and/or healthy tissue) of the body anatomy relative to one or more markers. As detailed above, the markers may be natural features of the patient's body (e.g., particular locations on bones, a nose, belly button) or artificial markers that are added to the patient's body (e.g. on the surface or internally). The digital pre-treatment body image can be created using one imaging technique (e.g. the markers also are imaged with the same technique as the VOI) or two techniques can be used (e.g. the marker locations are determined with optical or radio frequency signals).

The pre-treatment body image may not be consistent with a treatment coordinate system. An embodiment can determine whether the pre-treatment body image is consistent with the treatment coordinate system. If the pre-treatment body image is not consistent with a treatment coordinate system, the pre-treatment body image can be mapped into a corrected pre-treatment body image that has a coordinate system that is consistent with the treatment coordinate system. The treatment coordinate system can enable the positioning (for example location and/or orientation and/or posture and/or deformation) of the one or more first components of the body anatomy with respect to a positioning (for example location, orientation pointing angle, shape, MLC settings, size, etc.) of a radiation treatment system (e.g. a beam trajectory or beam assembly or patient furniture). For example, the pre-treatment body image can be scaled to the resolution (e.g. by altering the number of pixels in the image) of the detectors used during treatment to detect the markers and position the beam, thereby allowing a unified coordinate system. This mapping can be performed before treatment begins. If the pre-treatment body image is consistent with a treatment coordinate system, then no correction may be necessary, and the corrected pre-treatment body image would be the pre-treatment body image.

During treatment, a digital treatment body image can be created. In some embodiments the digital treatment body image comprises at least a portion of the body of the patient. In some embodiments the digital pre-treatment body image comprises at least a portion of the VOI or a marker associated with the VOI. The digital treatment body image is consistent with the treatment coordinate system. The markers can be located as key features on the treatment body image in the treatment coordinate system. The positions of the markers can be obtained in various ways (such as x-rays, MRI, optical imaging, or ultrasound). For example, an x-ray scan can provide an image with identifiable locations of markers (for example bones, fiducials, or sensors) that provide a signal to detectors. As another example, optical imaging using video or still pictures (or other wireless communication) can be used to detect natural body features or artificially added markers. Any of these and other suitable techniques can provide a digital treatment body image. In one embodiment, the pre-treatment body image is created in a different apparatus than where the treatment body image is created.

A best-fit process (e.g. using optimization techniques described herein) can be used to map information (e.g. positions of tissue and markers) from the corrected (for example transformed with a rigid body or deformation model or projected from a higher dimensionality imaging mode to a lower dimensionality imaging mode) pre-treatment body image to the treatment body image to create an enhanced (for example by image fusion methods) treatment body image, which is consistent with the treatment coordinate system. The best-fit mapping can determine a position offset and/or a rotation offset to apply to the entire corrected pre-treatment body image, or to respective sections of the corrected pre-treatment body image (e.g., if the body has a twist or is bent), or different position/rotation offsets for different components (e.g. markers and VOI) to re-position the corrected pre-treatment body image, or determine a deformation model (for example using splines) or body-model transformation. For example, the offsets can minimize a position difference as measured in the treatment coordinate system between a set of one or more common features (e.g. markers or VOI) in the re-positioned corrected pre-treatment body image and the same set of common features in the treatment body image. The optimization can be constrained so that the offsets reflect possible distances between the two different features (e.g., a hip joint may only have a certain range of possible distances from a nearby VOI).

The enhanced treatment body image can be used to identify a feature (e.g. a marker-natural or artificial) in the image or to determine a desired radiation target (e.g. the VOI) within the treatment coordinate system. Identified features can also be used to determine undesirable radiation targets (e.g. healthy tissue) that are not to be radiated. A control processor can determine a location and/or orientation of the radiation treatment system that will cause a radiation beam to irradiate the desired radiation target (e.g. beam has an optimal beam trajectory). Commands can be provided to the radiation treatment system to cause the radiation treatment system to move to the location and/or orientation and deliver a radiation dose.

The treatment body image may be (or include) body points identified by markers placed on the body. In one embodiment, the markers can be located with wireless position finding techniques, and the radiation treatment system can include detectors to locate the markers in the treatment coordinate system. In another embodiment, the markers can be located with video or still camera imaging techniques, and the radiation treatment system can includes video or still cameras to locate the markers in the treatment coordinate system. The placement of the markers on the body during treatment imaging can be the same, or within a tolerance, as the placement of pre-treatment markers placed on the body during pre-treatment imaging. The treatment markers and the pre-treatment markers can have the same image properties for pre-treatment imaging and treatment imaging. The markers can have an image property that provides enhanced marker location during treatment imaging (e.g. relative to other features in the image) and the pre-treatment markers have an image property that provides enhanced marker location during pre-treatment imaging. In yet another embodiment, the markers (e.g. internal markers) can be located with x-ray techniques, and the radiation treatment system can include x-ray apparatus to locate the markers in the treatment coordinate system.

The radiation treatment system used to locate the markers in the treatment coordinate system can be calibrated prior to treatment by capturing an estimated position in the treatment coordinate system of a test marker of known location in the treatment coordinate system and applying a correction factor to the estimated position so that it correctly maps to the known position in the treatment coordinate system.

In one embodiment, the enhanced treatment body image is used to: (i) enhance one or more image properties and/or one or more location estimates of a first set of image features (e.g. healthy tissue) in the treatment image, or (ii) add one or more image features (e.g. the diseased tissue) in a second set of image features to the treatment body image, where the second set of image features are identifiable in the re-positioned corrected pre-treatment image and are not identifiable in the treatment image. In one embodiment, the one or more first set of features can include image features resulting from markers placed on or near the body. In another embodiment, the one or more first set of features can include body features or anatomy elements identified by a body anatomy identification algorithm applied to the image. The one or more second set of features can include body features or anatomy elements.

Mapping the pre-treatment body image to the treatment coordinate system can be accomplished by calibrating the apparatus used to create the pre-treatment body image so that an absolute measure of dimensions is obtainable from the pre-treatment body image information. The mapping to a corrected pre-treatment body image can then be based on the known absolute dimension information available in the pre-treatment body image, Mapping the pre-treatment body image into the treatment coordinate system can be accomplished by inserting calibration markers of known absolute geometry placed on or near the body during the pre-treatment imaging process. The known absolute geometry of the calibration markers can be used to adjust the pre-treatment body image so that the corrected geometry of the calibration markers in the corrected pre-treatment body image is consistent with their known absolute geometries.

In one implementation, the location and/or orientation of a radiation treatment system can be determined by a pre-treatment calibration procedure wherein a location and/or orientation command is provided to the radiation treatment system. The resulting location and/or orientation of a radiation beam can be measured with respect to the treatment coordinate system. The process may be repeated until a characterization of multiple location and/or orientation commands and the resulting location and/or orientation measured in the treatment coordinate system is sufficient to achieve the required accuracy during treatment. In another implementation, the location and/or orientation of a radiation treatment system can also be determined by placing markers on one or more of the radiation treatment system elements (for example radiation treatment system element that direct a radiation beam or the patient couch), locating the position of the markers in the treatment coordinate system, and applying a mapping of the location of the markers in the coordinate system to the location and/or orientation of a radiation treatment system in the treatment coordinate system.

Determining a location and/or orientation of the radiation treatment system that will cause a radiation beam to irradiate the desired radiation target can include using one or more past positions of the desired radiation target and an estimate of motion dynamics of the desired radiation target to improve the accuracy of the location and/or orientation with respect to the actual real time location of the desired radiation target, e.g., as described above. In some embodiments determining a parameter adjustment (for example one or more of a positioning, position, location, orientation, angle, patient or VOI positioning, patient couch or table positioning, beam parameters—shape, intensity, size, dose, MLC, etc.) of the radiation treatment system that will cause a radiation beam to irradiate the desired radiation target can include using one or more past parameters of the radiation treatment system and an estimate of motion dynamics of the radiation treatment system to improve the accuracy of the location and/or orientation with respect to the actual real time location of the desired radiation target, e.g., as described above.

The enhanced treatment body image may further utilized to identify one or more undesired radiation features in the image and use the one or more undesired image features to determine one or more undesired radiation targets within the treatment coordinate system. Determining a location and/or orientation of the radiation treatment system may not only be based on the location of the desired present state radiation target, but also based on the one or more undesired present state radiation targets that are desired to be avoided when determining the present location and/or orientation of the radiation treatment system in the treatment coordinate system. The desired treatment path (or treatment plan can include a series of future pointing locations and/or pointing angles that will result in more exposure to the desired radiation target than is delivered to other body features including the one or more undesired radiation targets. As time progresses, each of the future pointing locations and/or pointing angles may be used to assist in deriving a present state location and/or orientation.

In one embodiment, the best-fit process to create an enhanced treatment body image can include identifying a first set of body-model reference features in the treatment image, determining a body-model orientation based on the relative position of the body-model reference features in the treatment body image, utilizing the body-model orientation to obtain a body-model enhanced version of the corrected pre-treatment body image, and then applying the position offset and a rotation offset to the body-model (or a plurality of position offset and rotation offset to a plurality of partitions of the body-model or a deformation model to the body-model) enhanced corrected pre-treatment body image to create the re-positioned corrected pre-treatment body image. The body-model may be a mathematical model that determines an enhanced location estimate for a second set of body features based on the relative position of the body-model reference features (or markers) in the treatment body image. The second set of body features may be features that are not available, or have poor quality or resolution in the treatment image.

In another embodiment, the best-fit process to create an enhanced treatment body image can include identifying a first set of body-model reference features in the treatment image, identifying from a plurality of secondary pre-treatment images a subset of two or more closest fit images wherein the relative position of the body-model reference features in the closest fit secondary pre-treatment images is close to the relative position of the body-model reference features in the treatment image.

In some embodiments the two of more closet fit secondary pre-treatment images are processed to create an improved closest fit pre-treatment body image. In some embodiments the processing comprises one or more of interpolation, extrapolation, or any other functional fitting model.

In some embodiments the best-fit process to create an enhanced treatment body image can include identifying a first set of body-model reference features in the treatment image, identifying from a plurality of secondary pre-treatment images a subset of two or more closest fit images wherein the relative position of the body-model reference features in the closest fit secondary pre-treatment images is close to the relative position of the body-model reference features in the treatment image, applying an interpolation algorithm to two or more secondary pre-treatment images to create an improved interpolated closest fit pre-treatment body image.

In some embodiments the best-fit process to create an enhanced treatment body image can include identifying a first set of body-model reference features in the treatment image, identifying from a plurality of secondary pre-treatment images a subset of two or more closest fit images wherein the relative position of the body-model reference features in the closest fit secondary pre-treatment images is close to the relative position of the body-model reference features in the treatment image, applying an interpolation algorithm to two or more secondary pre-treatment images to create an improved interpolated closest fit pre-treatment body image and then applying the position offset and a rotation offset to (or applying a plurality of position offset and/or rotation offset to a plurality of portions of the body image or applying a deformation model to the body image) the improved interpolated closest fit corrected pre-treatment body image to create the re-positioned corrected pre-treatment body image. In some embodiments the plurality of pre-treatment secondary images may be generated from a 3D imaging vs. time (for example from a 4D CT for imaging a patient while breathing). In some embodiments the plurality of pre-treatment secondary images may be generated from a 3D imaging vs. patient positioning.

Adaptive Timing of Imaging

In some embodiments a radiation treatment system comprises an imaging element (or imaging elements) for assisting in delivering radiation doses, for example an Image Guided Radiation Therapy (IGRT) system. In some embodiments the imaging element is a diagnostic imaging element. In some embodiments the imaging element is a treatment imaging element. In some embodiments the imaging element is a pre-treatment imaging element. In some embodiments the radiation treatment system comprises a radiation treatment beam element. In some embodiments the radiation treatment system comprises a patient table (wherein table may be replaced by couch or other furniture for positioning a patient comprising a VOI). In some embodiments the patient table is adjustable based on the imaging element information. In some embodiments the radiation treatment comprises one or more of radiation therapy or radiation surgery. In some embodiments the imaging element comprises a source that directs radiation at a patient comprising a VOI. In some embodiments the imaging element generates a measurement (wherein the term measurement may be exchanged by one or more of the terms: an observation, an image, an image data, imaging data, a scan, a scan data, a file, a computer display signal, a printout, an array of values comprising information associated with the VOI.

In some embodiments the imaging radiation doses are low, but a large number of imaging observations are required during radiation treatment resulting in a significant cumulative radiation dose on the patient. In some embodiments it is advantageous to reduce the number of imaging observations required during radiation treatment by using adaptive timing (or time or sampling) of imaging (or alternatively by selecting or determining the time of an imaging or imaging observation). In some embodiments adaptive timing of imaging observations reduces side effects from the radiation treatment on healthy tissue. In some embodiments adaptive timing of imaging observations reduces the energy consumption of die radiation treatment system or increases the life expectancy of the imaging element.

In some embodiments adaptive timing of imaging assists in positioning a VOI. In some embodiments adaptive timing of imaging for positioning of the VOI enables higher doses of radiation to a target tissue or faster treatment or less fractions. In some embodiments adaptive timing of imaging for positioning of the VOI reduces side effects of radiating adjacent healthy tissue. In some embodiments adaptive timing of imaging for positioning of the VOI is enhanced (wherein enhanced may include one or more of increased accuracy, reduced error, simplified imaging, etc.) by using one or more natural or artificial objects (for example active or passive markers or sensors or detectors), in or on the patient, in or near the VOI. At least some embodiments include adaptive timing of imaging for positioning of the VOI images of at least a part of the VOI. In some embodiments adaptive timing of imaging for positioning of the VOI comprises a region of the patient that is larger than the VOI. In some embodiments the VOI comprises a deceased tissue. In some embodiments the VOI comprises healthy tissue. In some embodiments the VOI comprises a tissue that should be avoided when delivering radiation doses. In some embodiments a radiation parameter associated with the adaptive timing of imaging is desired to be below a threshold. In some embodiments the radiation parameter is one of more of the radiation intensity, a radiation dose, a cumulative radiation, and effective biological radiation, etc. In some embodiments the adaptive timing of imaging element comprises one or more of a camera, a video, an x-ray, MRI, CT, CBCT, ultrasound, PET. In some embodiments the radiation treatment system comprises a processor for estimating a positioning of the VOI based in part on one or more imaging element observations. In some embodiments the radiation treatment system comprises a processor for estimating a future positioning of the VOI based in part on one or more imaging element observations. In some embodiments the radiation treatment system comprises a processor for estimating a future positioning of the VOI based in part on one or more imaging element observations to compensate for a latency (wherein latency could be a lag or a delay) in the radiation treatment system. In one embodiment one or more latencies are due to one or more of imaging observation, imaging processing, processor estimation computations, radiation treatment system repositioning. In some embodiments the one or more latencies are constant. In some embodiments the one or more latencies are variable. In some embodiments the one or more latencies are variable as a function of the radiation treatment system state. In some embodiments the one or more latencies are estimated during the treatment. In some embodiments the one or more latencies are calibrated prior to treatment. In some embodiments the adaptive timing of imaging are based on the one or more latencies.

In some embodiments the radiation treatment system estimates a future positioning of the VOI based in part on one or more imaging element observations to determine a timing of a new imaging observation. In some embodiments the estimation of a future positioning of the VOI is based on well-known methods (wherein methods may be exchanged for functions, techniques, models, equations, etc.). In some embodiments a method for estimating a future positioning includes a linear predictor (for example linear regression) based on prior one or more imaging element observations. In some embodiments a method for estimating a future positioning includes a nonlinear predictor (for example artificial neural networks) based on prior one or more imaging element observations. In some embodiments a method for estimating a future positioning includes internal state based linear predictors (for example Kalman filtering) based on prior one or more imaging element observations. Other methods for estimating a future positioning may be used, such as polynomial models, motion equations, etc.

In some embodiments the method for estimating a future positioning includes one or more parameters wherein parameters may be exchanged for coefficients, modes, weights, etc.). In some embodiments the parameters are constant (for example if the positioning of the VOI follows a stationary process). In some embodiments the parameters are estimated based in part on initial (for example during a training phase) imaging element observations and are kept constant for a subsequent set of imaging element observations. In some embodiments the parameters are adjusted over time. In some embodiments the parameters are adjusted over time (for example time varying parameters) based in part on imaging element observations.

In some embodiments the radiation treatment system estimates two or more future positioning of the VOI at two or more future time instances based in part on one or more imaging element observations to determine a timing of a new imaging observation. For example, the positioning of the VOI could be estimated for a future time t1, and future time t2>t1. If the positioning of the VOI is estimated to change by less than a threshold, imaging may be avoided (reduced observations) until a future time t3 greater than t2.

In some embodiments, if a positioning parameter (for example a change or rate of change in a positioning) of the VOI is estimated to be less than a threshold for a future time t1 and above a threshold for a future time t2, imaging may be avoided (reduced observations) until a future time T1, but a new timing of imaging will be required before future time t2. In some embodiments the radiation treatment system has a latency TL (wherein latency may be exchanged for delay or lag) and the new imaging observation will be required at time Tth-TL, wherein Tth is the future time when the positioning is estimated to cross a threshold.

In some embodiments the radiation treatment system estimates a plurality of positionings of the VOI based in part on the same one or more imaging element observations. In some embodiments the radiation treatment system estimates a plurality of positionings of the VOI each at one of a plurality of time instances based in part on the same one or more imaging element observations. In some embodiments the radiation treatment system estimates a plurality of positionings of the VOI based on a plurality of estimation methods (for example linear and nonlinear methods) based in part on the same one or more imaging element observations. In some embodiments the radiation treatment system estimates a plurality of positionings of the VOI based on an estimation methods with a plurality of parameter choices (for example selecting different phases of a cyclostationary based method) based in part on the same one or more imaging element observations.

In some embodiments the radiation treatment system estimates a plurality of positionings of the VOI based in part on the same one or more imaging element observations to determine a positioning path of the VOI in some embodiments the positioning path of the VOI comprises one or more of a location path, orientation path, angle path, deformation path, transformation path, rotation path. In some embodiments the radiation treatment system estimates a plurality of positionings of the VOI at a plurality of time instances (*herein at least one first positioning is estimated at a different time instance than a second positioning) based in part on the same one or more imaging element observations to determine a positioning path of the VOI.

In some embodiments the plurality of time instances is selected such that a positioning of the VOI at a different time instance may be derived (wherein derived may be estimated, interpolated, extrapolated, etc.) from the plurality of positionings of the VOI. For example positioning may be determined at times {t1, t2, t3}, wherein t1<t2<t3 such that for any time t, such that t1<t<t3 a positioning may be derived.

In some embodiments the radiation treatment system estimates a plurality of positionings of the VOI at a given time (for example current time) based in part on one or more imaging element observations. In some embodiments the radiation treatment system estimates a plurality of positionings of the VOI at a plurality of time instances at a given time instance (for example current time) based in part on one or more imaging element Observations.

In some embodiments the radiation treatment system estimates a plurality of positionings of the VOI based on a plurality of estimation methods (for example linear and nonlinear methods) at a given time instance (for example current time) based in part on one or more imaging element observations. In some embodiments the radiation treatment system estimates a plurality of positionings of the VOI based on an estimation methods with a plurality of parameter choices (for example selecting different phases of a cyclostationary based method) at a given time instance (for example current time) based in part on one or more imaging element observations.

In some embodiments the radiation treatment system estimates a plurality of positionings of the VOI at a given time instance (for example current time) based in part on one or more imaging element observations to determine a positioning path of the VOI.

In some embodiments the radiation treatment system estimates a plurality of positionings of the VOI at a plurality of time instances (wherein at least one first positioning is estimated at a different time instance than a second positioning) at a given time instance (for example current time) based in part on one or more imaging element observations to determine a positioning path of the VOI.

In some embodiments the plurality of time instances is selected such that a positioning of the VOI at a different time instance may be derived (wherein derived may be estimated, interpolated, extrapolated, etc.) from the plurality of positionings of the VOI. For example positioning may be determined at times {t1, t2, t3}, wherein t1<t2<t3 such that for any time t, such that t1<t<t3 a positioning may be derived.

In some embodiments the radiation treatment system estimates a plurality of future positioning of the VOI based in part on the same one or more imaging element observations. In some embodiments the radiation treatment system estimates a plurality of future positioning of the VOI at a plurality of time instances based in part on the same one or more imaging element observations. In some embodiments the radiation treatment system estimates a plurality of future positioning of the VOI based on a plurality of estimation methods (for example linear and nonlinear methods) based in part on the same one or more imaging element observations. In some embodiments the radiation treatment system estimates a plurality of future positioning of the VOI based on an estimation methods with a plurality of parameter choices (for example selecting different phases of a cyclo-stationary based method) based in part on the same one or more imaging element observations. In some embodiments the radiation treatment system estimates a plurality of future positioning of the VOI based in part on the same one or more imaging element observations to determine a positioning path of the VOI. In some embodiments the radiation treatment system estimates a plurality of future positioning of the VOI at a plurality of time instances (wherein at least one first future positioning of the VOI is estimated at a different time instance than a second future positioning) based in part on the same one or more imaging element observations to determine a positioning path of the VOI.

In some embodiments the plurality of time instances is selected such that a future positioning of the VOI at a different time instance may be derived (wherein derived may be estimated, interpolated, extrapolated, etc.) from the plurality of future positioning of the VOI. For example positioning may be determined at future times {t1, t2, t3}, wherein t1<t2<t3 such that for any time t, such that t1<t<t3 a positioning may be derived.

In some embodiments the radiation treatment system estimates a plurality of future positioning of the VOI at a given time instance (for example current time) based in part on one or more imaging element observations. In some embodiments the radiation treatment system estimates a plurality of future positioning of the VOI at a plurality of time instances at a given time instance (for example current time) based in part on one or more imaging element observations.

In some embodiments the radiation treatment system estimates a plurality of future positioning of the VOI based on a plurality of estimation methods (for example linear and nonlinear methods) at a given time instance (for example current time) based in part on one or more imaging element observations. In some embodiments the radiation treatment system estimates a plurality of future positioning of the Val based on an estimation methods with a plurality of parameter choices (for example selecting different phases of a cyclostationary based method) at a given time instance (for example current time) based in part on one or more imaging element observations.

In some embodiments the radiation treatment system estimates a plurality of future positioning of the VOI at a given time instance (for example current time) based in part on one or more imaging element observations to determine a positioning path of the VOI. In some embodiments the radiation treatment system estimates a plurality of future positioning of the VOI at a plurality of time instances (wherein at least one first future positioning of the VOI is estimated at a different time instance than a second future positioning) at a given time instance (for example current time) based in part on one or more imaging element observations to determine a positioning path of the VOI.

In some embodiments the plurality of time instances is selected such that a future positioning of the VOI at a different time instance may be derived (wherein derived may be estimated, interpolated, extrapolated, etc.) from the plurality of future positioning of the VOI. For example positioning may be determined at future times {t1, t2, t3}, wherein t1<t2<t3 such that for any time t, such that T1<t<T3 a positioning may be derived. In some embodiments polynomial (for example linear) interpolation of the positioning at times {t1, t2, t3}, is used to interpolate the positioning for any time t, such that t1<t<t3.

In some embodiments the radiation treatment system estimates a future positioning parameter, wherein the positioning parameter is positioning error of the VOI based in part on one or more imaging element observations to determine a timing of a new imaging observation, In some embodiments the positioning error of the VOI is one of more of: a max error, an error interval, a positioning interval, an error interval between a max of the positioning parameter and a min of the positioning parameter, an error pdf, an error cdf, a probability the error will be lower than a threshold, a mean square error, and error norm relative to a threshold, etc.

In some embodiments the estimation of a positioning error of the VOI is based on well-known methods (wherein methods may be exchanged for techniques, models, equations, etc.). In some embodiments a method for estimating a positioning error includes a linear predictor (for example linear regression) based on prior one or more imaging element observations. In some embodiments a method for estimating a positioning error includes a nonlinear predictor (for example artificial neural networks based on prior one or more imaging element observations. In some embodiments a method for estimating a positioning error include internal state based linear predictors (for example Kalman filtering) based on prior one or more imaging element observations.

Other methods for estimating a positioning error may be used, such as polynomial models, motion equations, etc.

In some embodiments the method for estimating a positioning error includes one or more parameters (wherein parameters may be exchanged for coefficients, modes, weights, etc.). In some embodiments the parameters are constant (for example if the positioning error of the VOI follows a stationary process). In some embodiments the parameters are estimated based in part on initial (for example during a training phase) imaging element observations and are kept constant for a subsequent set of imaging element observations. In some embodiments the parameters are adjusted over time. In some embodiments the parameters are adjusted over time (for example time varying parameters) based in part on imaging element observations.

In some embodiments the radiation treatment system estimates two or more positioning error of the VOI at two or more future time instances based in part on one or more imaging element observations to determine a timing of a new imaging observation. For example, the positioning error of the VOI could be estimated for a future time t1, and future time t2>t1. In some embodiments, if the positioning error of the VOI is estimated to be less than a threshold for both future time t1 and t2, imaging may be avoided (reduced observations) until a future time t3 greater than t2. In some embodiments, if the positioning error of the VOI is estimated to be less than a threshold for a future time t1 and above a threshold for a future time t2, imaging may be avoided (reduced observations) until a future time t1, but a new timing of imaging will be required before future time t2.

In some embodiments the radiation treatment system has a latency TL and the new imaging will be required at time Tth-L, wherein Tth is the future time when the positioning error of the VOI is estimated to cross a threshold.

In some embodiments the radiation treatment system estimates a plurality of positioning error of the VOI at a plurality of time instances based in part on one or more imaging element observations to determine a positioning error path of the VOI. In some embodiments the plurality of time instances is selected such that a positioning error at a different time instance may be derived (wherein derived may be estimated, interpolated, extrapolated, etc.) from the plurality of positioning error of the VOI. For example positioning error may be determined at future times $\{t1, t2, t3\}$, wherein t1<t2<t3 and any time t, such that t1<t2<t3 may be derived. In some embodiments polynomial (for example linear) interpolation of the positioning error of the VOI at times $\{t1, t2, t3\}$ is used to interpolate the positioning error for any time t, such that t1<t<t3.

In some embodiments the radiation treatment system estimates a positioning and a positioning error of the VOI based in part on one or more imaging element observations to determine a timing of a new imaging observation. In some embodiments the radiation treatment system estimates a future positioning and a positioning error of the VOI based in part on one or more imaging element observations to determine a timing of a new imaging observation.

In some embodiments the positioning of the VOI comprises information associated with one or more of a location (for example in Cartesian coordinates), an orientation (for example by specifying azimuth and elevation angles relative to a location), an angle, a deformation of the VOI, a velocity, an acceleration, a location error, an orientation error, an angel error, a deformation error, a velocity error, an acceleration error. In some embodiments the positioning of the VOI comprises information associated with a change of one or more of a location (for example a velocity vector), an orientation (for example a rigid body rotation speed around an axis), an angle, a deformation of the VOI or an error metric associated with a change.

In some embodiments the information associated with a change of the VOI positioning comprises one or more of: a velocity, a slope, an acceleration, a path, etc. For example, the positioning of the VOI may comprise the VOI location, velocity, and acceleration (could be 3D or projected onto a 2D plane) at a time instance. In some embodiments the positioning of the VOI comprise positioning information of a point of the VOI (for example center of mass, or center of volume, or center of diseased tissue, etc.). In some embodiments the positioning of the VOI comprises positioning information of a marker natural or artificial, in, near or on the body or equivalently a sensor or object) associated with the VOI (for example in or near a diseased tissue in the VOI. In some embodiments positioning information of the VOI comprises positioning information of a plurality of points associated with the VOI. In some embodiments positioning information of the VOI comprises positioning information of a surface associated with the VOI. In some embodiments positioning information of the VOI comprises positioning information of a calibration object associated with the VOI.

In some embodiments adaptive timing of an imaging observation results in imaging observations performed at non-uniform time intervals. In some embodiments adaptive timing of an imaging observation is performed at three consecutive time instances $\{t1, t2, t3\}$, where t1<t2<t3, such that t2−t1 is larger than t3−t2 by at least 10% (for example (t2−t1)/(t3−t2)>1.1). In some embodiments adaptive timing of an imaging observation is performed at three consecutive time instances $\{t1, t2, t3\}$, where t1<t2<t3, such that t2−t1 is smaller than t3−t2 by at least 10% (for example (t2−t1)/(t3−t2)>10.9).

In some embodiments adaptive timing of an imaging observation based on VOI positioning (for example one or more of determined, computed, predicted or estimated VOI positioning) results in imaging observations performed at non-uniform time intervals. In some embodiments, if a future VOI positioning is similar (for example relative to a threshold) to a current VOI positioning an imaging observation may be delayed (wherein delayed maybe exchange for postponed, prevented, avoided, rate decreased, frequency decreased, period increased, etc.). For example, if a current or future VOI positioning velocity is low (for example relative to a threshold) an imaging observation may be delayed (wherein reduced maybe exchange for postponed, prevented, avoided, etc.). For example, if a future VOI positioning is far (for example above a threshold) from a current VOI positioning an imaging observation may be increased (wherein increased maybe exchange for prioritized, accelerated, etc.).

In some embodiments, if the difference between a future VOI positioning and a current VOI positioning is above a threshold an imaging observation may be accelerated (wherein accelerated maybe exchange for prioritized, scheduled immediately, scheduled asap, etc.). In some embodiments, the difference between a future VOI positioning and a current VOI positioning is compared relative to a threshold. In some embodiments, based on the comparison relative to the threshold an imaging observation period (or rate) may be increased or decreased.

In some embodiments, the difference between two or more future VOI positioning is compared relative to a threshold. In some embodiments, based on the comparison relative to the threshold an imaging observation period (or rate) may be increased or decreased. In some embodiments, the difference between a future VOI positioning and a past VOI positioning is compared relative to a threshold. In some embodiments, based on the comparison relative to the threshold an imaging observation period (or rate) may be increased or decreased. In some embodiments, the difference between two or more past VOI positioning is compared relative to a threshold. In some embodiments, based on the comparison relative to the threshold an imaging observation period (or rate) may be increased or decreased.

In some embodiments, the difference between a VOI positioning and a RTS configuration is compared (for example radiation beam or patient couch elements) relative to a threshold (for example a dose irradiation threshold). In some embodiments, based on the comparison relative to the threshold an imaging, observation period (or rate) may be increased or decreased.

In some embodiments adaptive timing of an imaging observation based on VOI positioning errors results in imaging observations performed at non-uniform time intervals, F r example, if a future VOI positioning error of the VOI is small (for example relative to a threshold) an imaging observation may be reduced (wherein reduced maybe exchange for postponed, prevented, avoided, etc.). For example, if a current or future VOI positioning velocity error is low (for example relative to a threshold) an imaging observation may be reduced (wherein reduced maybe exchange for postponed, prevented, avoided, etc.). For example, if a future VOI positioning error of the VOI is large (for example above a threshold) an imaging observation may be increased (wherein increased maybe exchange for prioritized, accelerated, etc.).

In some embodiments adaptive timing of an imaging observation results in imaging observations performed at non-uniform time intervals that are roughly an integer multiple of a time unit. In some embodiments adaptive timing of an imaging observation is performed at time instances {k(1)*T, k(2)*T, k(3)*T, . . . , k(n)*T}, wherein k(1)<k(2)< k(3)< . . . <k(n) are integers and at least one k(p)>k(p−1)+1. In some embodiments, the integers k(p−1) and k(p) are not consecutive integers for some time index 'p'. In some embodiments, when k(p)>k(p−1)+1, the imaging observation at the time (k(p−1)+1)*T is skipped (or prevented, or avoided, etc.), resulting in a reduction of imaging observations. In some embodiments, adaptive timing of an imaging observation at roughly an integer multiple of a time unit, simplifies estimation of a positioning. In some embodiments, imaging observations are taken at time instances {t1, t2, t3}, such that t1<t2<t3 and t2−t1~=q*T and t3−t2~=p*T, and 'q' and 'p' are different integers and '~=' represents the approximately equal operand. In some embodiments the '~=' is used to represent small errors due to one or more of clock reference errors (for example jitter in PLL) or HW or SW execution time variation.

In some embodiments adaptive timing of an imaging observation is constrained by a method for estimating positioning of a VOI based on an object associated with the VOI (or the VOI). In some embodiments the method for estimating the VOI positioning requires an imaging observation that is current within Tc seconds of the VOI positioning desired time. In some embodiments if the most recent imaging observation was collected at time t1 and current time is t>t1+Tc then a new imaging observation shall be scheduled (or initiated or instructed or a command/configuration must be issued).

In some embodiments, a radiation treatment system latency TL is included in the adaptive timing of an imaging observation, and if current time is denoted t, whenever t>t1+Tc−TL, a new imaging observation is scheduled. In some embodiments the method for estimating positioning of a VOI based on an object associated with the VOI (or the VOI) comprises a parameter for selecting between 2 or more modes. In some embodiments the 2 or more modes differ on an imaging observation lag (or alternatively latency, delay, offset). For example mode #1 may estimate positioning of the VOI at time t based on imaging at times t-t1 and t-t2 and mode #2 may estimate positioning at time t based on imaging at times t-t3 and t-t4. In some embodiments, timing of a new imaging observation is based on an imaging observation lag required for estimating a positioning of the VOI.

In some embodiments an positioning of the VOI is re-estimated (or alternatively re-evaluated, refined, re-computed, re-determined) based on additional imaging element observations. In some embodiments the method for estimating a positioning, estimates a future positioning, and over time as additional imaging observations become available the future positioning may be refined based on additional imaging observations collected after the initial future time, hu some embodiments the re-estimated positioning of the VOI is used to refine a positioning parameter, for example one or more of a positioning, positioning error, positioning method coefficients, etc.

In some embodiments adaptive timing of an imaging observation for positioning of a VOI assists insetting (wherein setting may be replaced by one or more of configuring, programming, specifying) a radiation treatment system element of the RTS. In some embodiments adaptive timing of an imaging observation for positioning of an object associated with the VOI assists in setting (wherein setting may be replaced by one or more of configuring, programming, specifying) a radiation treatment system element of the RTS relative to the VOI. In some embodiments adaptive timing of an imaging observation for positioning of an object associated with the VOI assists in setting (wherein setting may be replaced by one or more of configuring, programming, specifying) a RTS parameter. In some embodiments adaptive timing of an imaging observation for positioning of an object associated with the VOI assists in setting (wherein setting may be replaced by one or more of configuring, programming, specifying) a RTS element relative to the VOI.

In some embodiments the RTS element parameter is one or more of a beam assembly setting, imaging element setting, beam positioning, a beam location, a beam intensity, a beam shape, one or more subbeams of the beam, an external field directing the beam, a beam size, a beam orientation, adjusting one or more beam multi-leaf collimators, setting an imaging element, setting a beam assembly, setting of a patient couch, setting of the VOI or the patient associated with the VOI. In some embodiments the VOI is re-positioned relative to the RTS by modifying the positioning of the patient comprising the VOI or by moving the patient or the patient table (or equivalently a patient couch, or other patient furniture, etc.) associated with the patient of the radiation treatment system.

In some embodiments an imaging observation for positioning of an object associated with the VOI assists in setting (or alternatively configuring, commanding, etc.) a RTS relative to the VOI. In some embodiments, the setting the RTS relative to the VOI results in a RTS path is a discrete-time plurality (or a set) of RTS relative to the VOI. In some embodiments, the setting the RTS relative to the VOI results in a RTS path is a continuous-time function of RTS relative to VOI. In some embodiments the VOI positioning information results in a sequence of discrete-time or continuous-time settings for the radiation treatment system (for example beam source settings, beam filtering settings, patient table settings, etc.) and the RTS relative to the VOI positioning is estimated.

In some embodiments the VOI positioning information results in discrete-time or continuous-time settings for the radiation treatment system (for example beam source settings, beam filtering settings, patient table settings, etc.) and the RTS relative to the VOI positioning is estimated based on the radiation treatment system dynamic response to the settings. In some embodiments the VOI positioning information results in discrete-time or continuous-time settings for the radiation treatment system (for example beam source settings, beam filtering settings, patient table settings, etc.) and the RTS relative to the VOI positioning is estimated based on the radiation treatment system dynamic response to the settings relative to the positioning path of the VOI. In some embodiments the VOI positioning information results in discrete-time or continuous-time settings for the radiation treatment system (for example beam source settings, beam filtering settings, patient table settings, etc.) and the RTS relative to the VOI positioning is estimated based on the radiation treatment system dynamic response to the settings and when the RTS relative to the VOI positioning is above a threshold the RTS commands (or alternatively configurations or settings, etc.) are modified. In some embodiments the radiation command modification comprises preventing the RTS from irradiating the patient comprising the VOI.

In some embodiments the determined VOI positioning comprises a quality metric associated with the imaging observation. In some embodiments the quality metric is obtained from jointly processing a plurality of imaging observations. In some embodiments the adaptive timing of imaging includes a constraint based on a plurality of imaging observations quality metric restriction. In some embodiments the plurality of imaging observations must satisfy a criteria (for example resolution, contrast, registration metrics relative to a pre-treatment imaging, minimum time instance spacing) relative to a threshold that adaptively modifies the time instances for timing of additional imaging observations. In some embodiments the quality metric is obtained from comparing an imaging observation relative to a pre-treatment imaging. In some embodiments the pre-treatment imaging is of higher quality (for example higher resolution, higher dimensionality, larger field of view, etc.) than the imaging element. In some embodiments the pre-treatment imaging is one or more of CT, MRI, 3D imaging, 4D imaging, PET, ultrasound. In some embodiments the determined VOI positioning comprises a quality metric (for example a statistical parameter, a confidence level, a confidence interval, etc.) which is further utilized to adapt the timing of additional imaging observations.

Figure 13:
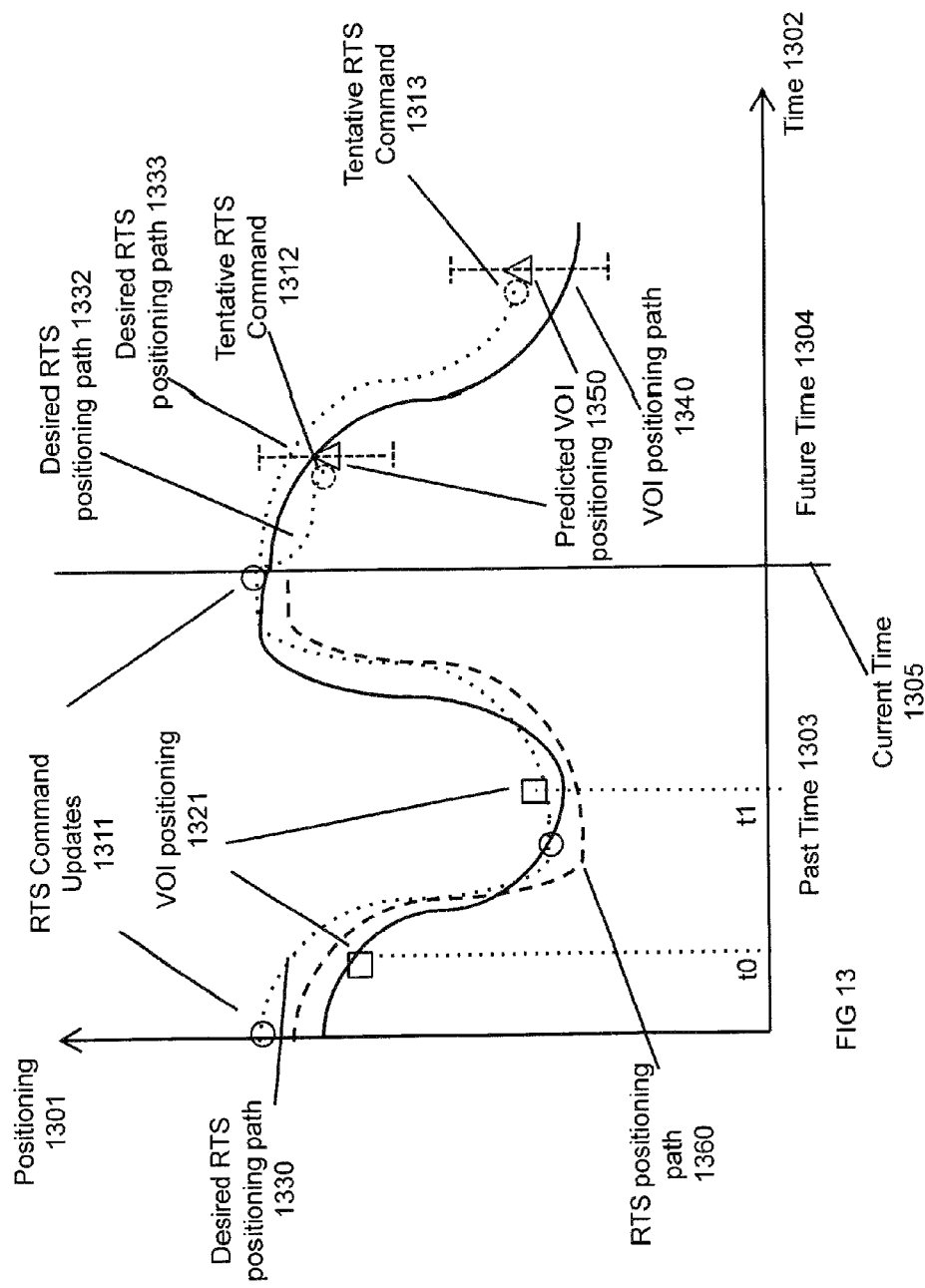
FIG. 13 is an illustration of an image guided radiation treatment system according to an embodiment.

FIG. 13 is an illustration of an image guided radiation treatment system according to an embodiment. In FIG. 1B, the horizontal axis represents time 1302, which could include one or more of past time 1303, future time 1304 and current time 1305 (shown has the vertical line separating past time from future time) and times t0 and t1. In FIG. 13 the vertical axis represents a positioning 1301 (or equivalently a positioning parameter amount or positioning parameter value or positioning parameter quantity, etc.). The positioning could be a location (for example one or more of 3 Cartesian coordinates), a velocity, an acceleration, an orientation (for example elevation angle or an angle within a ring gantry), an angle, a size, a shape, a MLC setting, a dose, a rotation, or an error metric of one or more of a location, a velocity, an acceleration, and orientation, an angle, a size, a shape, a MLC setting, a does a rotation, etc. The positioning parameter could be associated to one or more VOI (or the patient comprising the VOI) or one or more elements of the radiation treatment system (one or more of a radiation beam, beam assembly, patient couch, one or more imaging elements, etc.). In FIG. 13 the positioning illustration has one parameter (for example x-dimension), hut in general the positioning could have multiple parameters (for example a projection of a VOI in 2 dimensions).

To simplify the discussion, the positioning of the VOI and the positioning of a radiation treatment system configuration have been included in the FIG. 13. In some embodiments the positioning of the VOI and the positioning of the radiation treatment may be different parameters (for example 2D Cartesian coordinates for a VOI and an angle for a beam assembly gantry). In some embodiments the positioning of the VOI may be transformed to compare the positioning with the radiation treatment system configuration parameters (for example the MLC settings may be projected onto a VOI imaging observation).

In FIG. 13 the VOI positioning path 1340 (shown as a continuous line) represents a VOI positioning parameter value vs. time. The VOI positioning path 1340 is represented as a continuous-time parameter value vs. time, but could have been a discrete-time parameter (for example a uniform or non-uniform set of points/values versus time. In FIG. 13 the radiation treatment system (RTS) positioning 1360 (shown as a dashed line) represents a RTS positioning (parameter value) vs. time. In FIG. 13 the desired RTS positioning path 1330 (shown as a dotted line) represents a desired RTS positioning path (parameter value) vs. time. In FIG. 13 the RTS command (wherein command may be exchanged for configuration) updates 1311 (shown as circles) represents one or more commands provided to RTS elements (for example for beam assembly positioning or couch positioning), typically from one or more processors to assist in RTS positioning (parameter value) vs. time. The RTS commands could be discrete-time commands (as shown in FIG. 13), but could also be continuous-time commands. In FIG. 13 the VOI positioning 1321 (shown as squares) represent one or more estimates of the VOI positioning based on a imaging observation (and typically processed by one or more processors). In FIG. 13 the VOI positioning squares are shown close (but not necessarily on top of) to the VOI positioning path 1340.

Predicted (wherein predicted could be replaced by estimated or determined or computed) VOI positioning 1350 (shown as a triangle inside a vertical interval) represent one or more future instances at which the positioning of the VOI are predicted (where in predicted may be exchanged with estimated or determined). In some embodiments the predicted VOI positioning 1350 is based on imaging observations (for example imaging at times t0 or t1). In some embodiments the predicted VOI positioning 1350 is based on imaging observations (for example imaging at times t0 or t1 or VOI positioning 1321) and a constraint on the VOI positioning. In some embodiments the VOI positioning constraint is based on a functional model (for example a body model). In some embodiments the VOI positioning constraint is based on a pre-treatment imaging observation. The predicted VOI positioning 1350 includes a triangle to represent a VOI positioning value (for example a mean or maximum likelihood value) and an interval to VOI positioning range (or equivalently to represent an error on the VOI positioning value or a VOI positioning uncertainty interval or a VOI positioning confidence interval). FIG. 13 also includes two future RTS command (or configuration, setting, etc.) updates alternatives (wherein alternatives may be replaces by one or more choices) and the associated desired RTS positioning paths, desired RTS positioning path 1332 and desired RTS positioning path 1333. In some embodiments the RTS positioning path comprise one or more of a RTS element (for example a subsystem or element such as the beam assembly or the patient couch) location path, orientation path, angle path, MLC path, radiation dose path, intensity path, subbeam shape path, subbeam on/off path. In some embodiments the RTS command comprises setting one or more of a RTS parameter, such as RTS beam or beam assembly parameter (position, orientation, angle, size, shape, intensity, dose, MLC), patient couch, or adjusting a patient positioning posture, location, orientation, etc.).

In some embodiments the RTS predicts a plurality of VOI positioning at a given time, and determines a plurality of tentative RTS commands (such as 1312 and 1313 shown as dotted circles) and selects one of the plurality of tentative RTS commands. In some embodiments the RTS applies the selected RTS command to an appropriate RTS element or subsystem. In some embodiments the RTS computes (or alternatively determines or estimates, etc.) a VOI positioning path based on the VOI positioning 1350 and computes a RTS element path and/or a plurality of tentative RTS commands. In some embodiments the RTS computes a VOI positioning path based on the predicted VOI positioning 1350 and computes a RTS positioning path for a plurality of tentative RIS commands and compares the VOI positioning path relative to the plurality of RTS positioning paths. In some embodiments the RTS computes plurality of a RTS positioning paths for a plurality of RTS commands and compares the predicted VOI positioning 1350 relative to the plurality of RTS positioning paths. In some embodiments the RTS computes a plurality of RTS positioning path for a plurality of tentative RTS commands and compares the predicted VOI positioning 1350 relative to the plurality of tentative RTS positioning paths and selects a RTS command from the plurality of tentative RTS commands.

In some embodiments the RTS computes a plurality of RTS positioning path for a plurality of tentative RTS commands and compares the predicted VOI positioning 1350 relative to the plurality of RTS positioning paths and selects a RTS command from the plurality of tentative RTS commands based on a RTS positioning path error relative to the predicted VOI positioning 1350 or a predicted VOI positioning path based on the VOI positioning 1350. For example FIG. 13 illustrates two tentative RTS commands choices, tentative RTS command 1312 and tentative RTS command 1313, each with an associated desired RTS positioning path 1332 and desired RTS positioning path 1333. In some embodiments based on an error metric (for example mean square error, max error, max percentile error, norm errors, etc) the desired RTS positioning path may be compared to the predicted VOI positioning 1350. In some embodiments determining a desired RTS positioning path comprises information about a latency (or equivalently a delay or lag) in the RTS. In some embodiments determining a desired RTS positioning path comprises information about a motion dynamic (for example of a motor controlling the beam assembly or the patient couch) of the RTS. In some embodiments determining a desired RIS positioning path comprises information about a second (for example a prior, or past or future) desired RTS positioning path command.

In some embodiments a RTS determines a plurality of predicted VOI positioning 1350 at a plurality of time instances and a RTS command is determined based on the plurality of predicted VOI positioning (for example based on a positioning error metric). In some embodiments the predicted VOI positioning 1350 is based on one or more imaging observations (for example imaging at times t0 or t1 or VOI positioning 1321). In some embodiments a predicted VOI positioning 1350 is recomputed at a later time, (for example after future imaging observations become available) to validate or refine or obtain statistics of the future RTS command selection or computation or choice method. In some embodiments the statistics obtained from re-computing predicted VOI positioning 1350 at a later time are used to refine subsequent predicted VOI positioning 1350 (including error analysis) or refine future RTS command computation or selection or to compensate for a has in subsequent decisions (for example if cumulative doses delivered from past RTS commands have resulted in irradiation with a bias or asymmetry).

Figure 14:
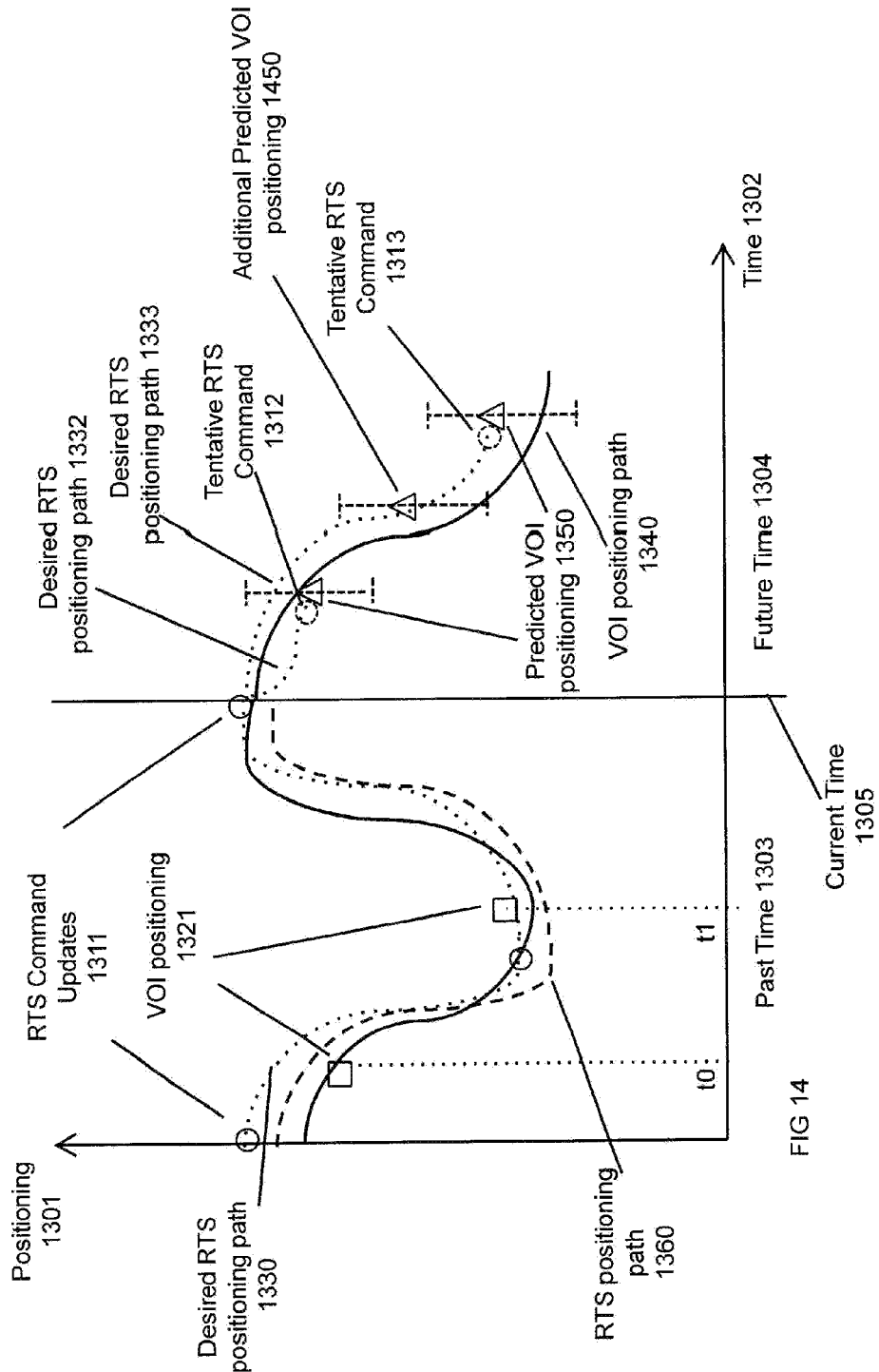
FIG. 14 is an illustration of an image guided radiation treatment system configuration (or command) based on additional predicted VOI positioning 1450 according to an embodiment.

FIG. 14 is an illustration of an image guided radiation treatment system configuration (or command) based on additional predicted VOI positioning 1450 according to an embodiment.

FIG. 14 includes an additional predicted VOI positioning 1450. In some embodiments the additional predicted VOI positioning 1450 is determined based on an imaging observation, such as imaging at time t0 or t1 or VOI positioning 1321. In some embodiments the additional predicted VOI positioning 1450 is based on a different estimation function than predicted VOI positioning 1350.

In some embodiments the additional predicted VOI positioning 1450 is based on a different estimation function than predicted VOI positioning 1350 because it's computed at a different phase of a periodic, quasi-periodic or cyclo-stationary VOI positioning (for example predicted VOI positioning 1350 may be determined at an exhalation phase of a breathing cycle and additional predicted VOI positioning may be determined at an inhalation phase of a breathing cycle). In some embodiments the additional predicted VOI positioning 1450 is determined from the predicted VOI positioning 1350. In some embodiments the additional predicted VOI positioning 1450 is determined based on the predicted VOI positioning 1350 by a functional fitting process, such as an interpolation or an extrapolation. In some embodiments the predicted VOI positioning 1350 are determined such that additional predicted VOI positioning 1450 are determined with a desired target error relative to a threshold. In some embodiments the predicted VOI positioning 1350 are determined at timing instances (for example a sampling period) that enables computation of additional predicted VOI positioning 1450 at any time instance in between the predicted VOI positioning 1350 or between current time and the last time instance of the plurality of predicted VOI positioning 1350. In some embodiments the additional predicted VOI positioning 1450 assists in selecting one of a plurality of future RTS command 1312.

In some embodiments the plurality of predicted VOI positioning 1350 assists in determining a VOI positioning path, for example an estimate of VOI positioning path 1340. In some embodiments, the plurality of predicted VOI positioning 1350 with assistance of one or more additional predicted VOI positioning for example additional predicted VOI positioning 1450) assists in determining a VOI positioning path 1340. In some embodiments the plurality of predicted VOI positioning 1350 assists in determining for alternatively configuring, selecting, etc.) a RTS positioning path, for example desired RTS positioning path 1332 or desired RTS positioning path 1333. In some embodiments the plurality of predicted VOI positioning 1350 with assistance of one or more additional predicted VOI positioning (for example additional predicted VOI positioning 1450) assists in determining a RTS positioning path. In some embodiments the plurality of predicted VOI positioning 1350 with assistance of one or more additional predicted VOI positioning (for example additional predicted VOI positioning 1450) assists in determining a VOI positioning path 1340 and in determining an RTS positioning path. In some embodiments the plurality of predicted VOI positioning 1350 with assistance of one or more additional predicted VOI positioning (for example additional predicted VOI positioning 1450) assists in determining a VOI positioning path 1340 and in determining an RTS positioning path based on comparing the RTS positioning path with the VOI positioning path. In some embodiments the plurality of predicted VOI positioning 1350 with assistance of one or more additional predicted VOI positioning (for example additional predicted VOI positioning 1450) assists in determining a VOI positioning path 1340 and in determining an RTS positioning path based on a path error metric of the RTS positioning path relative to the VOI positioning path.

Figure 15B:
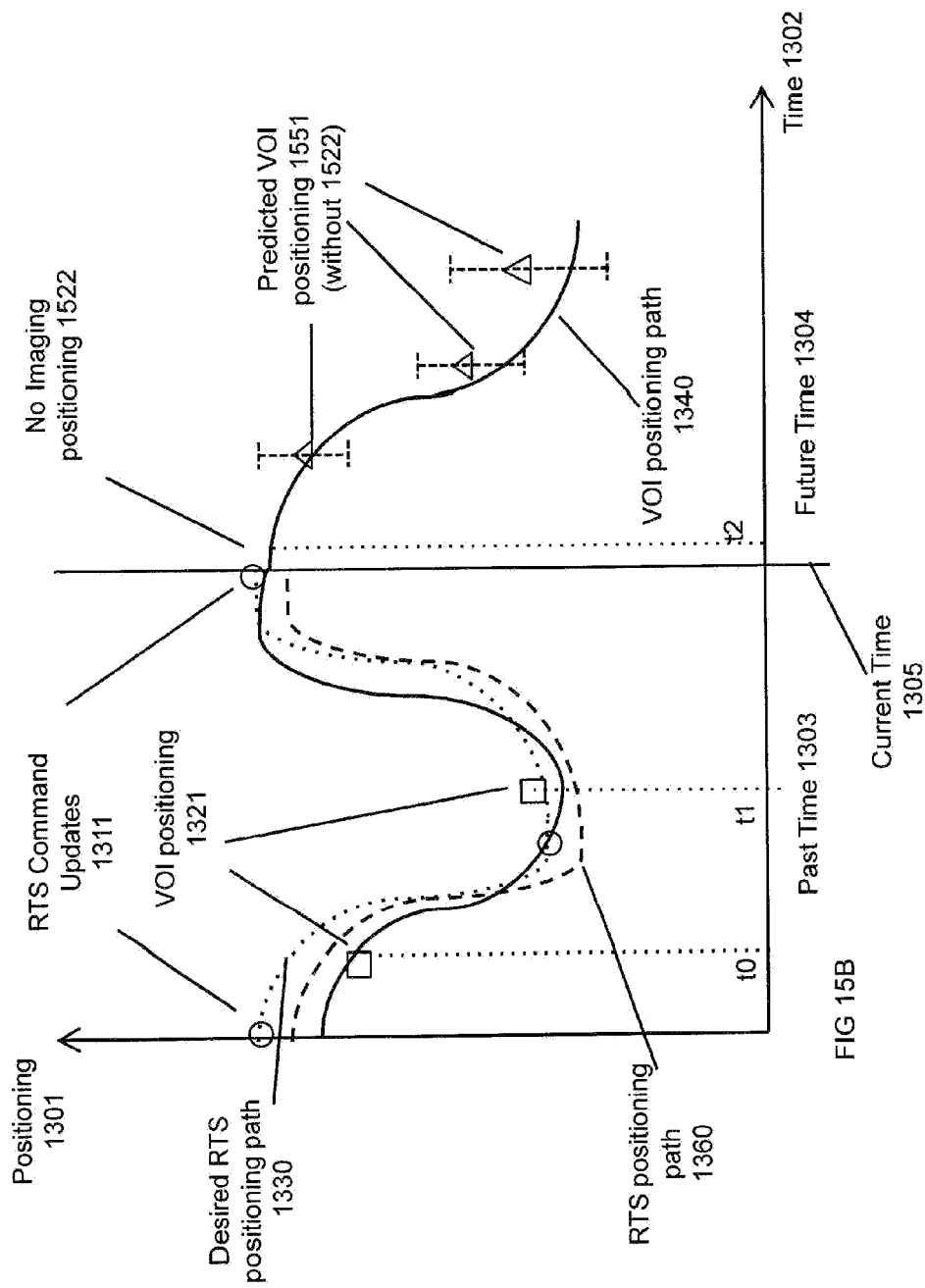

FIG. 15A, 15B illustrate a method for and adaptive (for example reducing) imaging of an image guided radiation treatment system according to an embodiment, FIG. 15A includes a VOI positioning 1522 and predicted VOI positioning 1550 based on imaging observation at time t2. In some embodiments predicted VOI positioning is based on imaging at time t0 or t1 or VOI positioning 1522. In some embodiments predicted VOI positioning is based on imaging at time t0 or t1 or VOI positioning 1522 and prior time imaging at time t0 or t1 or VOI positioning 1321. In some embodiments the imaging at time t2 or VOI positioning 1522 and imaging at time t0 or t1 or VOI positioning 1321 result in approximately equally spaced plurality of imaging or VOI positioning (for example periodic or quasi-periodic timing intervals for imaging observations or processing).

In some embodiments the accuracy (or quality) of the positioning of predicted VOI positioning 1550 is better than required when compared to a threshold (as represented by the predicted VOI positioning 1550 triangles being very close to VOI positioning path 1340 or the VOI positioning 1550 vertical intervals being small). In some embodiments imaging at time t2 or VOI positioning 1522 is not necessary. FIG. 15B is based on FIG. 15A except that imaging at time t2 or VOI positioning 1522 has been skipped (or alternatively avoided, reduced, prevented, saved, etc.). In some embodiments imaging Observations are reduced based on predicted VOI positioning. In some embodiments imaging observations are reduced based on a predicted VOI positioning parameters, such as positioning error or positioning uncertainty or positioning confidence interval. In some embodiments imaging observations are reduced based on a plurality of predicted VOI positioning 1551, for example three or more predicted positioning shown in FIG. 15B. In FIG. 15B the predicted VOI positioning 1551 has larger confidence intervals (or error intervals) relative to the predicted VOI positioning 1550 in FIG. 15A. In some embodiments the predicted VOI positioning 1551 is adequate relative to a threshold and no imaging at time t2 or VOI positioning 1522 is required. In some embodiments reducing imaging observation reduces radiation dose to a patient or a VOI of a patient. In some embodiments the predicted VOI positioning 1551 is based on imaging observations prior to a current imaging observation (for example no imaging observation 1524 and the predicted VOI positioning 1551 quality is sufficient when compared to a threshold.

Figure 15C:
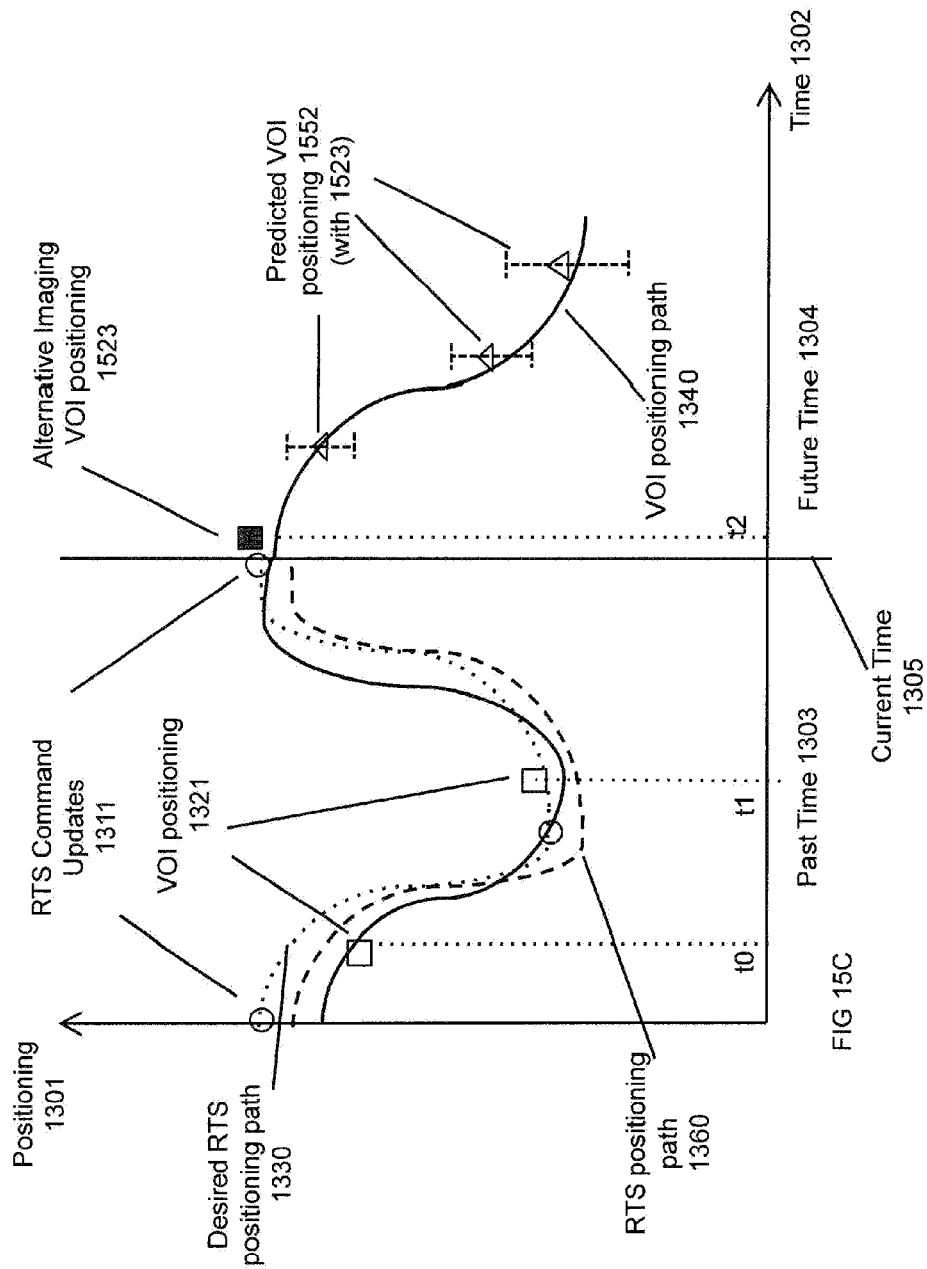
FIG. 15C illustrate a method for alternative (or secondary) imaging of an image guided radiation treatment system according to an embodiment.

FIG. 15C illustrate a method for alternative (or secondary) imaging of an image guided radiation treatment system according to an embodiment. In some embodiments the alternative imaging observation is based on the same imaging element (or subsystem) with an alternative parameter (or setting or configuration or command, etc.). In some embodiments an alternative parameter setting is a different intensity or a different field of view or a different imaging observation size. For example the alternative imaging element setting may include one or more of a lower intensity or a smaller imaging size or a smaller imaging angle. In some embodiments the alternative imaging element setting results in lower radiation doses to at least a portion of a patient or a VOI of a patient. In some embodiments the alternative imaging element is a second imaging element. For example the first imaging element is an x-ray based system and the secondary imaging element is a camera or ultrasound based imaging element.

In some embodiments the predicted VOI positioning 1552 is based on alternative imaging at time t2 or VOI positioning 1523. In some embodiments the predicted VOI positioning 1552 is based on alternative imaging at time t2 or Val positioning 1523 (from the alternative imaging element) and imaging at time t0 or t1 or VOI positioning 1321 (from the primary or original or first imaging element or configuration). In some embodiments the predicted VOI positioning 1552 based in part on alternative imaging at time t2 or VOI positioning 1523 meets a criteria relative to a threshold and imaging positioning at 1522 in FIG. 15A is avoided. In some embodiments the alternative imaging element has one or more of lower resolution, lower radiation, or lower irradiation of at least a portion of a patient. In some embodiments the lower irradiation imaging element is used predominately and the higher irradiation element is used when the predicted VOI positioning parameter is not satisfactory when compared to a threshold. For example the predicted VOI positioning confidence interval is above a max allowed error or large relative to the location of a healthy tissue relative (for example a distance) to diseased tissue. In some embodiments the lower irradiation imaging element is used periodically (or at regular intervals relative to a VOI positioning) and the higher irradiation imaging element is used when the predicted VOI positioning parameter is not satisfactory when compared to a threshold. For example the predicted VOI positioning location confidence interval is above a max allowed error or large relative to the location of a healthy tissue relative (for example a distance) to diseased tissue.

In some embodiments an alternative imaging VOI positioning 1523 is further refined (or alternatively recomputed, re-estimated, etc.) at a future time based on additional information related to VOI positioning path 1340, for example future imaging VOI positioning or future alternative imaging positioning. In some embodiments an alternative imaging VOI positioning 1523 is further refined (or alternatively recomputed, re-estimated, etc.) at a future time based on additional information related to VOI positioning path 1340, for example future imaging VOI positioning or future alternative imaging VOI positioning to estimate the cumulative dose irradiated on the VOI based on the desired or actual RTS positioning. In some embodiments subsequent doses are based (for example biasing future doses based on prior doses) on comparing the future time based VOI positioning refinements relative to future time based RTS positioning or desired RTS positioning. In some embodiments future RTS command updates are based at least in part on alternative imaging VOI positioning 1523.

Figure 15D:
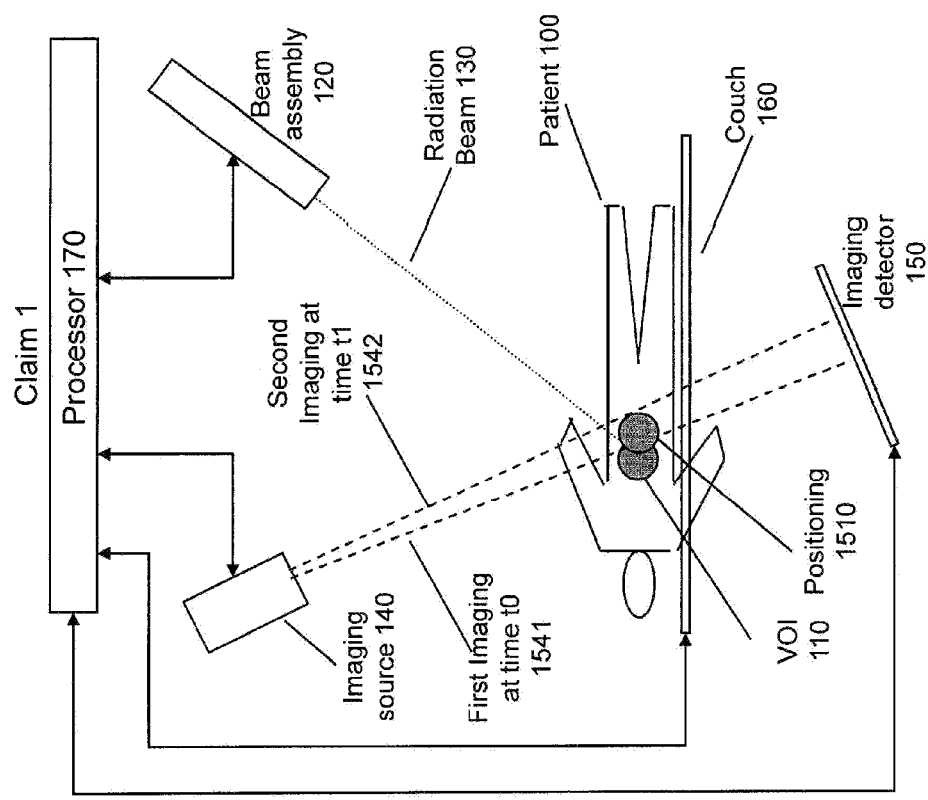
FIG. 15D shows a system, according to an embodiment.

FIG. 15D shows a system, according to an embodiment. The system includes an imaging element configured to generate a first observation of an object. Various embodiments of the imaging element include, for example, at least one of, an imaging source 140 and an imaging detector 150. The first observation is generated at a first time (1541). The object is associated with a volume of interest (VOI) 110, wherein the VOI 110 includes a volume within a body of a patient 100. The system further includes one or more processors 170 configured to determine a first positioning (such as, positioning 1510) of the VOI 110 based at least in part on the first observation of the object, determine a second time for the imaging element based at least in part on a positioning parameter associated with the first positioning of the VOI 110, and generate a second observation of the object at the second time 1542. For an embodiment, the one or more processors 170 are further configured to assist the imaging element in generating the second observation at the second time 1542. For an embodiment, the patient is located on, for example, a couch 160.

A specific embodiment of the system includes a radiation treatment system. An embodiment of the radiation treatment system include a radiation treatment system element (such as, the beam assembly 120 and the radiation beam 130) configured to aid administering of radiation to at least a portion of the patient 100 based on one or more of the first observation and the second observation. In some embodiments the radiation treatment element (for example one or more of a radiation assembly, radiation beam, radiation beam controller, processor, a patient, a patient furniture (for example table, couch, etc.), imaging element, imaging source, imaging detector, etc.) may aid administering of radiation by delivering a beam, adjusting a beam, directing a beam, filtering a beam modulating (on/off/intensity) a beam over time, modulating a beam over space (by adjusting a shape, or a size, or a number of active subbeams), adjusting the patient for example by moving the patient with a patient couch or requesting the patient to modify a positioning, adjusting a parameter of an imaging system for example field of view or intensity or timing of an observation. For an embodiment, determining the second time for the imaging element to generate the second observation of the object is further based on the radiation treatment system element constraint. For an embodiment, the radiation treatment system element constraint is a maximum rate of movement.

For at least some of the described embodiments, the patient includes a human being. For at least some of the described embodiments, the object includes at least a portion of the VOI. For at least some of the described embodiments, the object includes an artificial marker or a natural marker. For at least some of the described embodiments, the object includes a marker on or within a body of the patient. For at least some of the described embodiments, the VOI includes diseased tissue. For at least some of the described embodiments, the VOI includes healthy tissue.

For an embodiment of the system, the imaging element is associated with a radiation parameter, and the radiation parameter indicates an amount of radiation to which the patient is exposed through a use of the imaging element, and wherein the one or more processors 170 are further configured to additionally determine the second time 1542 for the second observation based on the radiation parameter. For another embodiment, the imaging element is associated with a radiation parameter, the radiation parameter indicating an amount of radiation to which the patient is exposed through a use of the imaging element, and wherein the one or more processors 170 are further configured to additionally determine the second time 1542 for the second observation based on the radiation parameter and a radiation threshold. For at least some embodiments, the radiation threshold includes one or more of a radiation dose, a cumulative radiation dose, and a radiation intensity. For an embodiment, additionally determining the second time for the second observation based on the radiation parameter and the radiation threshold includes determining whether the radiation parameter is less than the radiation threshold.

Various embodiments of the imaging element includes one or more of a still-picture camera, a video camera, an x-ray component, a magnetic resonance imaging (MRI) component, a computer tomography (CT) component, an ultrasound component, and a positron emission tomography (PET) component.

For an embodiment, determining a first positioning of the VOI based at least in part on the first observation of the object includes determining a future positioning of the VOI. For another embodiment, determining a first positioning of the VOI based at least in part on the first observation of the object includes determining a plurality of future positionings of the VOI. For an embodiment, a first future positioning of the plurality of future positionings is associated with a first future time, and a second future positioning of the plurality of future positionings is associated with a second future time. For an embodiment, the one or more processors 170 are further configured to determine the second time 1542 for the second observation of the object based on the first future positioning and the second future positioning. For an embodiment, determining the first positioning of the VOI based at least in part on the first observation of the object includes predicting a future positioning error associated with the VOI. For an embodiment, determining a first positioning of the VOI based at least in part on the first observation of the object includes predicting a plurality of future positioning errors associated with the VOI.

For an embodiment, a first future positioning error of the plurality of future positioning errors is associated with a first future time, and a second future positioning error of the plurality of future positioning errors is associated with a second future time. For an embodiment, the one or more processors 170 are further configured to determine the second time 1542 for the second observation of the object based on the first future positioning error and the second future positioning error.

For various embodiments, the positioning parameter includes one or more of a location, an orientation, an angle, an error, an error interval, an error norm, and deformation information associated with one or more portions of the VOI 110. For various embodiments, the positioning parameter includes a change in one or more of a location, an orientation, an angle, an error, an error interval, an error norm, and deformation information associated with one or more portions of the VOI 110. For an embodiment, the change includes one or more of a velocity, a slope, an acceleration, and a path. For various embodiments, the positioning parameter includes one or more of an estimated positioning of the VOI 110, an estimated positioning error of the VOI 110, and a future positioning of the VOI 110.

For an embodiment, the one or more processors 170 are further configured to determine the first positioning of the VOI based on one or more markers associated with the VOI.

For an embodiment, the one or more processors 170 are further configured to determine a third time for the imaging element to generate a third observation of the object, and wherein a first time difference between the first time 1541 and the second time 1542 is different from a second time difference between the second time 1542 and the third time.

For an embodiment, a timing difference between the first time 1541 and the second time 1542 is an integer multiple of a unit of time. For example, the baseline (or default) imaging observations may spaced by a (approximate) fixed period (for example 100 ms or 1 sec), but a subset of the imaging Observations may be avoided (or gated or disabled) based on VOI positioning, for example to reduce irradiation to the patient, reduce energy consumption or increase the life of the imaging element. The resulting imaging observations will be spaced by a multiple of the fixed period, which may simplify one or more of the modeling, design, training, adaptation, estimation or prediction of the VOI positioning based on the imaging observations, since the imaging observations are spaced by a structured pattern.

For an embodiment, the one or more processors 170 are further configured to assist in configuring the radiation treatment system element based on the first positioning. For an embodiment, configuring the radiation treatment system element includes configuring one or more of a beam positioning, a beam location, a beam orientation, a beam intensity, a beam shape, a number of subbeams, a beam multi-leaf collimator, a patient positioning, a patient table, a patient couch, a VOI table, and a VOI couch.

For an embodiment, the positioning parameter is based at least in part on one or more estimated positionings of the VOI 110. For an embodiment, the positioning parameter includes a quality metric associated with the first observation.

For an embodiment, the one or more processors 170 are further configured to determine the positioning parameter by jointly processing a plurality of observations, the plurality of observations including the first observation. For an embodiment, the one or more processors 170 are further configured to determine the positioning parameter by jointly processing a plurality of observations, the plurality of observations including the first observation and a pre-treatment observation, wherein the pre-treatment observation is determined before the first observation. For an embodiment, a first quality of the pre-treatment observation is higher than a second quality of the first observation. For an embodiment, the first quality is higher than the second quality because of one or more of: a higher dimensionality, a greater field of view, a higher resolution. For an embodiment, the pre-treatment observation includes a magnetic resonance observation (MRI), a computer tomography (CT) observation, an ultrasound observation, a positron emission tomography (PET) observation, a three-dimensional Observation, or a four-dimensional representation.

An embodiment includes a method. The method includes generating, by an imaging element, a first observation of an object, the first observation generated at a first time, the object associated with a volume of interest (VOI), the VOI including a volume within a body of a patient, determining a first positioning of the VOI based at least in part on the first observation of the object, determining a second time for the imaging element based at least in part on a positioning parameter associated with the first positioning of the VOI and, generating a second observation of the object at the second time. While this method is described as including a body of a patient, it is to be understood that the described embodiment can include any type of body, structure, or material.

For an embodiment, the method includes aiding administering radiation, by a radiation treatment system element of a radiation treatment system, to at least a portion of the patient based on one or more of the first observation and the second observation.

Figure 15E:
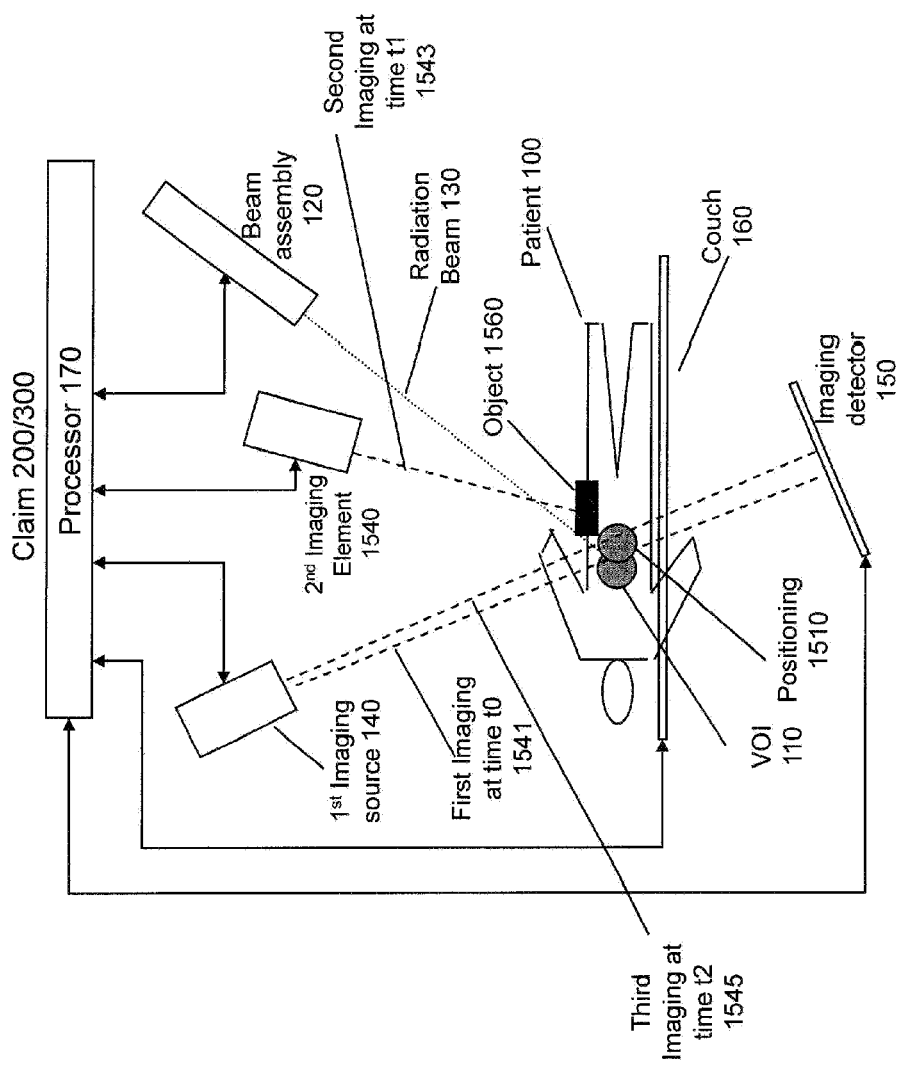
FIG. 15E shows another system, according to an embodiment.

FIG. 15E shows another system, according to an embodiment. This embodiment includes a first imaging element (including, for example, imaging source 140 and imaging detector 150) configured to generate a first observation of a first object, the first observation of the first object is generated at a first time 15411, the first object is associated with a volume of interest (VOI 110). For an embodiment, the VOI 110 is a volume within a body of a patient 100. This embodiment of the system further includes a second imaging element 1540 configured to generate a first observation of a second object (for example, object 1560), the first observation of the second object is generated at a second time 1543, the second object associated with the VOI 110. The system further includes one or more processors 170 configured to determine a first positioning (for example, positioning 1510) of the VOI 110 based at least in part on the first observation of the first object and the first Observation of the second object, determine a third time 1545 for the first imaging element based at least in part on a positioning parameter associated with the first positioning of the VOI 110, and generate a second Observation of the first object at the third time 1545. For an embodiment, the first object and the second object are the same object.

For an embodiment, the VOI 110 is a first VOI, the first imaging element is associated with delivering a first radiation dose to a second VOI, and the second imaging element is associated with delivering a second radiation dose to the third VOI, wherein the first radiation dose is lower than the second radiation dose.

For an embodiment, the one or more processors 170 are further configured to determine a fourth time for the second imaging element 1543 to generate a second observation of the second object. For an embodiment, a first difference between the first time and the third time is less than a second difference between the second time and the fourth time.

For various embodiments, the first imaging element includes at least one of an optical imaging element, a wireless imaging element, a magnetic imaging element, or an ultrasound imaging element. For various embodiments, the second imaging element is an x-ray system, a computer tomography (CT) Observation system, a positron emission tomography (PET) observation system, or a portal imaging element.

For an embodiment, the system includes a radiation treatment system. For an embodiment, the radiation treatment system includes a radiation treatment system element configured to aid administering of radiation to at least a portion of the patient based on one or more of the first observation and the second observation. An embodiment includes configuring the radiation treatment system element based on the first positioning. For an embodiment, configuring the radiation treatment system element includes configuring one or more of a beam positioning, a beam location, a beam orientation, abeam intensity, abeam shape, a number of subbeams, a beam multi-leaf collimator, a patient positioning, a patient table, a patient couch, a VOI table, and a VOI couch. For an embodiment, determining the third time for the imaging element to generate the second observation of the first object is further based on the radiation treatment system element constraint of the radiation treatment system.

For an embodiment, the first object includes at least a portion of the VOI. For an embodiment, the first object includes an artificial marker or a natural marker. For an embodiment, the first object includes a marker on or within a body of the patient.

For an embodiment, the first imaging element is associated with a radiation parameter, the radiation parameter indicating an amount of radiation to which the patient is exposed through a use of the first imaging element, and wherein the one or more processors 170 are further configured to additionally determine the third time 1545 for the second observation of the first object based on the radiation parameter.

For an embodiment, determining a first positioning of the VOI 110 based at least in part on the first observation of the first object and the first observation of the second object includes determining a future positioning of the VOI. For an embodiment, determining a first positioning of the VOI 110 based at least in part on the first observation of the first object and the first observation of the second object includes determining a plurality of future positionings of the VOI 110. For an embodiment, determining the first positioning of the VOI 110 based at least in part on the first observation of the first object and the first observation of the second object includes predicting a future positioning error associated with the VOI 110.

For an embodiment, the positioning parameter includes one or more of a location, an orientation, an angle, an error, an error interval, an error norm, and deformation information associated with one or more portions of the VOI. For an embodiment, the positioning parameter includes a change in one or more of a location, an orientation, an angle, an error, an error interval, an error norm, and deformation information associated with one or more portions of the VOI.

An embodiment further includes determining a fourth time for the first imaging element, and generating a third observation of the first object, and wherein a first time difference between the first time 1541 and the third time 1545 is different from a second time difference between the third time 1545 and the fourth time.

For an embodiment, the positioning parameter includes a quality metric associated with the first observation of the first object. An embodiment further includes determining the positioning parameter by jointly processing a plurality of observations, the plurality of observations including the first observation of the first object and a pre-treatment observation, wherein the pre-treatment observation is determined before the first observation of the first object. For an embodiment, a first quality of the pre-treatment observation is higher than a second quality of the first observation of the first object.

An embodiment includes a method. The method includes generating, by a first imaging element (wherein the first imaging element includes, for example, the imaging source 140 and/or the imaging detector 150), a first observation of a first object (for example, object 1560 or VOI 110), the first observation of the first object generated at a first time 1541, the first object associated with a volume of interest (VOI 110), the VOI 110 being a volume within a body of a patient 100. The method further includes generating, by a second imaging element 1540, a first observation of a second object, the first observation of the second object generated at a second time 1543, the second object associated with the VOI 110, determining a first positioning of the VOI 110 based at least in part on the first observation of the first object and the first observation of the second object, and determining a third time 1545 for the first imaging element based at least in part on a positioning parameter associated with the first positioning of the VOI 110, and generating a second observation of the first object at the third time.

Another embodiment includes another system. This embodiment of the system includes a first imaging element (wherein the first imaging element includes, for example, the imaging source 140 and/or the imaging detector 150) configured to generate a first observation of a first object the first observation of the first object generated at a first time 1541, the first object associated with a volume of interest (VOI 110), the VOI 110 being a volume within a body of a patient 100. The system further includes a second imaging element 1540 configured to generate a first observation of a second object (such as, object 1560), the first observation of the second object generated at a second time 1543, the second object associated with the VOI 110. The system further includes one or more processors 170 configured to determine a first positioning of the VOI 110 based at least in part on the first observation of the first object and the first observation of the second object determine a plurality of imaging times for the first imaging element to generate a plurality of additional observations of the first object, each of the plurality of imaging times associated with a different one of the plurality of additional observations, determine a third time 1545 for the second imaging element 1540 based at least in part on a positioning parameter associated with the first positioning of the VOI 110, and generate a second observation of the second object at the third time 1545.

For an embodiment, the plurality of imaging times for the first imaging element are periodic as determined by a stream of images of the first imaging element. For an embodiment, the VOI 110 is a first VOI and wherein the first imaging element is associated with delivering a first radiation dose to a second VOI and the second imaging element is associated with delivering a second radiation dose to the third VOI, the first radiation dose being lower than the second radiation dose.

For an embodiment, the first imaging element includes at least one of an optical imaging element, a wireless imaging element, a magnetic imaging element, or an ultrasound imaging element. For an embodiment, the second imaging element includes at least one of an x-ray system, a computer tomography (CT) observation, a positron emission tomography (PET) observation, or a portal imaging element.

Figure 15F:
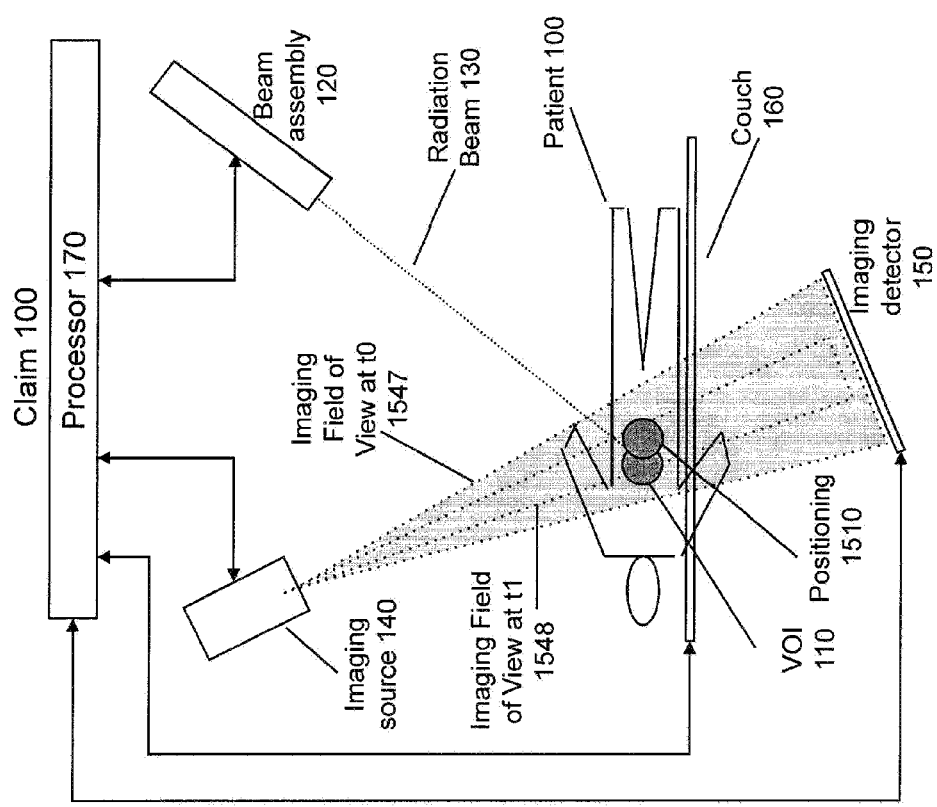
FIG. 15F shows another system, according to an embodiment.

FIG. 15F shows another system, according to an embodiment. This embodiment includes an imaging element (the imaging element including, for example, the imaging source 140 and the imaging detector 150) configured to generate an observation of an object in accordance with a first value of an adjustable parameter (wherein the adjustable parameter includes, for example, an imaging field of view at, for example, a first time 1547). For an embodiment, the object is associated with a volume of interest (VOI 110), the VOI 110 being a volume within a body of a patient 100. The system further includes one or more processors 170 configured to determine a positioning of the VOI 110 based at least in part on the observation of the object, determine a second value of the adjustable parameter (wherein the adjustable parameter includes, for example, an imaging field of view at, for example, a second time 1548) based at least in part on a positioning parameter associated with the positioning of the VOI, and assist in providing the second adjustable parameter to the imaging element.

For an embodiment, the second adjustable parameter controls an intensity of an imaging source of the imaging element. For various embodiments, the second adjustable parameter includes one or more of a duration, a duty cycle, a radiation dose, an observation size, an observation shape, an observation positioning, and an imaging field of view of the imaging element source.

For an embodiment, the system includes a radiation treatment system, and the radiation treatment system includes a radiation treatment system element configured to aid administering of radiation to at least a portion of the patient 100 based on the observation.

For an embodiment, the object includes at least a portion of the VOI. For an embodiment, the object includes an artificial marker or a natural marker. For an embodiment, the object includes a marker on or within a body of the patient.

For an embodiment, the imaging element is associated with a radiation parameter, the radiation parameter indicating an amount of radiation to which the patient is exposed through a use of the imaging element, and wherein the one or more processors 170 are further configured to additionally determine the second adjustable parameter for a second observation based on the radiation parameter.

For an embodiment, determining the positioning of the VOI 110 is based at least in part on the observation of the object includes determining a future positioning of the VOI 110. For an embodiment, determining the positioning of the VOI 110 based at least in part on the observation of the object includes determining a plurality of future positionings of the VOI 110. For an embodiment, determining the positioning of the VOI 110 based at least in part on the observation of the object includes predicting a future positioning error associated with the VOI 110.

For an embodiment, the positioning parameter includes one or more of a location, an orientation, an angle, an error, an error interval, an error norm, and deformation information associated with one or more portions of the VOI. For an embodiment, the positioning parameter includes a change in one or more of a location, an orientation, an angle, an error, an error interval, an error norm, and deformation information associated with one or more portions of the VOI.

An embodiment includes determining a third value of an adjustable parameter for the imaging element.

An embodiment further includes the one or more processors 170 being adapted to configure the radiation treatment system element based on the positioning. For an embodiment, configuring the radiation treatment system element includes configuring one or more of a beam positioning, a beam location, a beam orientation, a beam intensity, a beam shape, a number of subbeams, a beam multi-leaf collimator, a patient positioning, a patient table, a patient couch, a VOI table, and a VOI couch.

For an embodiment, determining the second adjustable parameter for the imaging element is further based on the radiation treatment system element constraint of the radiation treatment system.

For an embodiment, the positioning parameter includes a quality metric associated with the observation. For an embodiment, positioning parameter is determined by jointly processing a plurality of observations, the plurality of observations including the observation and a pre-treatment observation, wherein the pre-treatment observation is determined before the observation. For an embodiment, a first quality of the pre-treatment observation is higher than a second quality of the first observation.

An embodiment includes method. The method includes generating, by an imaging element (the imaging element including, for example, the imaging source 140 and the imaging detector 150), an observation of an object in accordance with a first value of an adjustable parameter (wherein the adjustable parameter includes, for example, an imaging field of view), the object being associated with a volume of interest (VOI 110), the VOI 110 being a volume within a body of a patient 100. The method further includes determining a positioning of the VOI 110 (for example, positioning 1510) based at least in part on the observation of the object, determining a second value of the adjustable parameter based at least in part on a positioning parameter associated with the positioning of the VOI, and assisting in providing the second adjustable parameter to the imaging element.

Figure 15G:
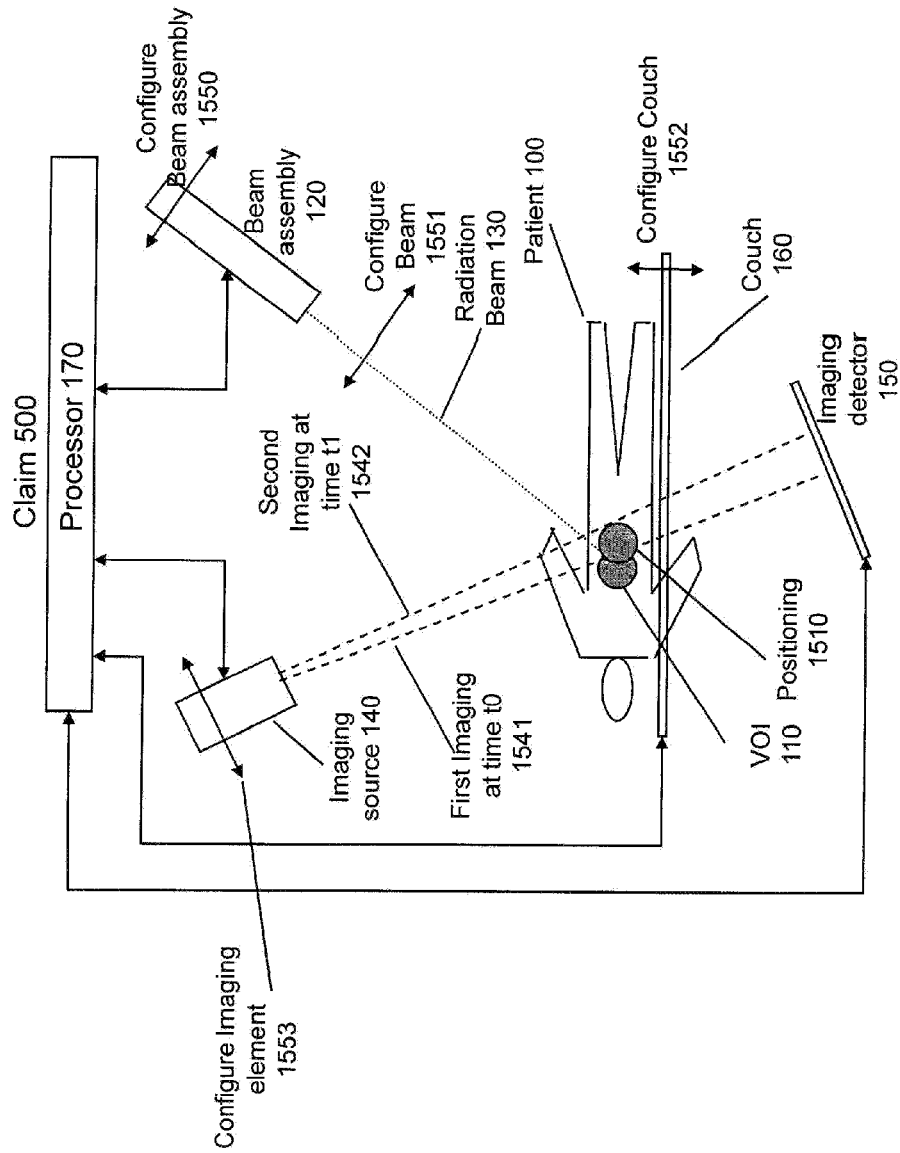
FIG. 15G shows another system, according to an embodiment.

FIG. 15G shows another system, according to an embodiment. This embodiment includes an imaging element (wherein the imaging element includes, for example, the imaging source 140 and/or the imaging detector 150) configured to generate first observation of an object, the first observation generated at a first time 1541, the object associated with a volume of interest (VOI 110), the VOI 110 including a volume within a body of a patient 110. The system further includes one or more processors 170 configured to determine a first positioning of the VOI 110 based at least in part on the first observation of the object, determine a second time 1542 for the imaging element based at least in part on a positioning parameter associated with the first positioning, and a time offset, wherein the time offset is determined based upon a positioning change delay of the system, and generate a second observation of the object at the second time 1542. For an embodiment, the positioning change delay of the system includes a time delay based on the first positioning and a second positioning of the VOI.

The positioning delay of the system, and therefore, the time offset (or alternatively a delay or lag), can be caused by various different elements (or alternatively subsystems, components, parts or portions) of the system (for example a radiation treatment system). As shown, a delay of the system may be due to a configuring (or alternatively a positioning or a change of positioning) of, for example, at least one of the beam assembly 1550, the beam 1551, a couch 1552, and/or the imaging element 1553, or a processing time of processor 170, or an imaging time of an imaging element, or a communication or storage or retrieval time between radiation treatment system elements.

For an embodiment, the system includes a radiation treatment system, and the radiation treatment system further includes a radiation treatment system element configured to aid administering of radiation to at least a portion of the patient based on one or more of the first observation and the second observation. For an embodiment, a first positioning of a radiation treatment system element is based on the first positioning of the VOI and a second positioning of the radiation treatment system element is based on a second positioning of the VOI and the one or more processors further configured to determine the time offset based on the first positioning of the radiation treatment system element and the second positioning of the radiation treatment system element.

For an embodiment, the radiation treatment system element includes at least one of a beam element, a beam control element, a beam assembly element, an imaging element, a patient couch element.

For an embodiment, the positioning change delay is associated with changing the positioning of one or more radiation treatment system elements.

An embodiment includes determining a motion model of at least a portion of the patient wherein the first VOI positioning or the second VOI positioning is based on the motion model. For an embodiment, the first VOI positioning is determined based on a plurality of prior VOI positionings. For an embodiment, the radiation treatment system element positioning is determined based on a plurality of prior positionings of a radiation treatment system element. An embodiment further includes measuring errors of a desired radiation treatment system element of the radiation treatment system relative to an actual radiation treatment system element of the radiation treatment system, and updating the time offset based on the errors.

For embodiment, the imaging element is associated with a radiation parameter, the radiation parameter indicating an amount of radiation to which the patient is exposed through a use of the imaging element, and wherein the one or more processors 170 are further configured to additionally determine the second time 1542 for the second observation based on the radiation parameter.

For an embodiment, determining a first positioning of the VOI 110 based at least in part on the first observation of the object includes determining a future positioning of the VOI 110. For an embodiment, determining a first positioning of the VOI 110 based at least in part on the first observation of the object includes determining a plurality of future positionings of the VOI. For an embodiment, determining the first positioning of the VOI 110 based at least in part on the first observation of the object includes predicting a future positioning error associated with the VOI 110.

An embodiment, determining a third time for the imaging element, and generating a third observation of the object, and wherein a first time difference between the first time 1541 and the second time 1542 is different from a second time difference between the second time 1542 and the third time.

An embodiment includes configuring the radiation treatment system element of the radiation treatment system based on the first positioning. For an embodiment, configuring the radiation treatment system element includes configuring one or more of a beam positioning, a beam location, a beam orientation, a beam intensity, a beam shape, a number of subbeams, a beam multi-leaf collimator, a patient positioning, a patient table, a patient couch, a VOI table, and a VOI couch. For an embodiment, determining the second time for the imaging element to generate the second observation of the object is further based on a radiation treatment system element constraint of the radiation treatment system.

An embodiment includes a method. The method includes generating, by an imaging element (wherein the imaging element includes, for example, the imaging source 140 and/or the imaging detector 150) of a system, a first observation of an object, the first observation generated at a first time 1541, the object associated with a volume of interest (VOI) 110, the VOI 110 including a volume within a body of a patient 100. The method further includes determining a first positioning (for example, positioning 1510) of the VOI 110 based at least in part on the first observation of the object, determining a second time for the imaging element based at least in part on a positioning parameter associated with the first positioning, and a time offset, wherein the time offset is determined based upon a positioning change delay of the system, and generating a second observation of the object at the second time.

Figure 15H:
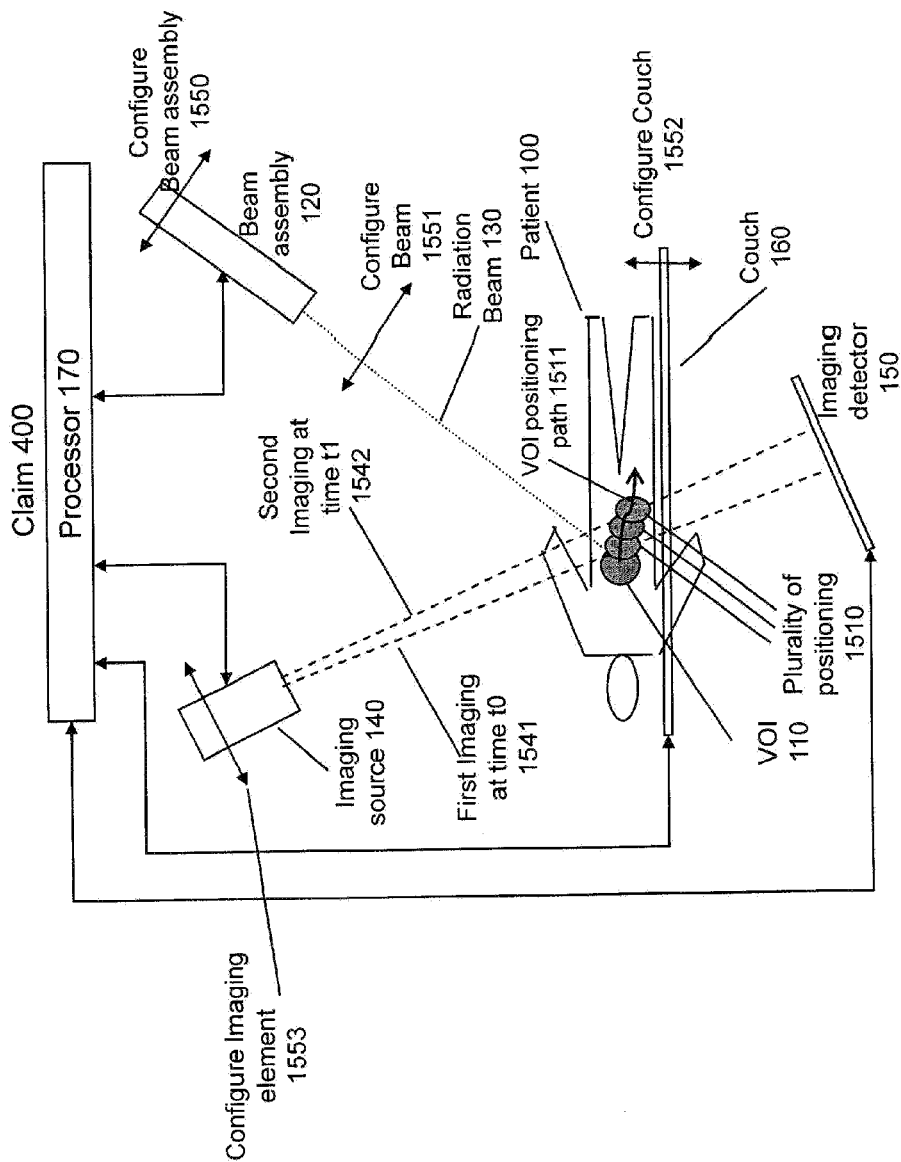
FIG. 15H shows another system, according to an embodiment.

FIG. 15H shows another system, according to an embodiment. This embodiment includes a radiation treatment system. The radiation treatment system includes an imaging element (wherein the imaging element includes, for example, the imaging source 140 and/or the imaging detector 150) configured to generate a first observation of an object, the first observation generated at a first time 1541, the object being associated with a volume of interest (VOI), the VOI being a volume within a body of a patient 100. The radiation treatment system further includes one or more processors 170 configured to determine a plurality of positionings 1510 of the VOI 110 based at least in part on the first observation of the object, determine a first radiation treatment system configuration configuring, for example, at least one of the beam assembly 1550, the beam 1551, a couch 1552, and/or the imaging element 1553) based at least in part on one or more parameters of the plurality of positionings of the VOI, configuring the radiation treatment system based on the first radiation treatment system configuration, and aiding administering radiation, by a radiation treatment system element of the radiation treatment system, to at least a portion of the patient 100 based on the first radiation treatment system configuration.

For an embodiment, each of the plurality of positionings 1510 of the VOI 110 is associated with one or more of a plurality of times. For an embodiment, each of the plurality of positionings of the VOI is associated with one or more of a plurality of locations of the VOI 110.

For an embodiment, the one or more processors 170 determine the plurality of positionings of the VOI 110 based at least in part on the first observation of the object utilizing a plurality of functions, and at least two of the plurality of positionings are determined based on two or more of the plurality of functions. For an embodiment, the plurality of functions includes two or more of a linear estimator, a non-linear estimator, a Kalman filter, an artificial neural network. For an embodiment, the plurality of positionings of the VOI is determined utilizing the plurality of functions based on one or more of a periodic model, a pseudo-periodic model or cyclostationary model.

For an embodiment, the radiation treatment system element of the radiation treatment system includes one or more of a radiation beam, a radiation beam assembly, a patient, a patient couch, a patient table, a second imaging system. For an embodiment, the first radiation treatment system configuration includes one or more of a time, a positioning, a location, an angle, an intensity, a shape, a number of subbeams, a multi-leaf collimator setting, for configuring a radiation treatment system element of the radiation treatment system.

For an embodiment, a first positioning of the plurality of positionings of the VOI is associated with a first time 1541, and a second positioning of the plurality of positionings of the VOI is associated with a second time 1542, and wherein a first tentative radiation treatment system configuration is based on the first positioning of the VOI and a second tentative radiation treatment system configuration is based on the second positioning of the VOI. For an embodiment, the one or more processors 170 are further configured to select the first radiation treatment system configuration between the first tentative radiation treatment system configuration and the second tentative radiation treatment system configuration.

For an embodiment the selection between the first tentative radiation system configuration and the second tentative radiation treatment system configuration is based on a radiation dose (or a positioning parameter error between the first positioning of the VOI and the first tentative positioning of a RTS element, etc.) of the first radiation treatment system configuration on the first positioning of the VOI and/or a radiation dose (or a positioning parameter error between the second positioning of the VOI and the second tentative positioning of a RTS element, etc.) of the second radiation treatment system configuration on the second positioning of the VOI.

For an embodiment, the one or more processors 170 are further configured to determine a VOI positioning path 1511 based on the plurality of positionings of the VOI 110. For an embodiment, the one or more processors 170 are further configured to determining the first radiation treatment system configuration based on the VOI positioning path 1551. For an embodiment, the one or more processors 170 are further configured to determine an additional positioning of the VOI 110 based on the plurality of positionings of the VOI 110. For an embodiment, the additional positioning of the VOI 110 is determined based on one or more of an interpolation, an extrapolation and a model fitting of the plurality of positionings of the VOI 110 or a constraint on the VOI 110.

For an embodiment, the one or more processors 170 are further configured to determine a radiation treatment system element path of a radiation treatment system element of the radiation treatment system based on the first radiation treatment system configuration. For an embodiment, determining the radiation treatment system element path includes determining one or more radiation treatment system element parameters over a plurality of times. For an embodiment, the one or more processors 170 are further configured to determine a VOI positioning path 1511 based on the plurality of positionings of the VOI, and compare the radiation treatment system element path with the VOI positioning path 1511. For an embodiment, the one or more processors 170 are further configured to determine a radiation treatment dose irradiation on at least a part of the VOI 110, based on the comparison of the radiation treatment system element path with the VOI positioning path 1511.

An embodiment includes determining the first radiation treatment system configuration based on a second radiation treatment system configuration.

An embodiment includes a method of radiation treatment. The method includes configuring an imaging element (wherein the imaging element includes, for example, the imaging source 140 and/or the imaging detector 150) to generate a first observation of an object, the first observation generated at a first time 1541, the object associated with a volume of interest (VOI 110), the VOI 110 being a volume within a body of a patient 100. The method further includes determining a plurality of positionings 1510 of the VOI 110 based at least in part on the first observation of the object, determining a first radiation treatment system configuration based at least in part on one or more parameters of the plurality of positionings of the VOI configuring (configuring, for example, at least one of the beam assembly 1550, the beam 1551, a couch 1552, and/or the imaging element 1553) the radiation treatment system based on the first radiation treatment system configuration, and aiding administering radiation, by a radiation treatment system element of the radiation treatment system, to at least a portion of the patient based on the first radiation treatment system configuration.

ADDITIONAL EMBODIMENTS

An embodiment includes a method for providing radiation treatment to a volume of interest (VOI) associated with a patient. The method includes detecting a positioning of each of a plurality of objects associated with the VOI, the positionings of the objects being determined with respect to a reference point having a known spatial relationship to a radiation treatment system, the radiation treatment system configured to provide a radiation beam, determining relative positionings of the plurality of objects with respect to each other, accessing a first mapping model that maps the relative positionings of the objects to determine a relative positioning of the VOI, the relative positioning of the VOI being relative to the positionings of the objects, and using the positionings of the objects and the relative positioning of the VOI to direct a radiation beam of the radiation treatment system to the VOI.

For an embodiment, the radiations treatment system operates in a treatment coordinate system, and the method further includes obtaining a pre-treatment body image that includes at least a portion of the objects and the VOI, mapping the pre-treatment body image into a corrected pre-treatment body image having a coordinate system that is consistent with the treatment coordinate system, and using the object positionings to create a treatment body image in the treatment coordinate system. The method further includes creating an enhanced treatment body image by performing an optimization to map the at least a portion of the objects from the corrected pre-treatment body image onto the treatment body image, the optimized mapping using a positioning offset to minimize a positioning difference between a common feature in the corrected pre-treatment body image and the treatment body image. For an embodiment, the pre-treatment body image is created in a different apparatus than where the treatment body image is created.

An embodiment further includes accessing a second mapping model that maps the relative positionings of the objects to a positionings of healthy tissue of the patient, the positionings of the healthy tissue being associated with the VOI, and using the positionings of the healthy tissue to direct the radiation beam away from the healthy tissue.

An embodiment further includes determining the first mapping model, including taking scans of a first patient in a plurality of physical positionings, wherein each physical positioning is different and involves at least a translation and/or a rotation of one or more selected from the first patient's head, torso, and appendages relative to another position, wherein the first patient has a plurality of first objects attached to the first patient's body. For each scan, relative positionings of the first objects with respect to each other and with respect to the VOI are determined. Further, relative positionings of the first objects at each of the plurality of positionings are used to calculate the functional model, wherein the functional model provides an approximate positionings of the VOI for an input of relative positionings of the first objects for new physical positionings of the first patient.

An embodiment further includes determining the first mapping model, including performing at least one scan of the patient to detect a positionings of the VOI, and correlating the positionings of the VOI to positionings of markers at a surface of the patient's body, wherein the positionings of the markers have a predetermined spatial relationship with the positionings of the objects. At least one embodiment further includes performing at least one additional scan of the patient during the radiation treatment, identifying positionings of the VOI in the scan and objects in the at least one additional scan, and updating the mapping model based on the identified positionings in the at least one additional scan. At least one embodiment further includes identifying, in an output of a scan, a reference object of known size, and scaling the positionings of the markers based on at least one known length obtained from the reference object. For at least one embodiment, the first mapping model is determined by using the correlation to modify a mapping model built from a plurality of scans of one or more other patients. For at least one embodiment, a plurality of scans are performed, and wherein the patient is in a different physical positioning for each of the plurality of scans. For at least one embodiment, each scan provides a multi-dimensional data point comprising the positionings of the VOI and the positionings of the markers, and further includes calculating a function that approximates the functional behavior of the plurality of multi-dimensional data points, wherein the function provides the first mapping of the positionings of the VOI to positionings of the objects that do not correspond directly with the positionings of the markers during the plurality of scans. For at least one embodiment, the functional approximation is determined by a constrained optimization with constraints defined by a model of body movement. For at least one embodiment, the constraints are dependent on a body type of the patient.

An embodiment further includes determining a body type of the patient from among a plurality of possible body types, wherein the first mapping model corresponds to the determined body type.

An embodiment further includes detecting a first positioning of each of a set of markers associated with the radiation treatment system at a first time, where at least one of the set of markers associated with the radiation treatment system is attached to a beam assembly that is configured to provide a radiation beam, determining a trajectory of the radiation beam from the first positionings of the set of markers, and using the determined trajectory at the first time to configure the radiation treatment system such that the trajectory of the radiation beam is focused at a VOI associated with a patient. An embodiment further includes calibrating the beam assembly including for each of a plurality of positionings of the set of markers associated with the radiation treatment system, detecting a trajectory of the radiation beam, and based on the positionings of the set of markers and the respective trajectories, calculating a trajectory function that approximates the relationship between the positionings of the set of markers and the trajectory of the beam assembly, wherein the trajectory function is used to determine a trajectory of the radiation beam from the first positionings of the set of markers.

An embodiment further includes detecting a plurality of positionings of the VOI using at least one object, each of the plurality of positionings of the VOI being detected at a different time during treatment with the radiation beam, based on the plurality of positionings, determining one or more parameters for a time-dependent motion model that accounts for a motion of the VOI using the motion model to determine a new trajectory for the radiation beam relative to the VOI providing the new trajectory to a radiation treatment system, and the radiation treatment system adjusting the radiation beam to have the new trajectory.

An embodiment further includes tracking movement of the objects, and shutting off the radiation beam when the movement is faster than a threshold value. For at least one embodiment, the threshold value is determined by how fast a trajectory of the radiation beam can be changed to account for the movement.

An embodiment further includes using the positionings of the VOI to direct two or more radiation beams to the VOI. An embodiment further includes using the two or more radiation beams to provide lower power radiation beams as compared to power required when using one radiation beam. For at least one embodiment, the two or more radiation beams are configured to provide radiation to a larger surface area of the VOI compared to one radiation beam. For at least one embodiment, the two or more radiation beams are optimized to reduce damage to surrounding healthy tissue while providing radiation to the VOI.

An embodiment includes a computer product that includes a tangible computer readable medium storing a plurality of instructions for controlling a processor to perform an operation. For an embodiment, when executed, the instructions perform steps of detecting a positioning of each of a plurality of objects associated with the VOI the positionings of the objects being determined with respect to a reference point having a known spatial relationship to a radiation treatment system, the radiation treatment system configured to provide a radiation beam, determining relative positionings of the objects with respect to each other, accessing a first mapping model that maps the relative positionings of the objects to determine a relative positioning of the VOI the relative positioning of the VOI being relative to the positionings of the objects, and using the positionings of the objects and the relative positioning of the VOI to direct a radiation beam of the radiation treatment system to the VOI.

An embodiment includes a system for providing radiation treatment to a VOI associated with a patient. The system includes one or more beam assemblies, each configured to emit a radiation beam, a plurality of detectors configured to receive signals from a plurality of objects associated with the VOI and one or more processors that are in communication with the one or more beam assemblies and the plurality of detectors. The one or more processors are configured to detect a positioning of each of the objects using the signals received from the objects, the positionings of the objects being determined with respect to a reference point having a known spatial relationship to the one or more beam assemblies, determine relative positionings of the objects with respect to each other, access a first mapping model that maps the relative positionings of the objects to determine a relative positioning of the VOI the relative positioning of the VOI being relative to the positionings of the objects, and use the positionings of the objects and the relative positioning of the VOI to direct a radiation beam of the radiation treatment system to the VOI.

An embodiment includes a method for providing radiation treatment to VOI associated with a patient. The method includes detecting a first positioning of each of a set of markers associated with the radiation treatment system at a first time, where at least one of the set of markers associated with the radiation treatment system is attached to a beam assembly that is configured to provide a radiation beam, determining a trajectory of the radiation beam from the first positionings of the set of markers, and using the determined trajectory at the first time to configure the radiation treatment system such that the trajectory of the radiation beam is focused at a location of the VOI. An embodiment further includes detecting positionings of each of the set of markers associated with the radiation treatment system at a plurality of times while the radiation treatment system is adjusting to the configuration, using the detected positionings to track the trajectory of the radiation beam as the radiation treatment system is adjusting to the configuration, and stopping the adjustment of the beam assembly when a desired beam trajectory is achieved. An embodiment further includes sending commands to the beam assembly to adjust the beam assembly, wherein the commands are determined using the determined trajectory at the first time. An embodiment further includes calculating a beam error between the trajectory determined using the first positionings of the set of markers associated with the radiation treatment system and an expected trajectory, the expected trajectory being determined from adjustment commands provided to the beam assembly before the first time, using the beam error to obtain new adjustment commands, and sending the new adjustment commands to the beam assembly as part of a process of focusing the radiation beam at the location of the VOI. An embodiment further includes detecting positionings of each of the set of markers associated with the radiation treatment system at a plurality of times while the radiation treatment system is adjusting to the configuration, the plurality of times including the first time, calculating an error between the trajectory determined using positionings of the set of markers associated with the radiation treatment system at the plurality of times, and determining the new adjustment commands based on an optimization of a cost function that includes the errors.

For at least some embodiments, the beam assembly has a plurality of degrees of freedom, including two angular degrees of freedom and at least two positional degrees of freedom. For at least some embodiments, determining the trajectory of the radiation beam from the first positionings of the set of markers is accomplished using a first function that defines a trajectory for a given set of positionings of the set of markers further includes calculating the first function, including detecting the positionings of the set of markers at a plurality of positionings of the beam assembly, for each combination of positioning, determining an actual trajectory of the radiation beam by measuring the radiation beam at a plurality of positionings, and defining the first function to provide an output (or a given set of positionings of the set of markers that approximately matches the corresponding actual trajectory. For at least one embodiment, defining the first function to provide an output for a given set of positionings of the set of markers that approximately matches the corresponding actual trajectory includes optimizing variables of the first function by optimizing a cost function that includes a difference in the output of the first function for a given set of positionings of the set of markers and the corresponding actual trajectory. For at least one embodiment, the first function is calculated during a calibration process performed before treatment of the patient.

For at least one embodiment, a calculation of the first function is updated during treatment of the patient, and wherein the update calculation uses one or more errors between a trajectory determined using the first function and an actual trajectory determined by measuring the radiation beam at a plurality of positionings.

At least some embodiments further include detecting first positioning of each of a second set of beam markers at the first time, where the second set of beam markers are attached to a second beam assembly that is configured to provide a second radiation beam, determining a second trajectory of the second radiation beam from the first positionings of the second set of beam markers, and using the determined second trajectory at the first time to adjust the second beam assembly relative to the VOI such that the second trajectory of the second radiation beam is focused at the VOI associated with a patient.

An embodiment includes a system for providing radiation treatment to VOI associated with a patient. The system includes one or more beam assemblies, each configured to emit a radiation beam, a plurality of detectors configured to receive signals from a set of markers, at least one of the set of markers attached to the one or more beam assemblies, and one or more processors that are in communication with the one or more beam assemblies and the plurality of detectors. The one or more processors are configured to detect a first positioning of each of the set of set of markers at a first time, determine a trajectory of the radiation beam from the first positionings of the set of markers, and use the determined trajectory at the first time to configure the radiation treatment system such that the trajectory of the radiation beam is focused at a location of the VOI.

An embodiment includes a method of creating a functional model that predicts a positionings of the VOI of a first patient, the first patient having a body including a head, a torso, and appendages. The method includes taking scans of a first patient in a plurality of physical positionings, wherein each physical positioning is different and involves a positioning change of one or more selected from the first patient's head, torso, and appendages relative to a first positioning, wherein the first patient has a plurality of first objects attached to the first patient's body, for each scan, determining relative positionings of the first objects with respect to each other and with respect to the VOI, and using the relative positionings of the first objects at each of the plurality of positionings to calculate the functional model, wherein the functional model provides an approximate positioning of the VOI for an input of relative positionings of the first objects for new physical positionings of the first patient. For an embodiment, the functional model has a defined set of allowable relative positionings of markers, the method further includes providing an error message when relative positionings of the first objects outside of the defined set of allowable relative positionings are input to the functional model. An embodiment further includes determining the defined set of allowable relative positionings of objects based on a normal range of motion for a human. For at least some embodiments, the normal range of motion is scaled based on proportions of the first patient.

At least some embodiment further include taking a scan of a second patient, wherein the second patient has a plurality of second objects attached to the second patient's body, the second objects being attached at locations substantially the same as the first objects attached to the first patient's body, and using the functional model obtained from the scans of the first patient and the scan of the second patient to compute a second functional model for the second patient. For at least some embodiments, the positioning of attachment for the first and second objects is defined with respect to one or more body parts. For at least some embodiments, the first patient and the second patient have one or more shared body characteristics. For at least some embodiments, the shared characteristics include at least one of body shape, height, width, and body mass. At least some embodiments further include scaling the scans of the second patient of the functional model to account for a difference in proportions of the first patient's body relative to the second patient's body.

An embodiment includes a method of directing a radiation beam to a VOI associated with a patient that is moving. The method includes detecting a plurality of positionings of the VOI using at least one object associated with the VOI, each of the plurality of positionings being detected at a different time during treatment with the radiation beam, based on the plurality of positionings, determining one or more parameters for a time-dependent motion model that accounts for a motion of the VOI, using the motion model to determine a new trajectory for the radiation beam relative to the VOI, providing the new trajectory to a radiation treatment system, and the radiation treatment system adjusting the radiation beam to have the new trajectory. For at least some embodiments, the motion model has the form $a+bt+ct^2$, where the one or more parameters include the elements a, b, and c. For at least some embodiments, the one or more parameters include a time offset $\Delta t$ that accounts for a delay of the radiation treatment system to adjust the radiation beam to a new positioning relative to the VOI. For at least some embodiments, the new trajectory is calculated at a current time t using a time of $t+\Delta t$. At least some embodiments further include determining the time offset $\Delta t$ based on at least one of a change in a parameter of the configuration adjustment model compared to a value of the parameter at a previous time, a change in the positioning of the VOI from one time to another, and a value for a parameter of the motion model. At least some embodiments further include measuring a beam trajectory at one or more of the times at which the positionings of the VOI is detected, determining a desired beam trajectory at the one or more of the times at which the positionings of the VOI is detected, computing one or more beam errors between the measured beam trajectory and the desired beam trajectory, and determining the time offset $\Delta t$ based on the one or more beam errors.

For at least some embodiments, the radiation beam positioning is configured more frequently than the detection of the positionings of the VOI.

At least some embodiments further include selecting the motion model from a plurality of available motion models based on the plurality of detected positionings. At least some embodiments further include determining one or more parameters for the plurality of available models, calculating an error in each model from the plurality of detected positionings, and selecting the available model with the lowest error.

At least some embodiments further include determining a change in at least one of the parameters between two times, comparing the change to a threshold, and stopping the radiation beam when the change exceeds the threshold.

For at least some embodiments, the motion model predicts a positioning change of the VOI, the method further includes using the motion model to predict a positioning of the VOI at a second time subsequent to a most recent detected positioning, and determining the new trajectory based on the predicted positioning of the VOI. For at least some embodiments, the radiation beam is adjusted to the predicted positioning of the VOI at approximately the second time. At least some embodiments further include calculating a value indicating an amount of movement of the patient based on at least a portion of the detected positioning of the VOI, comparing the value to a threshold, and stopping the radiation beam when the value exceeds the threshold.

For at least some embodiments, detecting a positioning of the VOI using at least one object includes detecting positionings of a plurality of objects, and using a mapping model to determine the positionings of the VOI based on an input of the detected positionings of the objects.

For at least some embodiments, the motion model predicts a motion of a desired beam trajectory, the method further includes determining a desired beam trajectory at each of the times for the detected positionings of the VOI, and using the motion model to predict a new desired beam trajectory at a second time subsequent to a most recent detected positionings of the VOI, and providing the new desired beam trajectory to a radiation treatment system.

For at least some embodiments, the motion model predicts a change in a desired input to the radiation treatment system as a function of time, the method further includes measuring a beam trajectory at a first time at which the positionings of the VOI is detected, determining a desired beam trajectory at the first time, computing a beam error between the measured beam trajectory and the desired beam trajectory, and updating at least one of the parameters of the motion model based on the beam error.

An embodiment further includes determining a plurality of beam errors at a plurality of times, wherein a new value for the at least one of the parameters is determined by optimizing a cost function that includes the plurality of beam errors.

An embodiment includes a system for directing a radiation beam to a VOI associated with a patient that is moving. The system includes a beam assembly configured to emit a radiation beam, one or more detectors configured to receive a signal from at least one object, and one or more processors that are in communication with the beam assembly and the one or more detectors. The one or more processors are configured to detect a plurality of positionings of the VOI using the at least one object, each of the plurality of positionings being detected at a different time during treatment with the radiation beam, based on the plurality of positionings, determine one or more parameters for a time-dependent motion model that accounts for a motion of the VOI, use the motion model to determine a new trajectory for the one or more radiation beams, and adjust the beam assembly such that the radiation beam has the new trajectory.

FIG. 16 is an illustration of another image guided radiation treatment system according to an embodiment. As shown, for an embodiment, a new diagnostic imaging positioning 1650 at time t3, is used to predict the VOI positioning 1553. For this embodiment the predicted VOI positioning 1553 (without the assistance of Imaging positioning 1522 and with the assistance of New diagnostic imaging position 1650) is improved (smaller confidence interval) relative to predicted VOI positioning 1550 (without the assistance of Imaging positioning 1522).

IX. Computer System

Figure 12:
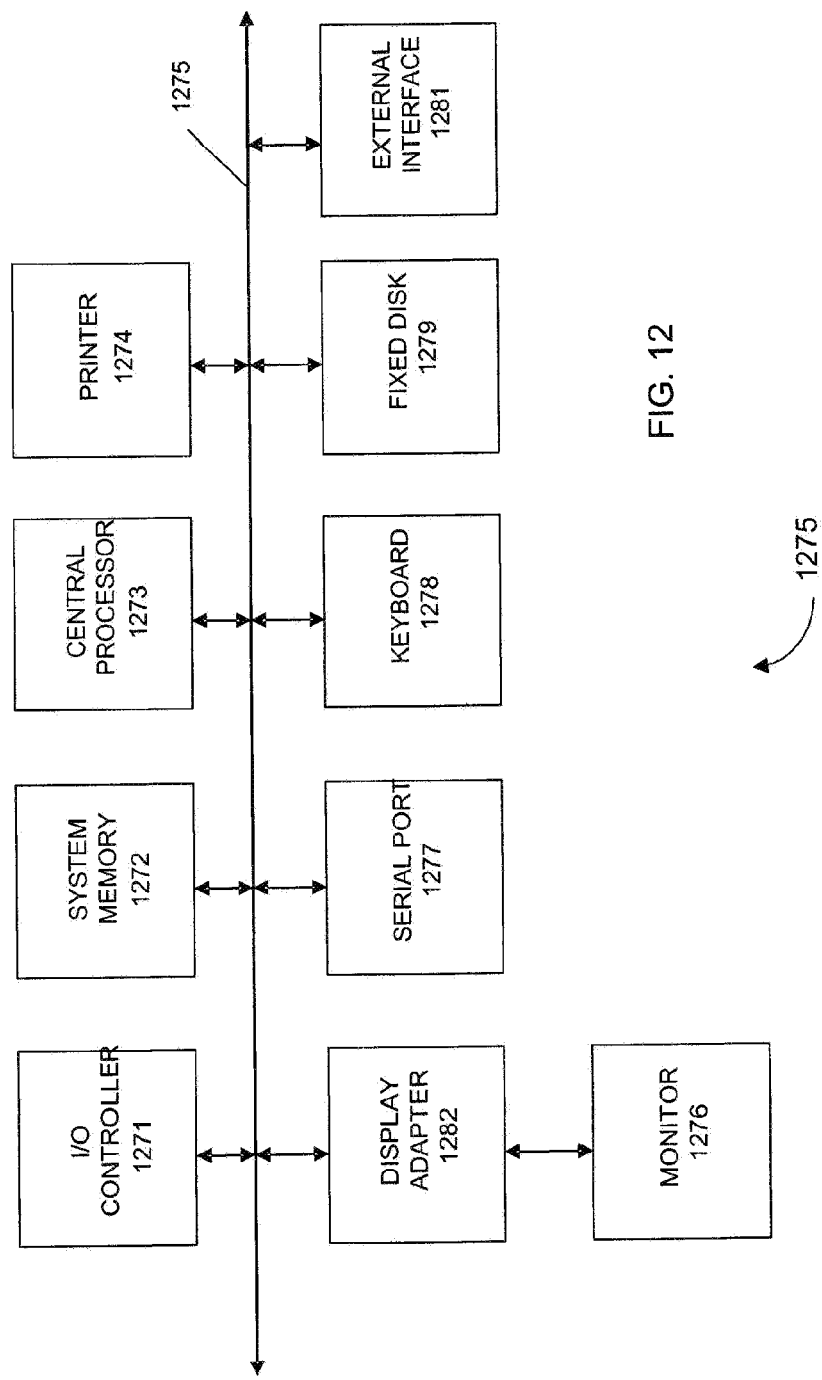
FIG. 12 shows a block diagram of an example computer system 1200 usable with system and methods according to at least one embodiment.

Any of the computer systems mentioned herein may utilize any suitable number of subsystems. Examples of such subsystems are shown in FIG. 12 in computer apparatus 1200. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 12 are interconnected via a system bus 1275. Additional subsystems such as a printer 1274, keyboard 1278, fixed disk 1279, monitor 1276, which is coupled to display adapter 1282, and others are shown. Peripherals and input/output (I/O) devices, which couple to I/O controller 1271, can be connected to the computer system by any number of means known in the art, such as serial port 1277. For example, serial port 1277 or external interface 1281 can be used to connect computer system 1200 to a wide area network such as the Internet, a mouse input device, or a scanner. The interconnection via system bus 1275 allows the central processor 1273 to communicate with each subsystem and to control the execution of instructions from system memory 1272 or the fixed disk 1279, as well as the exchange of information between subsystems. The system memory 1272 and/or the fixed disk 1279 may embody a computer readable medium. Any of the values mentioned herein can be output from one component to another component and can be output to the user.

A computer system can include a plurality of the same components or subsystems, e.g., connected together by external interface 1281 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the described embodiments can be implemented in the form of control logic using hardware and/or using computer software in a modular or integrated manner. Based on the disclosure and teachings provided herein, a person of ordinary skill in the art will know and appreciate other ways and/or methods to implement embodiments of the described embodiments using hardware or a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the described embodiments may be created using a data signal encoded with such programs. Computer readable media encoded with the program code may be packaged with a compatible device or provided separately from other devices (e.g., via Internet download). Any such computer readable medium may reside on or within a single computer program product (e.g. a hard drive, a CD, or an entire computer system), and may be present on or within different computer program products within a system or network. A computer system may include a monitor, printer, or other suitable display for providing any of the results mentioned herein to a user.

Any of the methods described herein may be totally or partially performed with a computer system including a processor, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

What is claimed:

1. A system comprising:
   a first imaging element configured to generate a first observation of a first object, the first observation of the first object generated at a first time (t1) during a radiation delivery, the first object associated with a volume of interest (VOI), the VOI being a volume within a body of a patient;
   a second imaging element configured to generate a first observation of a second object, the first observation of the second object generated at a second time (t2) during the radiation delivery, the second object associated with the VOI; and
   one or more processors configured to:
      determine a first positioning of the VOI based at least in part on the first observation of the first object and the first observation of the second object;
      adaptively determine a third time (t3) for the first imaging element based at least in part on a positioning parameter associated with the first positioning of the VOI, wherein the positioning parameter includes at least one of a velocity or an acceleration of the VOI, and wherein the adaptively determined third time (t3) is dependent on the at least one of the velocity or the acceleration of the VOI exceeding a threshold; and
      generate, using the first imaging element, a second observation of the first object at the third time (t3) during the radiation delivery, wherein t3>t2>t1.

2. The system recited in claim 1, wherein the first object and the second object are the same object.

3. The system recited in claim 1, wherein the VOI is a first VOI, and wherein the first imaging element is associated with delivering a first radiation dose to a second VOI, and the second imaging element is associated with delivering a second radiation dose to the third VOI, the first radiation dose being lower than the second radiation dose.

4. The system recited in claim 3, wherein the one or more processors are further configured to determine a fourth time for the second imaging element to generate a second observation of the second object.

5. The system recited in claim 4, wherein a first difference between the first time and the third time is less than a second difference between the second time and the fourth time.

6. The system recited in claim 1, wherein the first imaging element comprises at least one of an optical imaging element, a wireless imaging element, a magnetic imaging element, or an ultrasound imaging element.

7. The system recited in claim 1, wherein the second imaging element is an x-ray system, a computer tomography (CT) observation system, a positron emission tomography (PET) observation system, or a portal imaging element.

8. The system of claim 1, wherein the system comprises a radiation treatment system, and the radiation treatment system comprises:
   a radiation treatment system element configured to aid in administering radiation to at least a portion of the patient based on one or more of the first observation and the second observation.

9. The system recited in claim 1, wherein the first object comprises at least a portion of the VOI.

10. The system recited in claim 1, wherein the first object comprises an artificial marker or a natural marker.

11. The system recited in claim 1, wherein the first object comprises a marker on or within a body of the patient.

12. The system recited in claim 1, wherein the first imaging element is associated with a radiation parameter, the radiation parameter indicating an amount of radiation to which the patient is exposed through a use of the first imaging element, and wherein the one or more processors are further configured to additionally determine the third time for the second observation of the first object based on the radiation parameter.

13. The method recited in claim 1, wherein determining a first positioning of the VOI based at least in part on the first observation of the first object and the first observation of the second object comprises determining a future positioning of the VOI.

14. The method recited in claim 1, wherein determining a first positioning of the VOI based at least in part on the first observation of the first object and the first observation of the second object comprises determining a plurality of future positionings of the VOI.

15. The system recited in claim 1, wherein determining the first positioning of the VOI based at least in part on the first observation of the first object and the first observation of the second object comprises predicting a future positioning error associated with the VOI.

16. The system recited in claim 1, wherein the positioning parameter comprises one or more of a location, an orientation, an angle, an error, an error interval, an error norm, and deformation information associated with one or more portions of the VOI.

17. The system recited in claim 1, wherein the positioning parameter comprises a change in one or more of a location, an orientation, an angle, an error, an error interval, an error norm, and deformation information associated with one or more portions of the VOI.

18. The system recited in claim 1, further comprising determining a fourth time for the first imaging element, and generating a third observation of the first object, and wherein a first time difference between the first time and the third time is different from a second time difference between the third time and the fourth time.

19. The system recited in claim 8, further configuring the radiation treatment system element based on the first positioning.

20. The system recited in claim 19, wherein configuring the radiation treatment system element comprises configuring one or more of a beam positioning, a beam location, a beam orientation, a beam intensity, a beam shape, a number of subbeams, a beam multi-leaf collimator, a patient positioning, a patient table, a patient couch, a VOI table, and a VOI couch.

21. The system recited in claim 8, wherein determining the third time for the imaging element to generate the second observation of the first object is further based on the radiation treatment system element constraint of the radiation treatment system.

22. The system recited in claim 1, wherein the positioning parameter comprises a quality metric associated with the first observation of the first object.

23. The system recited in claim 1, further comprising determining the positioning parameter by jointly processing a plurality of observations, the plurality of observations including the first observation of the first object and a pre-treatment observation, wherein the pre-treatment observation is determined before the first observation of the first object.

24. The system recited in claim 23, wherein a first quality of the pre-treatment observation is higher than a second quality of the first observation of the first object.

25. A method comprising:
generating, by a first imaging element, a first observation of a first object, the first observation of the first object generated at a first time (t1) during a radiation delivery, the first object associated with a volume of interest (VOI), the VOI being a volume within a body of a patient;
generating, by a second imaging element, a first observation of a second object, the first observation of the second object generated at a second time (t2) during the radiation delivery, the second object associated with the VOI; and
determining a first positioning of the VOI based at least in part on the first observation of the first object and the first observation of the second object;
adaptively determining a third time (t3) for the first imaging element based at least in part on a positioning parameter associated with the first positioning of the VOI, wherein the positioning parameter includes at least one of a velocity or an acceleration of the VOI, and wherein the adaptively determined third time (t3) is dependent on the at least one of the velocity or the acceleration of the VOI exceeding a threshold;
generating, using the first imaging element, a second observation of the first object at the third time (t3) during the radiation delivery, wherein t3>t2>t1.

26. The method recited in claim 25, wherein the first object and the second object are the same object.

27. The method recited in claim 25, wherein the VOI is a first VOI, and wherein the first imaging element is associated with delivering a first radiation dose to a second VOI, and the second imaging element is associated with delivering a second radiation dose to the third VOI, the first radiation dose being lower than the second radiation dose.

28. The method recited in claim 27, further comprising determining a fourth time for the second imaging element to generate a second observation of the second object.

29. The method recited in claim 28, wherein a first difference between the first time and the third time is less than a second difference between the second time and the fourth time.

30. The method recited in claim 25, wherein the first imaging element comprises at least one of an optical imaging element, a wireless imaging element, a magnetic imaging element, or an ultrasound imaging element.

31. The method recited in claim 25, wherein the second imaging element comprises at least one of an x-ray, a computer tomography (CT) observation, a positron emission tomography (PET) observation, or a portal imaging element.

32. The method of claim 25, further comprising:
aiding administering of radiation, by a radiation treatment system element of a radiation treatment system, to at least a portion of the patient based on one or more of the first observation and the second observation.

33. The method recited in claim 25, wherein the first object comprises at least a portion of the VOI.

34. The method recited in claim 25, wherein the first object comprises an artificial marker or a natural marker.

35. The method recited in claim 25, wherein the first object comprises a marker on or within a body of the patient.

36. The method recited in claim 25, wherein the first imaging element is associated with a radiation parameter, the radiation parameter indicating an amount of radiation to which the patient is exposed through a use of the first imaging element, and further comprising additionally determining the third time for the second observation of the first object based on the radiation parameter.

37. The method recited in claim 25, wherein determining a first positioning of the VOI based at least in part on the first observation of the first object and the first observation of the second object comprises determining a future positioning of the VOI.

38. The method recited in claim 25, wherein determining a first positioning of the VOI based at least in part on the first observation of the first object and the first observation of the second object comprises determining a plurality of future positionings of the VOI.

39. The method recited in claim 25, wherein determining the first positioning of the VOI based at least in part on the first observation of the first object and the first observation of the second object comprises predicting a future positioning error associated with the VOI.

40. The method recited in claim 25, wherein the positioning parameter comprises one or more of a location, an orientation, an angle, an error, an error interval, an error norm, and deformation information associated with one or more portions of the VOI.

41. The method recited in claim 25, wherein the positioning parameter comprises a change in one or more of a location, an orientation, an angle, an error, an error interval, an error norm, and deformation information associated with one or more portions of the VOI.

42. The method recited in claim 25, further comprising determining a fourth time for the first imaging element, and generating a third observation of the first object, and wherein a first time difference between the first time and the third time is different from a second time difference between the third time and the fourth time.

43. The method recited in claim 32, further comprising configuring the radiation treatment system element based on the first positioning.

44. The method recited in claim 43, wherein configuring the radiation treatment system element comprises configuring one or more of a beam positioning, a beam location, a beam orientation, a beam intensity, a beam shape, a number of subbeams, a beam multi-leaf collimator, a patient positioning, a patient table, a patient couch, a VOI table, and a VOI couch.

45. The method recited in claim 32, wherein determining the third time for the imaging element to generate the second observation of the first object is further based on the radiation treatment system element constraint of the radiation treatment system.

46. The method recited in claim 25, wherein the positioning parameter comprises a quality metric associated with the first observation of the first object.

47. The method recited in claim 25, further comprising determining the positioning parameter by jointly processing a plurality of observations, the plurality of observations including the first observation of the first object and a pre-treatment observation, wherein the pre-treatment observation is determined before the first observation of the first object.

48. The method recited in claim 47, wherein a first quality of the pre-treatment observation is higher than a second quality of the first observation of the first object.

49. The system recited in claim 1, wherein generating the second observation of the first object at the third time (t3) is avoided if the velocity or the acceleration of the VOI does not exceed the threshold.

50. The system recited in claim 1, further comprising the second imaging element generating observations periodically, and the first imaging element generating observations when a predicted VOI positioning parameter is not satisfactory when compared to a threshold.

* * * * *